(12) United States Patent  
Lawrence

(10) Patent No.: US 7,902,330 B2  
(45) Date of Patent: Mar. 8, 2011

(54) PROTEIN KINASE INHIBITORS AND METHODS FOR IDENTIFYING SAME

(75) Inventor: David S. Lawrence, Hartsdale, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 552 days.

(21) Appl. No.: 10/589,029

(22) PCT Filed: Feb. 14, 2005

(86) PCT No.: PCT/US2005/004410
§ 371 (c)(1),
(2), (4) Date: Jun. 21, 2007

(87) PCT Pub. No.: WO2005/079300
PCT Pub. Date: Sep. 1, 2005

(65) Prior Publication Data
US 2007/0254312 A1 Nov. 1, 2007

Related U.S. Application Data

(60) Provisional application No. 60/544,376, filed on Feb. 13, 2004.

(51) Int. Cl.
*C07K 7/00* (2006.01)
*C07K 7/06* (2006.01)
*G01N 33/53* (2006.01)

(52) U.S. Cl. .......................... 530/328; 530/300; 530/323

(58) Field of Classification Search .................. None
See application file for complete search history.

(56) References Cited

U.S. PATENT DOCUMENTS

| | | |
|---|---|---|
| 7,759,459 B2 | 7/2010 | Lawrence |
| 2004/0191926 A1 | 9/2004 | Zhang et al. |
| 2006/0211075 A1 | 9/2006 | Lawrence et al. |
| 2006/0240088 A1 | 10/2006 | Lawrence et al. |
| 2007/0254312 A1 | 11/2007 | Lawrence |
| 2008/0207538 A1 | 8/2008 | Lawrence et al. |
| 2008/0318246 A1 | 12/2008 | Lawrence et al. |
| 2009/0035796 A1 | 2/2009 | Lawrence et al. |
| 2010/0035823 A1 | 2/2010 | Lawrence |
| 2010/0041068 A1 | 2/2010 | Lawrence et al. |
| 2010/0062437 A1 | 3/2010 | Lawrence |
| 2010/0075297 A1 | 3/2010 | Lawrence |

OTHER PUBLICATIONS

Definition of derivative and analog from http://cancerweb.ncl.ac.uk/omd/about.html, pp. 1-5. Accesssed Jul. 7, 2005.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Jirousek, M. et al. "(S)-13-[(Dimethylamino)methyl]-10,11,14,15-tetrahydro-4,9:16,21-dimetheno-1H, 13H-dibenzo[e,k]pyrrolo[3,4-h][1,4,13]oxadiazacyclohexadecene-1,3(2H)-dione (LY333531) and Related Analogues: Isozyme Selective Inhibitors of Protein Kinase Cβ" J. Med. Chem. 39(14):2664-2671 (1996).
O'Brian, C.A. and Ward, N.E. "ATP-sensitive binding of melittin to the catalytic domain of protein kinase C" Molecular Pharmacology 36(3):355-359 (1989).
Martiny-Baron, G. et al. "Selective Inhibition of Protein Kinase C Isozymes by the Indolocarbazole Gö 6976" Journal of Biological Chemistry 268(13):9194-9197 (1993).
Eichholtz, T. et al. "A Myristoylated Pseudosubstrate Peptide, a Novel Protein Kinase C Inhibitor" Journal of Biological Chemistry 268(3):1982-1986 (1993).
Hofmann, J. "The potential for isoenzyme-selective modulation of protein kinase C" FASEB J. 11:649-669 (1997).
Mackay, H.J. and Twelves, C.J. "Protein kinase C: a target for anticancer drugs?" J. Endocr. Relat. Cancer 10:389-396 (2003).
Notification of Transmittal of the International Search Report and the Written Opinion of the International Searching Authority, or the Declaration (1 page) for related application PCT/US2005/004410 with an international fiing date of Feb. 14, 2005.
Declaration of Non-Establishment of International Search Report (PCT Article 17(2)(a), Rule 13ter.1(c) and (d) and 39) (1 page) for related application PCT/US2005/004410 with an international filing date of Feb. 14, 2005.

(Continued)

*Primary Examiner* — Julie Ha
(74) *Attorney, Agent, or Firm* — Amster, Rothstein & Ebenstein LLP

(57) ABSTRACT

Inhibitors of protein kinase C (PKC)α, PKCδ and PKCζ are provided which are selective for those PKC isotypes. Combinatorial libraries for identifying protein kinases are also provided, as are methods of identifying protein kinases using those libraries. Additionally, methods of treating a mammal having a deleterious condition, where the condition is dependent on a protein kinase for induction or severity, are provided. Methods of inhibiting protein kinases are also provided.

20 Claims, 49 Drawing Sheets

OTHER PUBLICATIONS

Written Opinion of the International Searching Authority (2 pages) for related application PCT/US2005/004410 with an international filing date of Feb. 14, 2005.

Lee, J H et al., entitled "A Highly Potent and Selective PkCalpha Inhibitor Generated via Combinatorial Modification pf Peptide Scaffold," J. Am. Chem. Soc., 2004, 126, 3394-3395.

* cited by examiner

1

2

3

4

5

6

7

8

9

10

11

12

13

14

15

16

17

18

19

20

| | | | |
|---|---|---|---|
| 4-(1H-Pyrrol-1-YL) Benzoic Acid |  |  |  |
| 21 | 22 | 23 | 24 |
|  |  |  |  |
| 25 | 26 | 27 | 28 |
|  |  |  |  |
| 29 | 30 | 31 | 32 |
|  |  |  |  |
| 33 | 34 | 35 | 36 |
|  |  |  |  |
| 37 | 38 | 39 | 40 |

41  42  43  44

45  46  47  48

49  50  51  52

Lasalocid, Sodium Salt 53  54  55  56

57  58  59  60

61  Trans-2,4-Pentadienoic acid 62  63  64

65  66  67  68

69  70  71  72

N-Carbobenzyloxy-L-Leucine 73  74  75  76

(S)-(-)-Indoline-2-carboxylic acid
116

117

118

119

120

121

N-[5-(Trifluoromethyl)-2-pyridyl]-L-valine
122

123

124

125

126

127

128

(±)-1-Methyl-2-cyclohexene-1-carboxylic acid
129

(1α,3α,5β)-1,3,5-Trimethyl-1,3,5-cyclohexane-tricarboxylic acid
130

3-(3-Hydroxyphenyl)-
propionic acid

4-Butoxyphenylacetic acid
226

227     228

229

230

231     232

233

234

235

236

237

238

239     240

5-Chloro-O-Anisic acid 241      242      243      244

267: 2-(2,4,5-Trichlorophenoxy)-propionic acid

268

269, 270, 271

272: 4-Chlorophenoxyacetic acid 273, 274, 275, 276

277

278: Gallic acid monohydrate 279, 280

281      282      283      284

285      286      287      288

4-Acetoxybenzoic acid    N-(4-Nitrobenzoyl)-6-Aminocaproic acid 289      290      291      292

4-(4-Methylphenyl)-4-Oxobutaric acid 293      294      295      296

2-(Benzoylmethyl)benzoic acid 297      298      299      300

304 1-Naphthylacetic acid

305 Bis(4-Chlorophenoy)acetic acid

306

307

308

309

310

311 Undecylenic acid

312

313

314

315

316

317

318

319

320

M-Anisic acid    2-Phenyl-4-Quinolinecaboxylic acid 321      322      323      324

325      326      327      328

2-Bromobenzoic acid 329      330      331      332

333      334      335      336

3-Nitrocinnamic acid 337      338      339      340

Octanoic acid 341      342      343      344

All-trans-Retinoic acid 345      346      347      348

349      350      351      352

4-Ethoxybenzoic acid 353      354      355      356

357      358      359      360

361

362

363

364

365

366

367

368

369

370

371

372

373

374

375

Aurintricarboxylic acid

385, 386, 387, 388 (3,5-Dibromo-4-Hydroxybenzoic acid)

389, 390, 391, 392

393, 394, 395 (1,3,5-Benzene-tricarboxylic acid), 396

397, 398, 399, 400

401  402  403  404

405  406  407  408

409  410  411  412

413  414  415  416

417  418  419  420

421　　　　　　422　　　　　　423　　　　　　424

425　　　　　　426　　　　　　427　　　　　　428

α-Methyl-2,4,5-trimethoxy-cinnamic acid 429　　　　　　430　　　　　　431　　　　　　432

433　　　　　　434　　　　　　435　　　　　　436

437　　　　　　438　　　　　　439　　　　　　440

441        442        443        444

445        446        447        448

2-(2-(2-Methoxyethoxy)ethoxy)acetic acid 449        450        451        452

4-Hydroxyphenylacetic acid 453        454        455        456

2-Thiopheneacetic acid 457        458        459        460

4,4'-Bis(3-Carboxy-4-chloroanilino)thityl Chloride 461  462  463  464

465  466  467  468

469  470  471  472

473  474  475  476

477  478  479  480

481  482  483  484

485  486  487  488

4-Chloro-o-tolyloxyacetic acid 489  490  491  492

3,4-Dichlorophenoxyacetic acid 493  494  495  496

Phthalylsulfathiazole 497  498  499  500

501

502

503

504

505

506

507

Propionic acid
508

509

510

511

512

513

4'-Ethyl-4-biphenylcarboxylic acid
514

515

516

517

518

519

520

521

522

2-Nitrophenylacetic acid
523

Trans-3-(2,3,5,6-Tetramethyl-benzoyl)acrylic acid
524

525

526

527

528

(+_)-2-(2-Chlorophenoxy) propionic acid
529

530

531

532

533

534

535

536

537

538

539

540

541

542

543

544

545

546

547

548

549

550

551    552

553

554

555

556

557

558

HABA [2-(4-hydroxy phenylazo)-benzoic acid]
559

560

581

582

583

584

585

586

587

588

589

590

591

2-chloro-5-nitrocinnamic acid 592

593

Trans-3-(4-ethoxy-benzoyl) acrylic acid 594

(3,5-Dimethoxyphenyl) acetic acid
609

610

611

612

613

614

615

616

617

618

619

620

621   622   623   624

625   626   627   628

629   630   631   632

2-Methoxy-4-(methylthio)-
benzoic acid 633   634   635   636

637   638   639   640

641

642

643

644

645

646

647

648

649

650

651

652

653

654

655

656

657

658

659

660

3,3,3-Tris(4-chlorophenyl) Propionic acid

661

662

663

664

665

666

667

668

669        670

671

672

673

674

675

676

677

678

679

680

681    682    683    684

685    686    687    688

689    690    691    692

2-(4-Chlorophenoxy) propionic acid    Mordant Yellow 10

693    694    695    696

Pentafluorobenzene-sulfonyl chloride 697    698    699    700

| | | |
|---|---|---|
| 1 | 1A | 4-HYDROXY-3-NITROBENZALDEHYDE |
| 2 | 1B | 6-NITROPIPERONAL |
| 3 | 1C | 4-ACETOXY-3,5-DIMETHOXYBENZALDEHYDE |
| 4 | 1D | 2-FORMYLBENZENESULFONIC ACID, SODIUM SALT HYDRATE |
| 5 | 1E | 4-CHLORO-3-NITROBENZALDEHYDE |
| 6 | 1F | 4-(DIETHYLAMINO)SALICYLALDEHYDE |
| 7 | 1G | 3,4-DIBENZYLOXYBENZALDEHYDE |
| 8 | 1H | 4-FORMYLCINNAMIC ACID |

FIG. 5B

| | | |
|---|---|---|
| 9 | 2A | 4-BENZYLOXY-3-METHOXYBENZALDEHYDE |
| 10 | 2B | 1,8-NAPHTHALALDEHYDIC ACID |
| 11 | 2C | 4-NITROBENZALDEHYDE |
| 12 | 2D | 2-AMINO-3,5-DIBROMOBENZALDEHYDE |
| 13 | 2E | 6-NITROVERATRALDEHYDE |
| 14 | 2F | 4-FORMYL-1,3-BENZENEDISULFONIC ACID, DISODIUM SALT HYDRATE |
| 15 | 2G | 2-FORMYLPHENOXYACETIC ACID |
| 16 | 2H | O-VANILLIN |

| | | | |
|---|---|---|---|
| 17 |  | 3A | 3-(3,4-DICHLOROPHENOXY)BENZALDEHYDE |
| 18 |  | 3B | 3-PHENOXYBENZALDEHYDE |
| 19 |  | 3C | 1,4-BENZODIOXAN-6-CARBOXALDEHYDE |
| 20 |  | 3D | 2-ALLYLOXYBENZALDEHYDE |
| 21 |  | 3E | SYRINGALDEHYDE |
| 22 |  | 3F | ALPHA,ALPHA,ALPHA-TRIFLUORO-P-TOLUALDEHYDE |
| 23 |  | 3G | 4-(3-DIMETHYLAMINOPROPOXY)BENZALDEHYDE |
| 24 |  | 3H | 3-METHYL-P-ANISALDEHYDE |
| 25 |  | 4A | 4-BUTOXYBENZALDEHYDE |
| 26 |  | 4B | 3,4-DIHYDROXYBENZALDEHYDE |

FIG. 5D

| # | Structure | ID | Name |
|---|---|---|---|
| 27 | | 4C | 3,5-DI-TERT-BUTYL-2-HYDROXYBENZALDEHYDE |
| 28 | | 4D | 4-FORMYLPHENYLBORONIC ACID |
| 29 | | 4E | 3-(3-(TRIFLUOROMETHYL)PHENOXY)BENZALDEHYDE |
| 30 | | 4F | HELICIN |
| 31 | | 4G | 4-(DIETHYLAMINO)BENZALDEHYDE |
| 32 | | 4H | 3-FORMYLPHENYLBORONIC ACID |
| 33 | | 5A | 4-(DIBUTYLAMINO)BENZALDEHYDE |
| 34 | | 5B | 2,3-DIHYDROXYBENZALDEHYDE |

FIG. 5E

| | | |
|---|---|---|
| 35 | 5C | 4-HEXYLOXYBENZALDEHYDE |
| 36 | 5D | 2-FORMYLPHENYLBORONIC ACID |
| 37 | 5E | 2,5-BIS(TRIFLUOROMETHYL)BENZALDEHYDE |
| 38 | 5F | 4-PROPOXYBENZALDEHYDE |
| 39 | 5G | TEREPHTHALALDEHYDE MONO-(DIETHYL ACETAL) |
| 40 | 5H | 3-CARBOXYBENZALDEHYDE |
| 41 | 6A | 3-HYDROXY-4-NITROBENZALDEHYDE |
| 42 | 6B | 3,4,5-TRIHYDROXYBENZALDEHYDE MONOHYDRATE |

| # | | ID | Name |
|---|---|---|---|
| 43 |  | 6C | 5-FORMYLSALICYLIC ACID |
| 44 |  | 6D | 2,5-DIHYDROXYBENZALDEHYDE |
| 45 |  | 6E | 3,5-DIHYDROXYBENZALDEHYDE |
| 46 |  | 6F | 3,5-DIBENZYLOXYBENZALDEHYDE |
| 47 |  | 6G | 2,3-(METHYLENEDIOXY)BENZALDEHYDE |
| 48 |  | 6H | 3,5-DIBROMOSALICYLALDEHYDE |
| 49 |  | 7A | 3-ETHOXY-4-HYDROXYBENZALDEHYDE |
| 50 |  | 7B | 2-NAPHTHALDEHYDE |
| 51 |  | 7C | 5-IODOVANILLIN |

PROTEIN KINASE INHIBITORS AND METHODS FOR IDENTIFYING SAME

CROSS-REFERENCE TO RELATED APPLICATIONS

This application is a U.S. national stage entry under 35 U.S.C. §371 of PCT International Patent Application No. PCT/US2005/004410, filed Feb. 14, 2005, and claims priority to U.S. Provisional Application No. 60/544,376, filed Feb. 13, 2004.

STATEMENT OF GOVERNMENT SUPPORT

This invention was made with government support under grant numbers CA095019 and GM38511 awarded by the National Institutes of Health. The government has certain rights in the invention.

BACKGROUND OF THE INVENTION (1) Field of the Invention

The present invention generally relates to enzyme inhibitors and methods of discovering them. More particularly, the invention is directed to protein kinase inhibitors and methods using combinatorial libraries for identifying protein kinase inhibitors.

(2) Description of the Related Art

References Cited

Borowski, P.; Resch, K.; Schmitz, H.; Heiland, M.; *Biol. Chem.* 2000, 381, 19-27.
Chan, P. M.; Miller, W. T. *Methods Mol. Biol.* 1998, 84, 75-86.
Charp, P. A.; Rice, W. G.; Raynor, R. L.; Reimund, E.; Kinkade Jr., J. M.; Ganz, T.; Selsted, M. E.; Leher, R. I.; Kuo, R. F.; *Biochem. Pharmacol.* 1988, 37, 951-6.
Cortese, R.; Monaci, P.; Nicosia, A.; Luzzago, A.; Felici, F.; Galfre, G.; Pessi, A.; Tramontano, A.; Sollazzo, M. *Curr. Opin. Biotechnol.* 1995, 6, 73-80.
Djafarzadeh, S., and Niggli, V. *Exp Cell Res* 1997, 236, 427-435.
Dostmann, W. R.; Tegge, W.; Frank, R.; Nickl, C. K.; Taylor, M. S.; Brayden, J. E. *Pharmacol. Ther.* 2002, 93, 203-15.
Eichholtz, T.; de Bont, D. B. A.; de Widt, J.; Liskamp, R. M. J.; Ploegh, H. L.; *J. Biol. Chem.* 1993, 268, 1982-6.
Feng, S.; Kapoor, T. M.; Shirai, F.; Combs, A. P.; Schreiber, S. L.; *Chem. Biol.* 1996, 3, 661-70.
Ghosh, M., Ichetovkin, I., Song, X., Condeelis, J. S., and Lawrence, D. S. *J Am Chem Soc* 2002, 124, 2440-2441.
Ghosh, M., Song, X., Mouneimne, G., Sidani, M., Lawrence, D. S., and Condeelis, J. S. *Science* 2004, 304, 743-746.
Gschwendt, M., Muller, H. J., Kielbassa, K., Zang, R., Kittstein, W., Rincke, G., and Marks, F. *Biochem Biophys Res Commun* 2004, 199, 93-98.
Hofmann, J.; *FASEB J.* 1997, 11, 649-69.
House, C.; Kemp, B. E.; *Science* 1987, 238, 1726-8.
House, C., and Kemp, B. E.; *Cell Signal* 1990, 2, 187-190.
Ishii, H., Jirousek, M. R., Koya, D., Takagi, C., Xia, P., Clermont, A., Bursell, S. E., Kern, T. S., Ballas, L. M., Heath, W. F., Stramm, L. E., Feener, E. P., and King, G. L. *Science* 1996, 272, 728-731.
Jirousek, M. R., Gillig, J. R., Gonzalez, C. M., Heath, W. F., McDonald, J. H., 3rd, Neel, D. A., Rito, C. J., Singh, U., Stramm, L. E., Melikian-Badalian, A., Baevsky, M., Ballas, L. M., Hall, S. E., Winneroski, L. L., and Faul, M. M. *J Med Chem* 1996, 39, 2664-2671.
Kemp, B. E., Pearson, R. B., and House, C. M. *Methods Enzymol* 1991, 201, 287-304

Kuroda, S., Tokunaga, C., Kiyohara, Y., Higuchi, O., Konishi, H., Mizuno, K., Gill, G. N., and Kikkawa, U. *J Biol Chem* 1996, 271, 31029-31032.
Inagaki K. et al.; *Circulation* 2004, 108, 2304-7.
Lahn, M. et al.; *Eur. J. Cancer* 2004, 40, 10-20.
Lahn, M. M. et al.; *Oncol. Rep.* 2004, 11, 515-22.
Lahn, M. M., and Sundell, K. L. *Melanoma Res* 2004, 14, 85-89.
Lam, K. S.; Liu, R.; Miyamoto, S.; Lehman, A. L.; Tuscano, J. M. *Acct. Chem. Res.* 2003, 36, 370-7.
Lawrence, D. S.; Niu, J. *Pharmacol. Ther.* 1998, 77, 81-114.
Laudanna, C., Mochly-Rosen, D., Liron, T., Constantin, G., and Butcher, E. C. *J Biol Chem* 1998, 273, 30306-30315.
Laudanna, C., Sorio, C., Tecchio, C., Butcher, E. C., Bonora, A., Bassi, C., and Scarpa, A. *Lab Invest* 2003, 83, 1155-1163.
Lee, T. R.; Lawrence, D. S.; *J. Med. Chem.* 1999, 42, 784-7.
Lee, T. R., and Lawrence, D. S. *J Med Chem* 2000, 43, 1173-1179.
Lee, J. H., Nandy, S. K., and Lawrence, D. S. *J Am Chem Soc* 2004, 126, 3394-3395.
Liu, W. S., and Heckman, C. A. *Cell Signal* 1998, 10, 529-542.
Mackay, H. J., and Twelves, C. *J. Endocr Relat Cancer* 2003, 10, 389-396.
Martiny-Baron, G., Kazanietz, M. G., Mischak, H., Blumberg, P. M., Kochs, G., Hug, H., Marme, D., and Schachtele, C. *J Biol Chem* 1993, 268, 9194-9197.
Mochly-Rosen, D., and Kauvar, L. M. *Semin Immunol* 2001, 12, 55-61.
Nishikawa, K., Toker, A., Johannes, F. J., Songyang, Z., and Cantley, L. C. *J Biol Chem* 1997, 272, 952-960.
Munger, J.; Roizman, B.; *Proc. Natl. Acad. Sci. USA* 2001, 98, 10410-5.
Musashi, M; Ota, S; Shiroshita, N. *Int. J. Hematol.* 2000, 72, 12-19.
Nachman et al., 1995. *Regul. Pept.* 1995, 57, 359-370.
Nakashima, S.; *J. Biochem.* (Tokyo) 2002, 132, 669-75.
Neid, M. et al.; *J. Biol. Chem.* 2003 (e-published—PMID 14604996).
Nguyen, J. T.; Porter, M.; Amoui, M.; Miller, W. T.; Zuckermann, R. N.; Lim, W. A.; *Chem. Biol.* 2000, 7, 463-73.
Nishikawa, K.; Toker, A.; Johannes, F.-J.; Songyang, Z.; Cantley, L. C. *J. Biol. Chem.* 1997, 272, 952-60.
O'Brian, C. A.; Ward, N. E. *Mol. Pharmacol.* 1989, 36, 355-9.
Ricouart, A.; Tartar, A.; Sergheraert, C.; *Biochem. Biophys. Res. Commun.* 1989, 165, 1382-90.
Ron, D., Luo, J., and Mochly-Rosen, D. *J Biol Chem* 1995, 270, 24180-24187.
Sarin, V. K., Kent, S. B., Tam, J. P., and Merrifield, R. B. *Anal Biochem* 1981, 117, 147-157.
Selbie, L. A., Schmitz-Peiffer, C., Sheng, Y., and Biden, T. J. *J Biol Chem* 1993, 268, 24296-2430.
Shen, K.; Keng, Y.-F.; Wu, L.; Guo, X.-L.; Lawrence, D. S.; Zhang, Z.-Y. *J. Biol. Chem.* 2001, 276, 47311-19.
Sun, J. P., Fedorov, A. A., Lee, S. Y., Guo, X. L., Shen, K., Lawrence, D. S., Almo, S. C., and Zhang, Z. Y. *J Biol Chem* 2003, 278, 12406-12414.
Toker, A. *Front Biosci* 1998, 3, D1134-1147.
Tuttle, K. R., and Anderson, P. W. *Am J Kidney Dis* 2003, 42, 456-465.
Vetrie, D. et al.; *Nature* 1993, 361, 226-33.
Wang, Q. et al.; *J. Biol. Chem.* 2003, 278, 51091-9.
Ward, N. E.; Gravitt, K. R.; O'Brian, C. A.; *Cancer Lett.* 1995, 88, 37-40.
Way, K. J.; Chou, E.; King, G. L. *Trends Pharmacol Sci*, 2000, 21, 181-7.

Wilkinson, S. E., Parker, P. J., and Nixon, J. S. *Biochem J* 1993, 294 (Pt 2), 335-337.

Xie, L., Lee, S. Y., Andersen, J. N., Waters, S., Shen, K., Guo, X. L., Moller, N. P., Olefsky, J. M., Lawrence, D. S., and Zhang, Z. Y. *Biochemistry* 2003, 42, 12792-12804.

Yeh, R. H.; Lee, T. R.; Lawrence, D. S.; *Pharmacol. Ther.* 2002, 93, 179-91.

Yeh, R.-H., Lee, T. R. Lawrence, D. S. *J. Biol. Chem.* 2001, 276, 12235-40.

Zebda, N., Bernard, O., Bailly, M., Welti, S., Lawrence, D. S., and Condeelis, J. S. *J Cell Biol* 2000, 151, 1119-1128.

Zhan, Q., Bamburg, J. R., and Badwey, J. A. *Cell Motil Cytoskeleton* 2003, 54, 1-15.

U.S. Pat. No. 6,214,852.
U.S. Pat. No. 6,248,559.
U.S. Pat. No. 6,376,747.
U.S. Pat. No. 6,660,731.

Signal transduction is the biochemical mechanism by which information is transmitted between distinct cellular sites. Signaling pathways differ from their classical biochemical counterparts in a number of ways. For example, the enzymes of glycolysis and the TCA cycle catalyze the conversion of small molecules into products, which are then passed onto the next enzymatic member of the pathway. By contrast, the protein participants of signaling pathways primarily associate with and act upon one another.

An important group of eukaryotic and viral enzymes involved in these signaling pathways are protein kinases. Protein kinases are enzymes that transfer a phosphate group from a donor molecule, usually ATP, to an amino acid residue of a protein. In signal transduction, this protein phosphorylation can activate or inhibit the activity of the protein. Types of protein kinases include serine/threonine-specific protein kinases such as phosphorylase kinase, protein kinase A, protein kinase C, $Ca^{2+}$/calmodulin-dependent protein kinase, MAP kinase, and Mos/Raf kinase; tyrosine-specific protein kinases such as receptor tyrosine kinase; histidine-specific protein kinases; and aspartic acid/glutamic acid-specific protein kinases.

Several deleterious conditions (including diseases) are associated with expression of protein kinases. These deleterious conditions include various cancers, various cardiovascular diseases, type 2 diabetes, agammaglobulinaemia, reperfusion injury, Alzheimer's disease, various neurological and neurodegenerative diseases, chemotherapy-induced alopecia, arthritis, various autoimmune diseases, various inflammatory diseases, allergies, asthma and viral virulence (Inagaki et al., 2003; Wang et al., 2003; Lahn et al., 2003, 2004; Neid et al. 2003; Vetrie et al., 1993; Stenberg et al., 2000; Munger and Roizman, 2001; U.S. Pat. Nos. 6,248,559; 6,214,852; 6,660,731).

Protein kinase C (PKC) is a family of protein kinases that generally require $Ca^{2+}$, diacylglycerol (DAG) and a phospholipids such as phosphatidylcholine for activation. There are at least 11 isoforms (=isozymes) of mammalian PKC-α, βI, βII, γ, δ, ε, ζ, η, θ, τ/λ, and μ which vary by tissue distribution, activators and substrates.

PKCs are further classified as classical or conventional PKC (α, βI, βII, and γ), which require phospholipid, DAG or phorbol ester, and $Ca^{2+}$ or activation; novel PKC (δ, ε, μ and θ), requiring phospholipid, DAG or phorbol ester, but not $Ca^{2+}$, and atypical PKC (ζ and τ/λ), requiring phospholipid, but not DAG, phorbol ester, or $Ca^{2+}$. Structural differences also distinguish these three groups of PKC from each other.

PKCs are known to be involved in many cellular functions, including cell proliferation, tumor promotion, differentiation, and apoptotic cell death. For a review of PKC structure and function, see Musashi et al., 2000.

The amino acid sequences ("consensus recognition sequences") that drive critical protein-protein kinase interactions are readily identified using combinatorial peptide-based libraries (Lam et al., 2003; Cortese et al., 1995; Dostmann et al., 2002; Chan et al., 1998). Consensus sequence information has proven helpful in piecing together signaling pathways. In addition, peptides containing these sequences are potentially useful inhibitory reagents that could furnish information about the biological role of signaling proteins. Unfortunately, consensus sequence peptides tend to display modest affinities ($K_D$ or $K_i$>low μM) for their protein targets. We (Yeh et al., 2002; Yeh et al., 2001; Shen et al., 2001; Lee et al., 1999), as well as others (See, e.g., Nguyen et al., 2000; Feng et al., 1996), have shown that consensus sequences for signaling proteins can be converted into higher affinity ligands using the 3-dimensional structure of the protein target as a guide. Nevertheless, the tertiary structure for only a small minority of all signaling proteins has been assigned, thereby limiting the generality of this approach. There is thus a need for procedures for identification of inhibitors of protein kinases. The present invention addresses that need.

SUMMARY OF THE INVENTION

Accordingly, the inventors have discovered methods for identifying protein kinase inhibitors using combinatorial libraries utilizing a consensus sequence of the protein kinase. The inventors used these methods to identify potent and selective inhibitors of protein kinase C (PKC) α, PKCβI, PKCδ, and PKCζ.

Thus, in some embodiments, the invention is directed to inhibitors of protein kinase Cα (PKCα). The inhibitors comprise A-Ala-Arg-Arg-X—B-Hyd-C-D- (SEQ ID NO:1), where A=AcHN—,

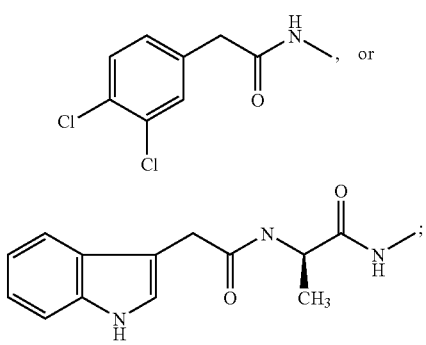

X=any amino acid or amino acid mimetic; B=Ala or a diaminopropionic acid (Dap) derivative having the formula

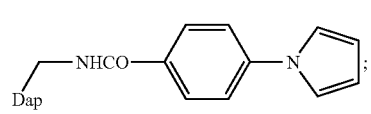

Hyd=Phe, Leu or Ile; C=Arg or Lys; and D=Ala or a Dap derivative having the formula

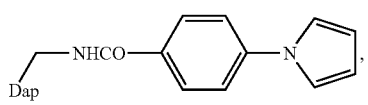

wherein any of the amino acids can alternatively be an analogous amino acid mimetic.

The invention is also directed to inhibitors of a protein kinase C (PKC). The inhibitors comprise (SEQ ID NO: 17)

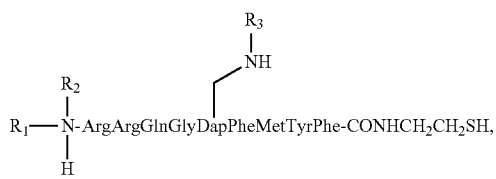

where $R_1$ and $R_3$ are independently H, Ac, a carboxylic acid from FIG. 4, or an aldehyde from FIG. 5, and $R_2$ is H, a carboxylic acid from FIG. 4, an aldehyde from FIG. 5, or nothing.

In additional embodiments, the invention is directed to compositions comprising any of the above inhibitors, in a pharmaceutically acceptable excipient.

The present invention is also directed to combinatorial libraries useful for identifying an inhibitor of a protein kinase. The combinatorial libraries comprise a plurality of compounds, each compound comprising a consensus sequence for a substrate of the protein kinase, the consensus sequence comprising at least five amino acids or mimetics, wherein at least one amino acid or mimetic is not essential to substrate binding, and wherein an amino acid or mimetic not subject to phosphorylation substitutes a canonical Ser or Thr target residue in the consensus sequence; and a chemical moiety covalently bound to the compound at the at least one nonessential amino acid or mimetic in the consensus sequence and/or the amino acid or mimetic not subject to phosphorylation substituting the canonical Ser or Thr target residue. In these combinatorial libraries, each compound comprises a different chemical moiety.

In further embodiments, the present invention is directed to methods of identifying an inhibitor of a protein kinase. The methods comprise creating a combinatorial library as described above for the protein kinase, screening the compounds in the combinatorial library for inhibitory activity of the protein kinase, and identifying any compounds in the combinatorial library that are inhibitors of the protein kinase.

The invention is additionally directed to methods of treating a deleterious condition in a mammal that is dependent on a protein kinase for induction or severity. The methods comprise contacting the mammal with an inhibitor of the protein kinase found by any of the above-described methods of identifying an inhibitor of a protein kinase.

The invention is further directed to methods of inhibiting a protein kinase. The methods comprise contacting the protein kinase with an inhibitor of the protein kinase identified by any of the above-described methods of identifying an inhibitor of a protein kinase.

In other embodiments, the invention is directed to the use of an inhibitor of a protein kinase in the manufacture of a medicament for the treatment of a deleterious condition in a mammal that is dependent on a protein kinase for induction or severity. The treatment comprises contacting the mammal with an inhibitor of the protein kinase found any of the above-described methods of identifying an inhibitor of a protein kinase.

DETAILED DESCRIPTION OF THE INVENTION

Figure 1:
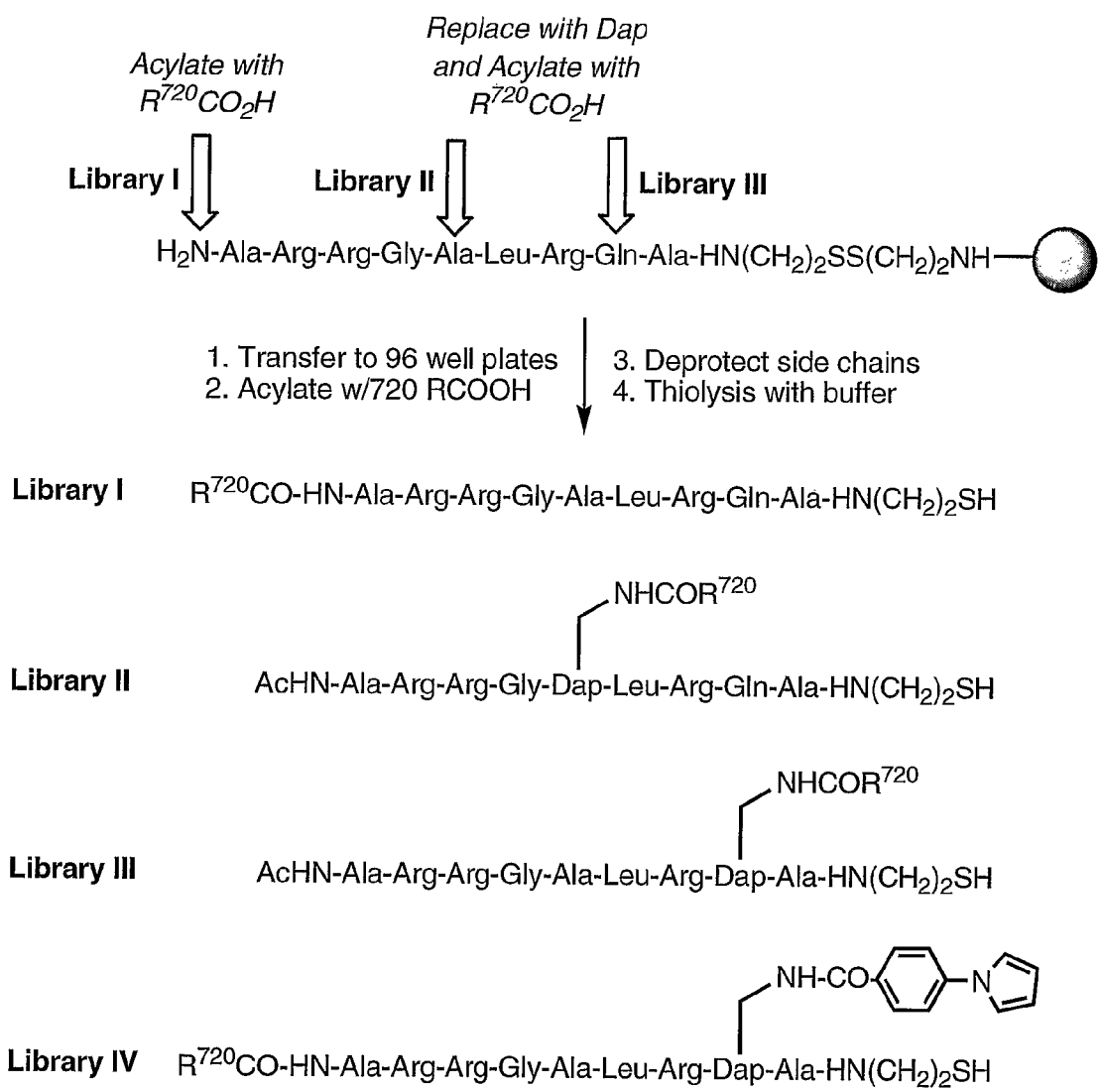
FIG. 1 shows libraries I-IV used to identify inhibitors of protein kinase Cα (PKCα).

The present invention is based on the discovery of methods for identifying protein kinase inhibitors using combinatorial libraries utilizing a consensus sequence of the protein kinase. As described in Examples 1 and 2, the inventors proved the utility of these methods by using them to identify potent and selective inhibitors of protein kinase C (PKC) α, PKCβI, PKCδ, and PKCζ.

Thus, in some embodiments, the invention is directed to inhibitors of protein kinase Cα (PKCα). The inhibitors comprise A-Ala-Arg-Arg-X—B-Hyd-C-D- (SEQ ID NO:1), where A=AcHN—,

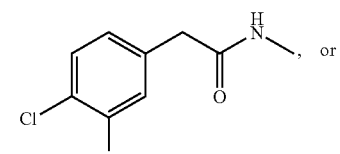

, or

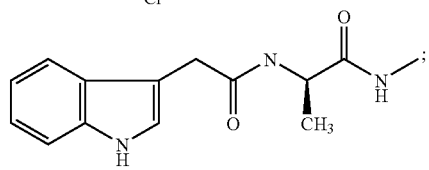

;

X=any amino acid or amino acid mimetic; B=Ala or a diaminopropionic acid (Dap) derivative having the formula

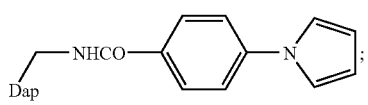

Hyd=Phe, Leu or Ile; C=Arg or Lys; and D=Ala or a Dap derivative having the formula

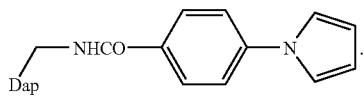

In the above formula, and throughout this application, three letter amino acid abbreviations take on their usual meaning as L-amino acids, as well as analogous amino acid mimetics, unless otherwise specified.

As used herein, an amino acid mimetic is an amino acid analog that can mimic the biological action of the amino acid. Preferred examples include D-amino acids (including natural and artificial [e.g., Dap] amino acids) and other mimetics with non-hydrolyzable peptide bonds. As used herein, non-hydrolyzable means that the bonds linking the amino acids of the peptide are less readily hydrolyzed, e.g., by proteases, than peptide bonds formed between L-amino acids. Susceptibility to proteolytic cleavage can be determined without undue experimentation, for example by labeling peptides and incubating the labeled peptides with cell extracts or purified proteases, then isolate the treated peptides to determine which peptide bonds are susceptible to proteolysis, e.g., by sequencing peptides and proteolytic fragments. Alternatively, potentially susceptible peptide bonds can be identified by comparing the amino acid sequence of an isolated peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include —CH$_2$NH— (reduced amide peptide bonds), —OCH$_2$— (ketomethylene peptide bonds), —CH(CN)NH— ((cyanomethylene)amino peptide bonds), —CH$_2$CH(OH)— (hydroxyethylene peptide bonds), —CH$_2$O—, and —CH$_2$S— (thiomethylene peptide bonds).

In the inhibitors of the present invention, any one or more than one of the amino acid moieties can be a mimetic. Preferably, the mimetic moieties permit the peptide to retain its natural conformation, or stabilize a bioactive conformation. One example of methods for preparation of nonpeptide mimetic analogs from peptides is described in Nachman et al., 1995.

Because the non-amino acid constituents of these inhibitors have a large and critical influence on their inhibitory activity (Example 1), it is believed that mimetic substitutions for the amino acid moieties would have little effect on the inhibitory activity of the inhibitors.

These inhibitors may further comprise constituents conjugated to any of the amino acid or mimetic moieties, as may be useful for detection, isolation, or quantitation of the inhibitor or its binding partners, such as PKCδ. Examples of such constituents include a His-6 moiety, a fluorescent moiety or a radioactive moiety.

The inhibitor of these embodiments preferably have a PKCα IC$_{50}$<50 μM. The IC$_{50}$ for any of the invention inhibitors can be determined without undue experimentation, for example by the methods described in Example 1. In more preferred embodiments, the inhibitor has a PKCα IC$_{50}$<10 μM; in even more preferred embodiments, the inhibitor has a PKCα IC$_{50}$<1 μM; in the most preferred embodiments, the inhibitor has a PKCα IC$_{50}$<0.1 μM.

It is also preferred that the inhibitor is specific for a PKCα. As used herein, an inhibitor is specific for a PKCα if the inhibitor has an IC$_{50}$ for a PKCα<0.1 that of all of PKC isoforms βI, γ, δ, ε, θ, η, τ and ζ. Preferably, the inhibitor has an IC$_{50}$ for a PKCα<0.05 that of any other PKC isoform. More preferably, the inhibitor has an IC$_{50}$ for a PKCα<0.01 that of any other PKC isoform.

The inhibitors of these embodiments would be expected to have similar inhibitory activity for any mammalian PKCα, including a human, a rodent, or a chimeric or otherwise novel PKCα.

In preferred embodiments, the inhibitors comprise, or consist of, (SEQ ID NO: 2)

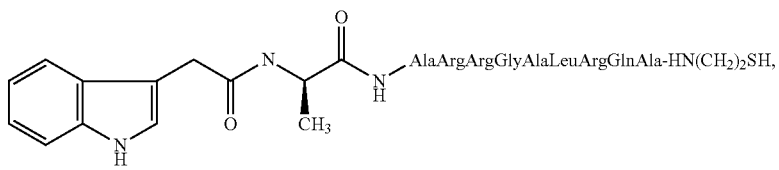

(SEQ ID NO: 2)

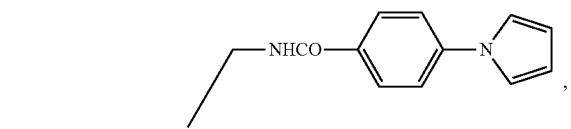

(SEQ ID NO: 2)

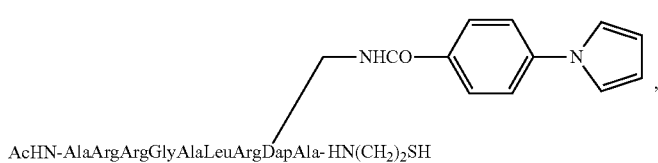

-continued

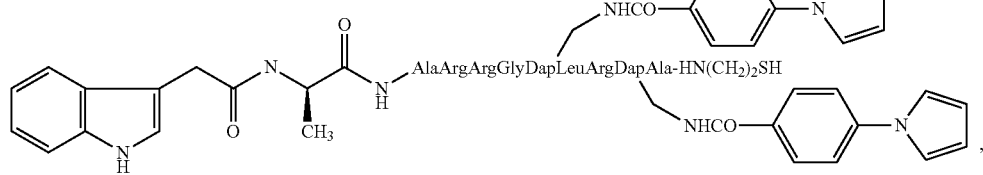
(SEQ ID NO: 2)

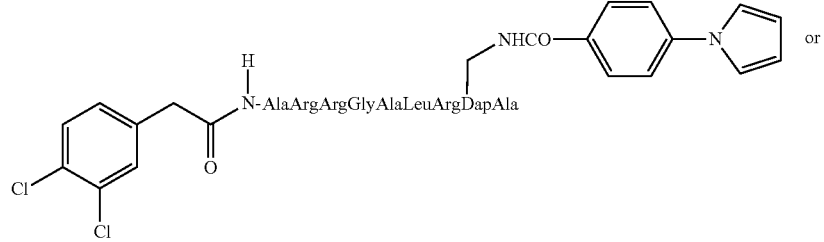
(SEQ ID NO: 2) or

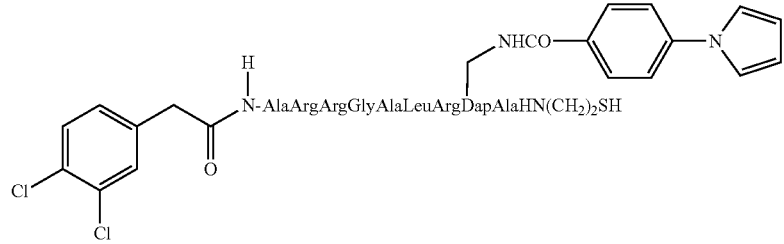
(SEQ ID NO: 2)

(See Example 1).

In other embodiments, the invention is directed to inhibitors of a protein kinase C (PKC). The inhibitor comprises (SEQ ID NO: 17)

$R_1$—N(H)—ArgArgGlnGlyDapPheMetTyrPhe-CONHCH$_2$CH$_2$SH,
with side chain: NH-R$_3$ attached via CH$_2$ to N bearing R$_2$ wherein $R_1$ and $R_3$ are independently H, Ac, a carboxylic acid from FIG. 4, or an aldehyde from FIG. 5, and $R_2$ is H, a carboxylic acid from FIG. 4, an aldehyde from FIG. 5, or nothing. In preferred embodiments, $R_1$ is Ac, H,

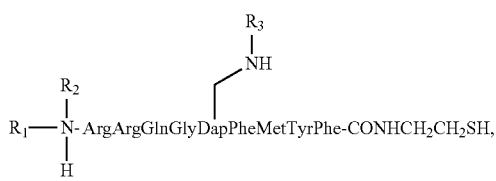, or 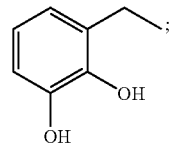;

$R_2$ is nothing, H or

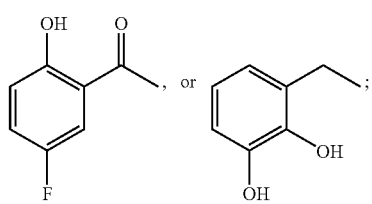

and $R_3$ is

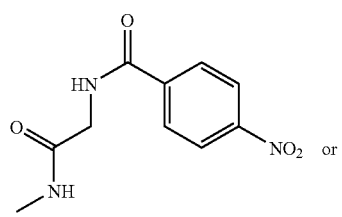 or

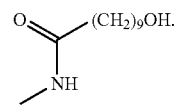

Figure 7:
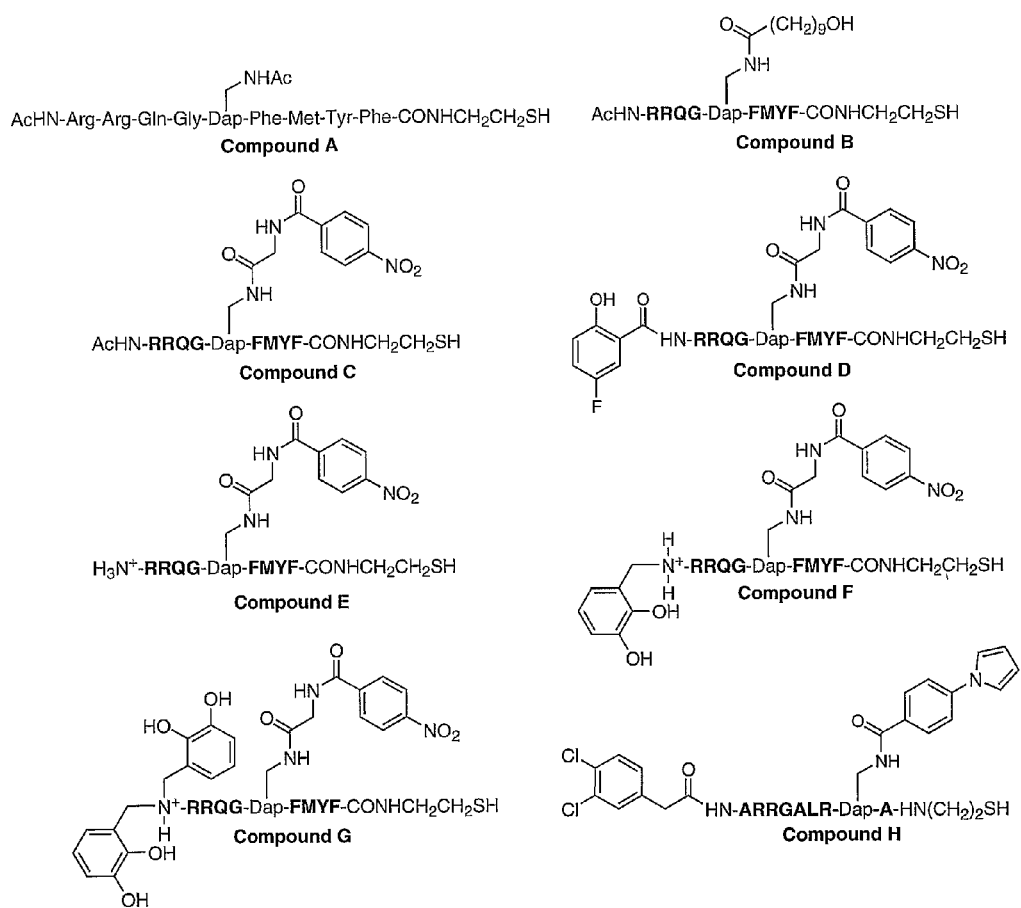
FIG. 7 shows control (compound A) and lead peptides (B-G) derived from libraries I-IV. Compound H was previously described (1).

More preferably, the inhibitor comprises Compound B, Compound C, Compound D, Compound E, Compound F, or Compound G of FIG. 7. Several of these inhibitors are specific for a particular PKC isoform (e.g., Compound F and Compound G of FIG. 7, which are specific for PKCδ and PKCζ, respectively, or a group of isoforms (e.g., Compound E, which is specific for PKCβI, PKCδ, and PKCζ). As used herein, an inhibitor is specific for a PKC isoform or group of isoforms if the inhibitor has an IC$_{50}$ for the PKC <0.1 that of all other of PKC isoforms α, βI, γ, δ, ε, θ, η, τ and ζ. Preferably, the inhibitor has an $IC_{50}$ for the PKC isoform <0.05 that of any other PKC isoform. More preferably, the inhibitor has an $IC_{50}$ for the PKC isoform <0.01 that of any other PKC isoform.

As with the PKCα inhibitors discussed above, any one or more than one of the amino acid moieties of these inhibitors can be a mimetic. Additionally, these inhibitors may further comprise constituents conjugated to any of the amino acid or mimetic moieties, as may be useful for detection, isolation, or quantitation of the inhibitor or its binding partners, such as PKCδ. Examples of such constituents include a His-6 moiety, a fluorescent moiety or a radioactive moiety.

Also as with the PKCα inhibitors, the inhibitors of these embodiments preferably have an $IC_{50}$<50 µM. The $IC_{50}$ for any of the invention inhibitors can be determined without undue experimentation, for example by the methods described in Examples 1 and 2. In more preferred embodiments, the inhibitor has an $IC_{50}$<10 µM; in even more preferred embodiments, the inhibitor has a PKCα $IC_{50}$<1 µM; in the most preferred embodiments, the inhibitor has an $IC_{50}$<0.1 µM.

Any of the above-described inhibitors can be formulated without undue experimentation for administration to a mammal, including humans, as appropriate for the particular application. Additionally, proper dosages of the inhibitor compositions can be determined without undue experimentation using standard dose-response protocols.

Accordingly, the inhibitor compositions designed for oral, lingual, sublingual, buccal and intrabuccal administration can be made without undue experimentation by means well known in the art, for example with an inert diluent or with an edible carrier. The inhibitor compositions may be enclosed in gelatin capsules or compressed into tablets. For the purpose of oral therapeutic administration, the inhibitor compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The inhibitor compositions of the present invention can easily be administered parenterally such as for example, by intravenous, intramuscular, intrathecal or subcutaneous injection. Parenteral administration can be accomplished by incorporating the inhibitor compositions into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical inhibitor compositions into the rectum or large intestine. This can be accomplished using suppositories or enemas. Suppository formulations can easily be made by methods known in the art. For example, suppository formulations can be prepared by heating glycerin to about 120° C., dissolving the inhibitor composition in the glycerin, mixing the heated glycerin after which purified water may be added, and pouring the hot mixture into a suppository mold.

Transdermal administration includes percutaneous absorption of the inhibitor composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the inhibitor composition to the mucous membranes of the nasal passage or nasal cavity of the patient. As used herein, pharmaceutical compositions for nasal administration of an inhibitor composition include therapeutically effective amounts of the composition prepared by well-known methods to be administered, for example, as a nasal spray, nasal drop, suspension, gel, ointment, cream or powder. Administration of the inhibitor composition may also take place using a nasal tampon or nasal sponge.

The above-identified protein kinase inhibitors were discovered using novel combinatorial libraries. These combinatorial libraries have the advantage of not requiring information about the structure of the active site of the enzyme.

Thus, the invention is also directed to combinatorial libraries useful for identifying an inhibitor of a protein kinase. The combinatorial libraries comprise a plurality of compounds, each compound comprising the following elements:

a consensus sequence for a substrate of the protein kinase, the consensus sequence comprising at least five amino acids or mimetics, wherein at least one amino acid or mimetic is not essential to substrate binding, and wherein an amino acid or mimetic not subject to phosphorylation substitutes a canonical Ser or Thr target residue in the consensus sequence; and a chemical moiety covalently bound to the compound at the at least one non-essential amino acid or mimetic in the consensus sequence and/or the amino acid or mimetic not subject to phosphorylation substituting the canonical Ser or Thr target residue. Each of the compounds in the combinatorial library comprises a different chemical moiety.

In preferred embodiments, the non-essential amino acid or mimetic and/or the amino acid or mimetic substituting a canonical Ser or Thr target residue is a diaminopropionic acid (Dap), because the various chemical moieties conjugated to the compound can be easily conjugated thereto, for example using a carboxyl or aldehyde derivative of the chemical moiety, which can be conjugated to the free amino group of the Dap by known methods.

However, other compounds can substitute for the non-essential amino acid and/or the amino acid or mimetic substituting a canonical Ser or Thr target residue, preferably compounds that allow convenient conjugation of the chemical moieties thereto.

In some embodiments, the chemical moiety conjugated to each compound is a carboxylic acid. See Example 1. Such carboxylic acids can, for example, be selected from any one of the carboxylic acids provided in FIG. 4.

In other embodiments, the chemical moiety conjugated to each compound is an aldehyde. See Example 2. Such aldehydes can, for example be selected from any of the aldehydes provided in FIG. 5.

Two or more chemical moieties can be conjugated to the consensus sequence portion of the compound. See, e.g., the above-described inhibitors for PKCδ and PKCζ, which contain one chemical moiety from a carboxylic acid and one from an aldehyde.

The chemical moieties are selected to add a diverse range of shapes and charges to the consensus sequence. For example, conjugating the carboxylic acid moiety to the consensus sequence to a Dap results in an amide bond, which is neutral under physiological conditions. By contrast, with aldehydes one obtains an alkylated amine, which is positively charged under physiological conditions.

The amino acid or mimetic not subject to phosphorylation that substitutes a canonical Ser or Thr target residue in the consensus sequence can comprise any amino acid or mimetic, whether natural or artificial. In preferred embodiments, this amino acid or mimetic is a Dap or an Ala.

These combinatorial libraries can be used to identify an inhibitor of any protein kinase from any species, including any eukaryote or virus. Preferably, the protein kinase is a mammalian protein kinase, such as a human protein kinase. Included are any types of protein kinases, such as serine/threonine-specific protein kinases (phosphorylase kinase, protein kinase A, protein kinase C, $Ca^{2+}$/calmodulin-dependent protein kinase, MAP kinase, and Mos/Raf kinase), tyrosine-specific protein kinases such as receptor tyrosine kinase, histidine-specific protein kinases, and aspartic acid/glutamic acid-specific protein kinases. In preferred embodiments, the protein kinase is a protein kinase C (PKC).

In some of these embodiments, the PKC is PKCα. Where the PKC is PKCα, a preferred consensus sequence comprises LysGlySerHyd(Arg/Lys) (SEQ ID NO:3), where Hyd is Phe, Leu or Ile. In those embodiments, a preferred consensus sequence having an Ala substituting for the canonical Ser or Thr target residue is AlaArgArgGlyAlaLeuArgGlnAla (SEQ ID NO:2).

In other embodiments, the protein kinase is PKCβI and the consensus sequence comprises ArgLysGlySerPheLys (SEQ ID NO:4); the protein kinase is PKCβII and the consensus sequence comprises ArgLysGlySerPheLys (SEQ ID NO:4); the protein kinase is PKCγ and the consensus sequence comprises ArgLysGlySerPheLys (SEQ ID NO:4); the protein kinase is PKCδ and the consensus sequence comprises (Lys/Gln)GlySerPhe(Phe/Met) (SEQ ID NO:5); the protein kinase is PKCε and the consensus sequence is Lys(Met/Lys)Ser(Phe/Ala)(Glu/Tyr/Asp/Phe) (SEQ ID NO:6); the protein kinase is PKCη and the consensus sequence is ArgArgSerPheArgArg (SEQ ID NO:7); the protein kinase is PKCζ and the consensus sequence is (Arg/Gln/Lys/Glu)(Met/Gly)Ser(Phe/Met)(Phe/Met) (SEQ ID NO:8); or the protein kinase is PKCμ and the consensus sequence is (Gln/Lys/Glu/Met)MetSer(Val/Met/Leu)(Ala/Met/Val) (SEQ ID NO:9).

In preferred embodiments, the combinatorial library comprises at least 10 compounds. More preferably, the combinatorial library comprises at least 50, or 100, or 200, or 300, or 400, or 500 compounds.

The invention is also directed to methods of identifying an inhibitor of a protein kinase. The methods comprise creating a combinatorial library as described above for the protein kinase, screening the compounds in the combinatorial library for inhibitory activity of the protein kinase, and identifying any compounds in the combinatorial library that are inhibitors of the protein kinase.

These methods can be used to identify an inhibitor of any eukaryotic or viral protein kinase now known or later discovered, including any mammalian, plant, insect, or protist protein kinase.

In preferred embodiments of these methods, two combinatorial libraries are created and screened for inhibitory activity. The first combinatorial library is created and used to identify a lead compound with some inhibitory activity. The second library is then created where all members have the chemical moiety of the lead compound and additional chemical moieties. As shown in Examples 1 and 2, this strategy can be successful in identifying potent inhibitors with high specificity.

The screening method can utilize any procedure known in the art for measuring inhibitory activity for the particular protein kinase. See, e.g., Example 1. The screening methods can also include a determination of the specificity of the inhibitory activity for any isoform of the protein kinase target, or for any other enzyme or bioactive compound. In preferred embodiments, specificity determinations are performed only on compounds that show sufficient inhibitory activity for the target protein kinase.

With these methods, the compounds can be screened separately. Alternatively, more than one inhibitor can be initially screened together, e.g., in batches, then the individual compounds from any batch that shows inhibitory activity are further tested.

Any of these methods can be adapted to automated or robotic procedures.

In preferred embodiments of these methods, the protein kinase is a protein kinase C (PKC), for example PKCα, a PKCδ, or a PKCζ0.

Protein kinases are known to be involved in various deleterious conditions, for example, various cancers, various cardiovascular diseases, type 2 diabetes, agammaglobulinaemia, reperfusion injury, Alzheimer's disease, various neurological and neurodegenerative diseases, chemotherapy-induced alopecia, arthritis, various autoimmune diseases, various inflammatory diseases, allergies, asthma and viral virulence (Inagaki et al., 2003; Wang et al., 2003; Lahn et al., 2003, 2004; Neid et al. 2003; Vetrie et al., 1993; Stenberg et al., 2000; Munger and Roizman, 2001; U.S. Pat. Nos. 6,248,559; 6,214,852; 6,660,731). Therefore, the administration of inhibitors described herein to mammals having or at risk for such deleterious conditions would be expected to be useful treatments for those conditions.

Thus, the present invention is additionally directed to methods of treating a deleterious condition in a mammal, where the condition is dependent on a protein kinase for induction or severity. The methods comprise contacting the mammal with an inhibitor of the protein kinase found by the above-described methods of identifying an inhibitor of the protein kinase.

In preferred embodiments of these methods, the protein kinase is a protein kinase C (PKC). Where the protein kinase is PKCα, the preferred inhibitor comprises A-Ala-Arg-Arg-X—B-Hyd-C-D- (SEQ ID NO:1), where A=AcHN—,

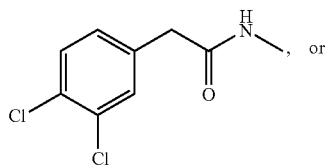

, or

15

-continued

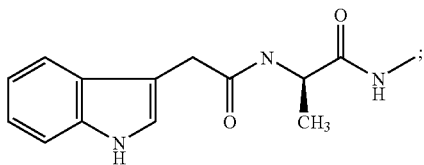

X=any amino acid or amino acid mimetic; B=Ala or a diaminopropionic acid (Dap) derivative having the formula

16

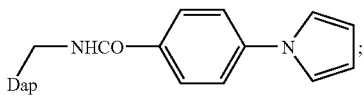

Hyd=Phe, Leu or Ile; U=Arg or Lys; and D=Ala or a Dap derivative having the formula

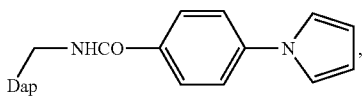

wherein any of the amino acids can alternatively be an analogous amino acid mimetic.

Preferred examples of such inhibitors are (SEQ ID NO: 2)
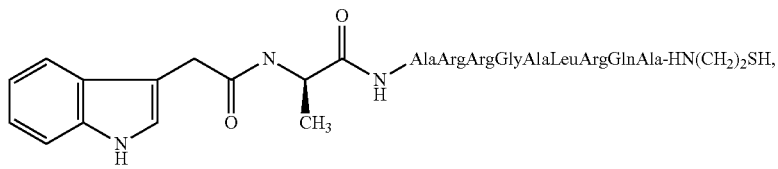

(SEQ ID NO: 2)
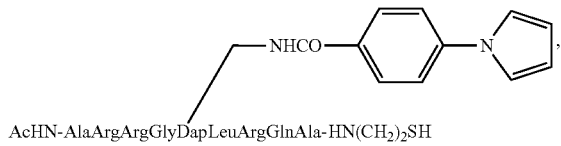

(SEQ ID NO: 2)
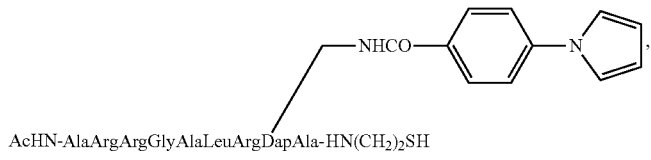

(SEQ ID NO: 2)
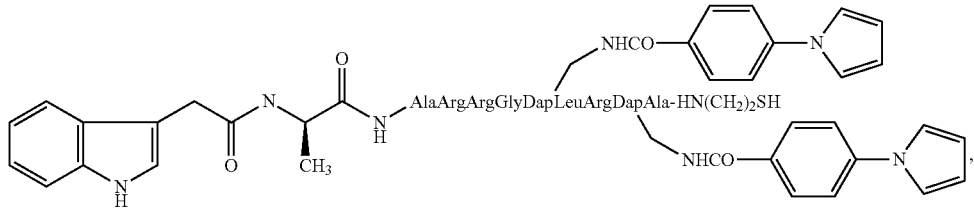

(SEQ ID NO: 2)
 and

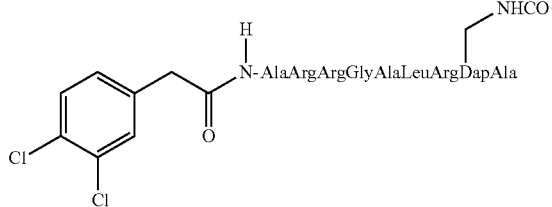

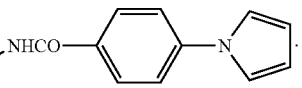
(SEQ ID NO: 2)

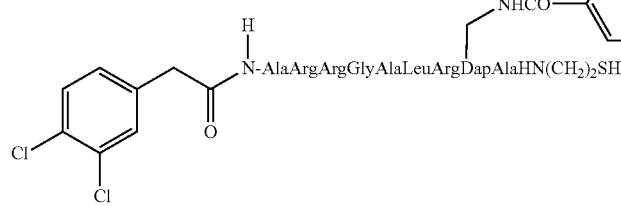

Where the protein kinase is PKCδ, a preferred inhibitor is

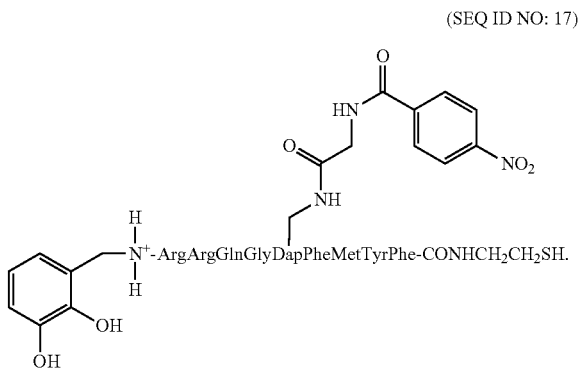
(SEQ ID NO: 17)

Additionally, where the protein kinase is PKCζ, a preferred inhibitor is

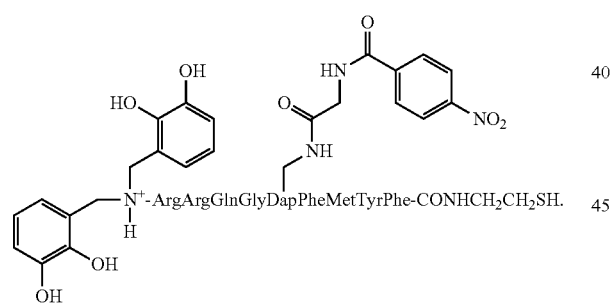
(SEQ ID NO: 17)

In any of these embodiments, the inhibitor is preferably in a pharmaceutically acceptable excipient, as previously described.

The deleterious condition can be any condition that is dependent on a protein kinase for induction or severity. Preferred examples include cancer, cardiovascular disease, type 2 diabetes, agammaglobulinaemia, reperfusion injury, Alzheimer's disease, neurological or neurodegenerative disease, chemotherapy-induced alopecia, arthritis, autoimmune disease, inflammatory disease, allergies, asthma and viral virulence. In more preferred embodiments, the deleterious condition is a cancer, a cardiovascular disease, or type 2 diabetes.

These methods are useful for treatment of any mammal, for example a rodent or a human.

The present invention is also directed to methods of inhibiting a protein kinase. The methods comprise contacting the protein kinase with an inhibitor of the protein kinase identified by the methods of identifying an inhibitor of a protein kinase described above. These methods could be used to inhibit a protein kinase that is isolated, or, preferably, in a living mammalian cell. Where the protein kinase is in a living cell, the cell can be in culture or in a living mammal, such as a rodent or a human. Such a mammal can additionally have a deleterious condition that is dependent on the protein kinase for induction or severity. As discussed above, such deleterious conditions include various cancers, various cardiovascular diseases, type 2 diabetes, agammaglobulinaemia, reperfusion injury, Alzheimer's disease, various neurological and neurodegenerative diseases, chemotherapy-induced alopecia, arthritis, various autoimmune diseases, various inflammatory diseases, allergies, asthma and viral virulence. include cancer, heart disease or type 2 diabetes. In more preferred embodiments, the deleterious condition is a cancer, a cardiovascular disease, or type 2 diabetes.

In preferred embodiments, the protein kinase is a protein kinase C (PKC). Where the protein kinase is PKCα, the inhibitor preferably comprises A-Ala-Arg-Arg-X—B-Hyd-C-D- (SEQ ID NO:1), where A=AcHN—,

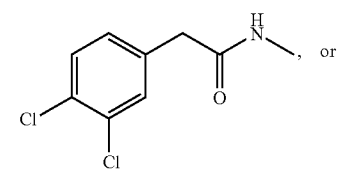

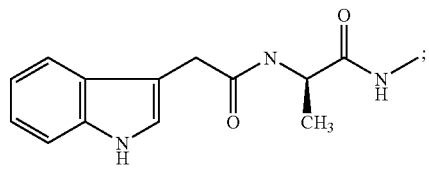

X=any amino acid or amino acid mimetic; B=Ala or a diaminopropionic acid (Dap) derivative having the formula

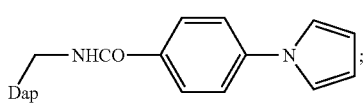

Hyd=Phe, Leu or Ile; C=Arg or Lys; and D=Ala or a Dap derivative having the formula

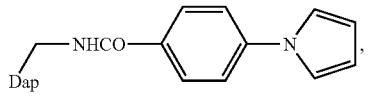
wherein any of the amino acids can alternatively be an analogous amino acid mimetic.
Preferred examples of such inhibitors include,
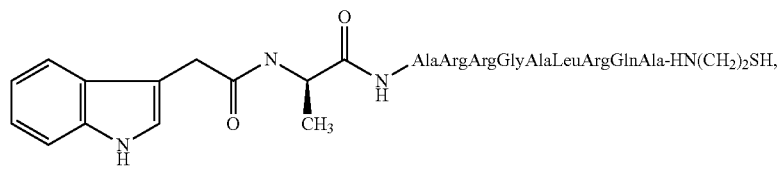 (SEQ ID NO: 2)
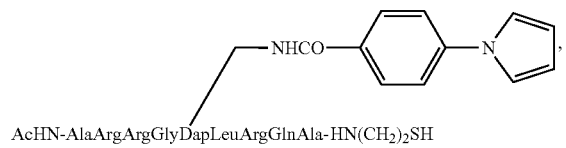 (SEQ ID NO: 2)
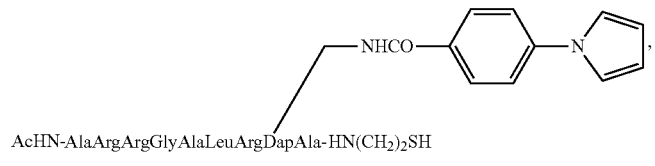 (SEQ ID NO: 2)
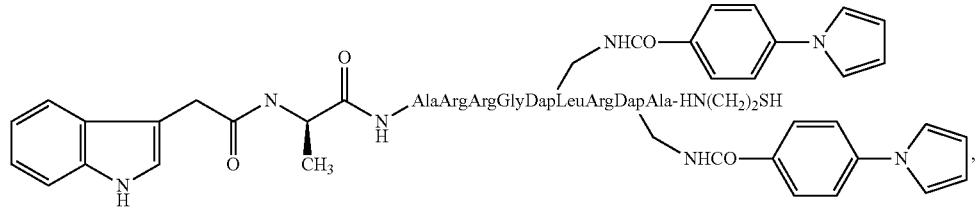 (SEQ ID NO: 2)
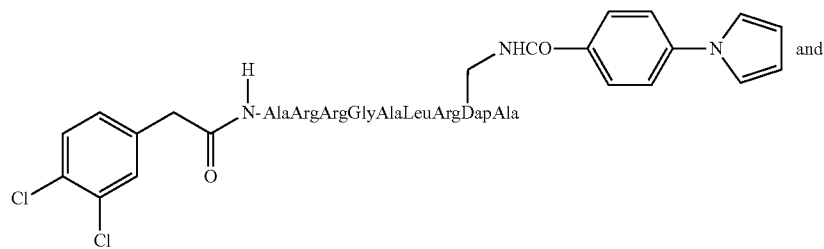 (SEQ ID NO: 2)
and
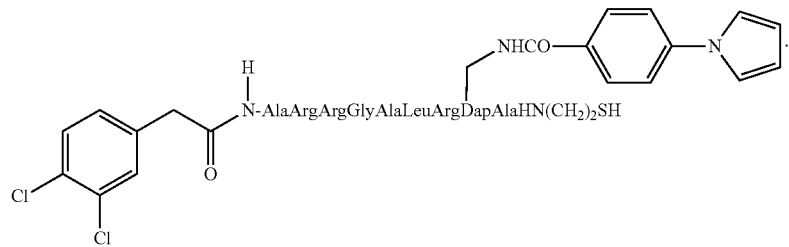 (SEQ ID NO: 2)
Where the protein kinase is a PKCδ, the inhibitor is preferably (SEQ ID NO: 17)

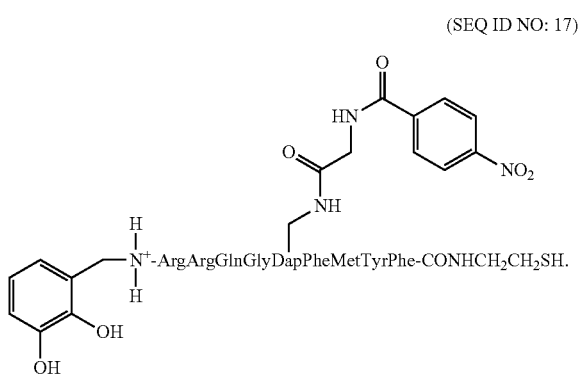

Where the protein kinase is PKCζ, the inhibitor is preferably (SEQ ID NO: 17)

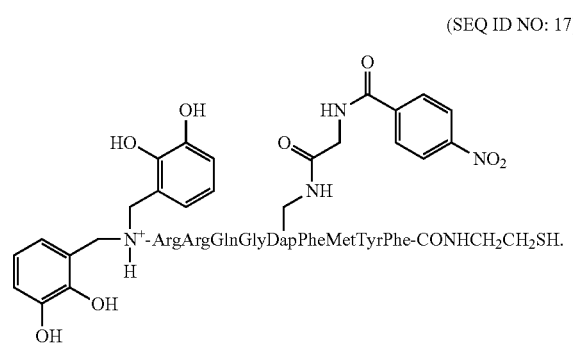

In additional embodiments, the invention is directed to the use of an inhibitor of a protein kinase in the manufacture of a medicament for the treatment of a deleterious condition in a mammal that is dependent on a protein kinase for induction or severity. The treatment comprises contacting the mammal with an inhibitor of the protein kinase identified by the methods of identifying an inhibitor of a protein kinase described above.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Inhibitors of Protein Kinase Cα and Methods of Identifying Those Inhibitors

Example Summary

A potent and highly selective inhibitor of protein kinase Cα has been generated via the combinatorial modification of a consensus sequence peptide. The inhibitor displays a $K_i$ of 800 pM versus variable peptide substrate and good selectivity versus other members of the PKC family, including PKCβ (385-fold), PKCγ (580-fold), PKCδ (2730-fold); PKCε (600-fold), PKCη (1310-fold), PKCθ (1210-fold), PKCτ (940-fold), and PKCζ (640-fold). The parallel synthesis strategy employed is easily automated and straightforward to implement.

Introduction

We describe herein a library-based strategy that transforms consensus sequences into high affinity ligands in the absence of any tertiary structural information of the protein target. We chose PKCα for our initial studies, an enzyme that is a recognized chemotherapeutic target for several malignant disorders (Nakashima, 2002). The structure of PKCα is not known. A variety of peptide-based inhibitors have been described, the very best of which display $IC_{50}$ or $K_i$ values in the high nM to low μM range, usually using PKC mixtures (Borowski et al., 2000; Ward et al., 1995; Eichholtz et al., 1993; O'Brian and Ward, 1989; Ricouart et al., 1989; Charp et al., 1988; House and Kemp, 1987). The consensus substrate sequence for PKCα is -Arg-Arg-Lys-Gly-Ser-Hyd-Arg- (where Hyd=Phe/Leu/Ile/) (Nishikawa et al., 1997) (SEQ ID NO:10). We designed the closely analogous nonphosphorylatable peptide Ala-Arg-Arg-Gly-Ala-Leu-Arg-Gln-Ala (SEQ ID NO:2), in which the Ser residue is replaced by Ala. Previous studies have demonstrated that the Arg residues and the hydrophobic amino acid at P-1 promote PKCα recognition (Nishikawa et al., 1997). Consequently, these critical residues were retained and we sought to identify high affinity replacements for presumed nonessential residues or regions on the consensus peptide. In the absence of the 3-dimensional structure of the target protein, three distinct sites on the peptide framework were chosen for the introduction of molecular diversity (libraries I-III [FIG. 1]). For example, a peptide containing (L)-2,3-diaminopropionic acid (Dap) at the former Ala position was synthesized, distributed in equal amounts to individual wells of eight 96 well plates, and then acylated with one of 720 different carboxylic acids to create library II. Analogous libraries I and III were constructed as well. Following Dap acylation, the side chain protecting groups were removed with trifluoroacetic acid and the peptide then cleaved from the resin with assay buffer (which contains dithiothreitol). The peptide solutions were filtered into deep well plates, stored, and subsequently evaluated for inhibitory potency using a previously described radioactive assay (See Materials and Methods).

Figure 2:
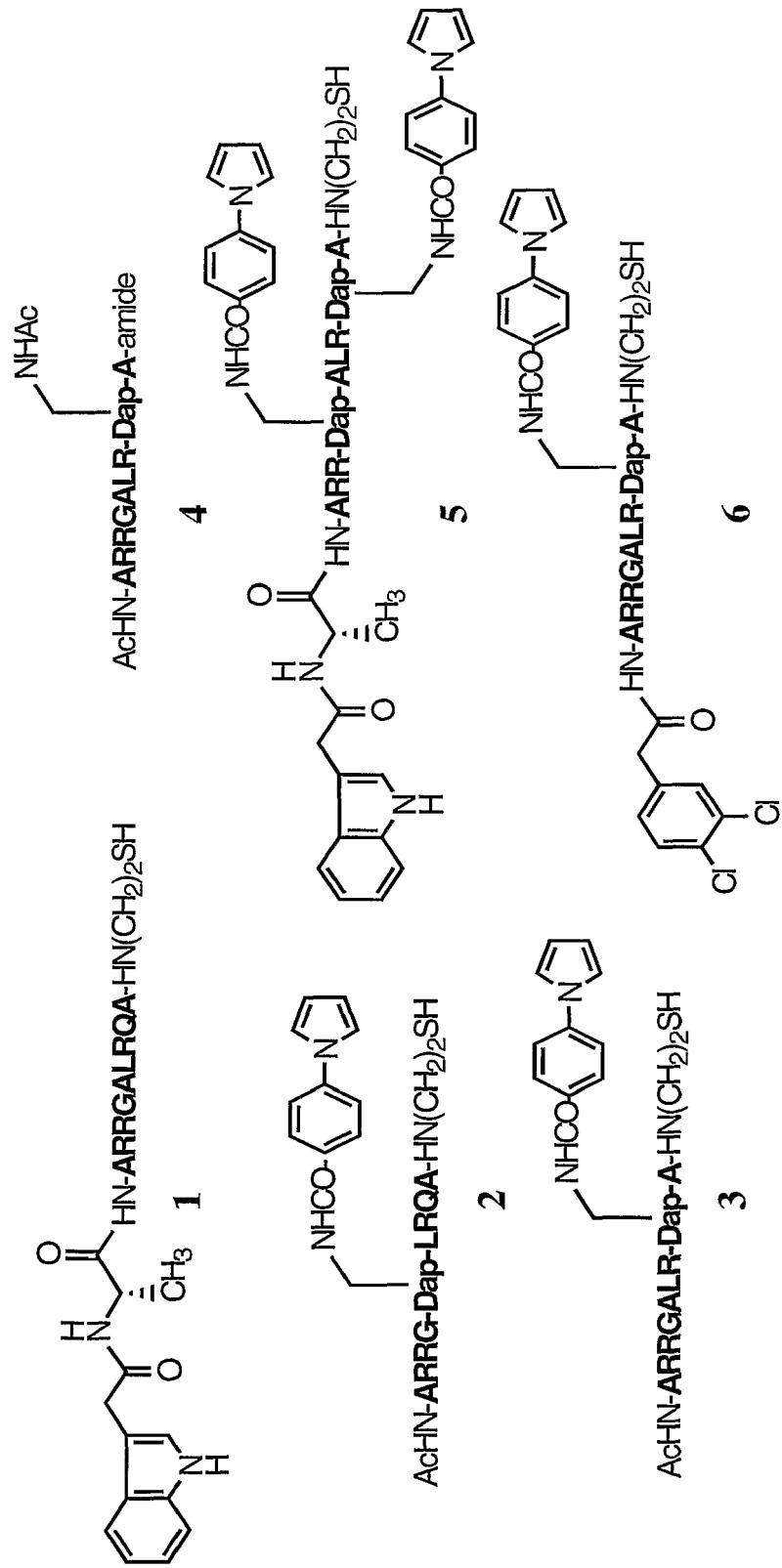
FIG. 2 shows various compounds used in PKCα inhibitor studies.

Leads (1-3) from the three libraries are depicted in FIG. 2. All three compounds display several orders of magnitude improvement in inhibitory efficacy relative to the diacetylated control peptide 4 (Table 1). Interestingly, the best leads from libraries II (Compound 2, Table 1) and III (Compound 3) contain the same substituent, a 4-pyrrole phenylacyl moiety. The latter result suggests that PKC(X possesses a binding pocket that displays a special affinity for this substituent. Given the weak inhibitory activity displayed by peptide 4, it is likely that the peptide backbones of 2 and 3 are not rigidly held by the PKCα surface, but rather assume unique enzyme-bound conformations that promote insertion of the 4-pyrrole phenylacyl into a high affinity pocket. Indeed, peptide 5, which contains the three substituents identified from libraries I, II, and III, displays an inhibitory potency similar to that of the individual peptide leads 2 and 3. This result is consistent with the notion that there exists a single 4-pyrrole phenylacyl docking site within the substrate-binding region of PKCα. This result also highlights one of the potential pitfalls associated with combining, in a single molecule, lead substituents obtained independently of one another.

TABLE 1

PKCα inhibitory potencies of compounds 1-6. $K_i$ values were obtained by varying peptide substrate concentration.

| Compound | $IC_{50}$ (μM) | $K_i$ (μM) |
| --- | --- | --- |
| 1 | 10.4 ± 2.1 | not determined |
| 2 | 5.7 ± 0.4 | not determined |
| 3 | 4.7 ± 0.8 | 0.55 ± 0.07 |
| 4 | 1100 ± 210 | 350 ± 80 |
| 5 | 3.1 ± 0.7 | not determined |
| 6 | 0.0019 ± 0.0002 | 0.00080 ± 0.00025 |

Figure 3:
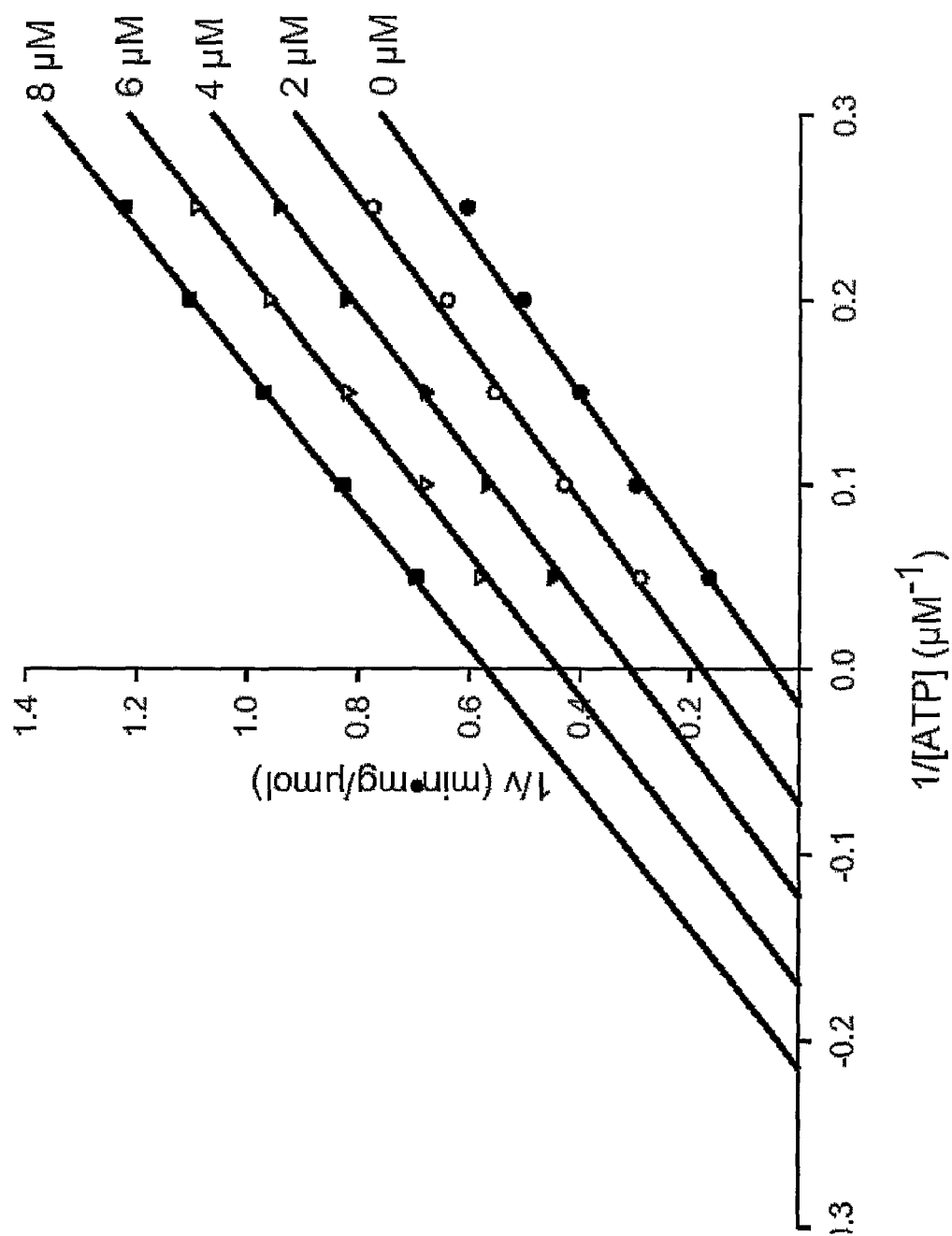
FIG. 3 is a graph of the inhibition pattern of compound 3 versus variable [ATP].
Figure 4A:
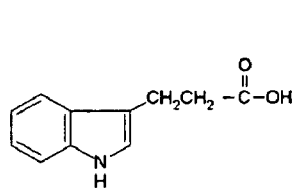
FIG. 4A-4Z and FIG. 4AA-4JJ shows 720 carboxylic acid moieties used in exemplified invention combinatorial libraries.
Figure 4A:
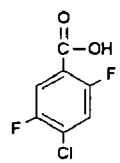
Figure 4A:
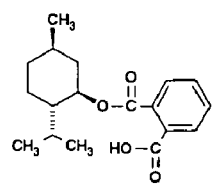
Figure 4A:
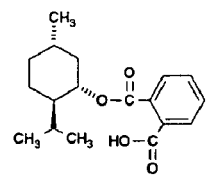
Figure 4A:
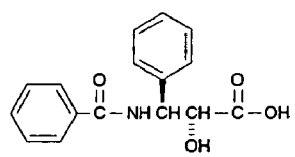
Figure 4A:
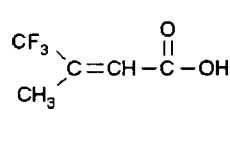
Figure 4A:
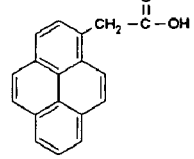
Figure 4A:
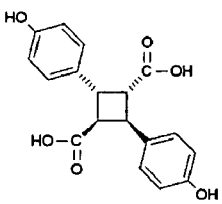
Figure 4A:
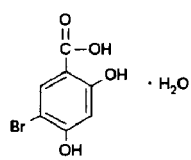
Figure 4A:
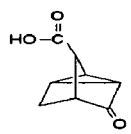
Figure 4A:
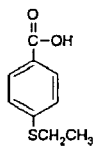
Figure 4A:
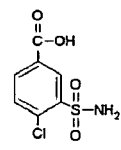
Figure 4A:
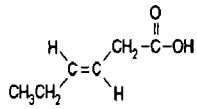
Figure 4A:
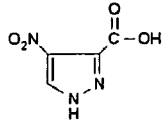
Figure 4A:
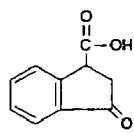
Figure 4A:
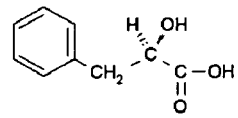
Figure 4A:
Figure 4A:
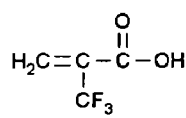
Figure 4A:
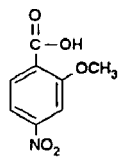
Figure 4A:
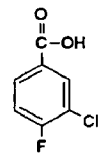
Figure 4B:
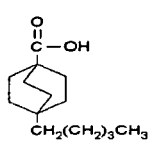
Figure 4B:
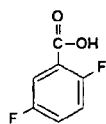
Figure 4B:
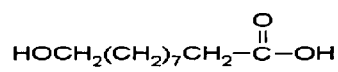
Figure 4B:
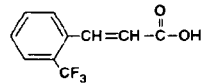
Figure 4B:
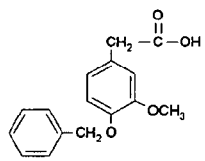
Figure 4B:
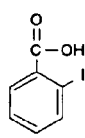
Figure 4B:
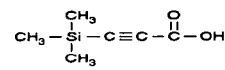
Figure 4B:
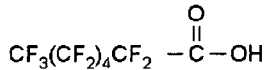
Figure 4B:
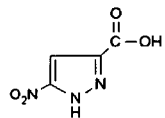
Figure 4B:
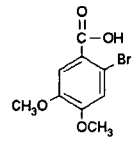
Figure 4B:
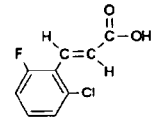
Figure 4B:
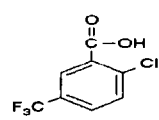
Figure 4B:
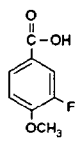
Figure 4B:
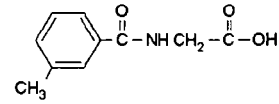
Figure 4B:
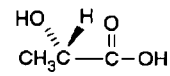
Figure 4B:
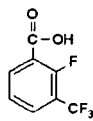
Figure 4B:
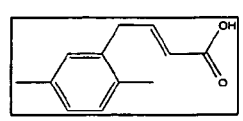
Figure 4B:
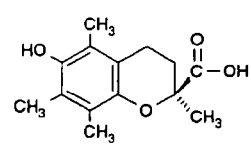
Figure 4B:
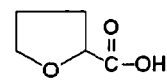
Figure 4C:
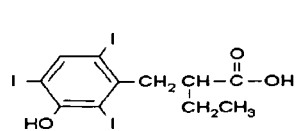
Figure 4C:
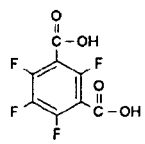
Figure 4C:
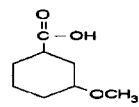
Figure 4C:
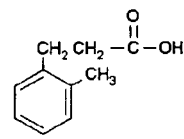
Figure 4C:
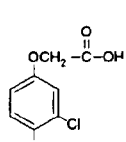
Figure 4C:
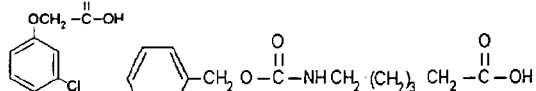
Figure 4C:
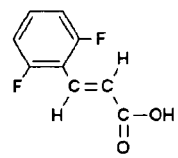
Figure 4C:
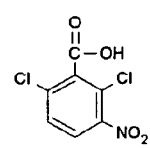
Figure 4C:
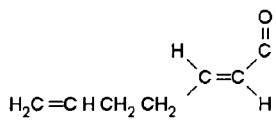
Figure 4C:
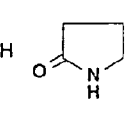
Figure 4C:
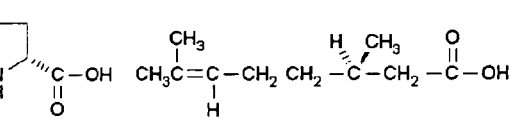
Figure 4C:
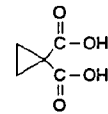
Figure 4C:
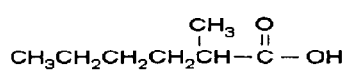
Figure 4C:
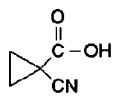
Figure 4C:
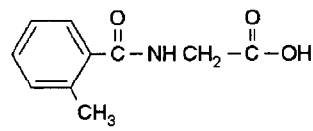
Figure 4C:
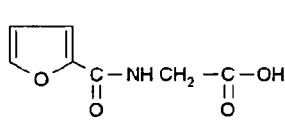
Figure 4C:
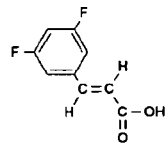
Figure 4C:
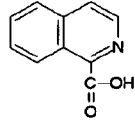
Figure 4C:
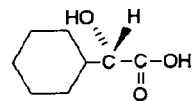
Figure 4D:
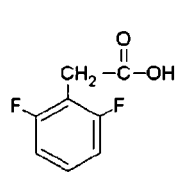
Figure 4D:
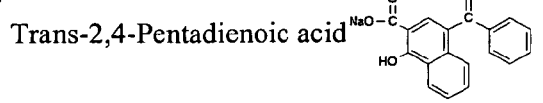
Figure 4D:
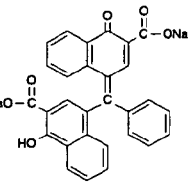
Figure 4D:
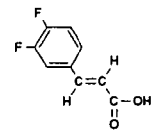
Figure 4D:
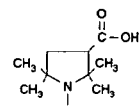
Figure 4D:
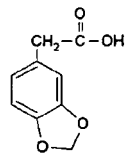
Figure 4D:
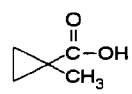
Figure 4D:
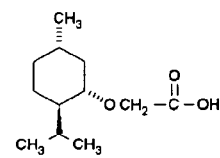
Figure 4D:
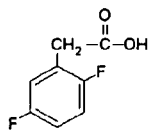
Figure 4D:
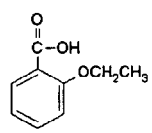
Figure 4D:
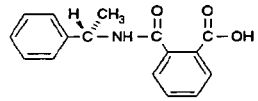
Figure 4D:
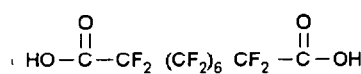
Figure 4D:
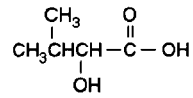
Figure 4D:
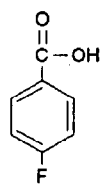
Figure 4D:
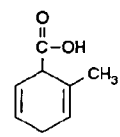
Figure 4D:
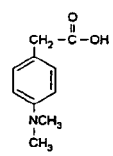
Figure 4D:
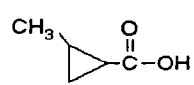
Figure 4D:
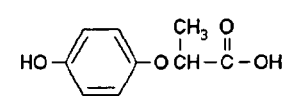
Figure 4D:
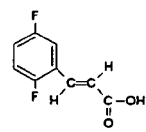
Figure 4F:
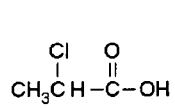
Figure 4F:
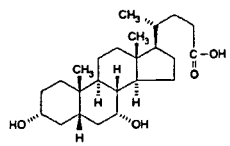
Figure 4F:
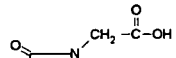
Figure 4F:
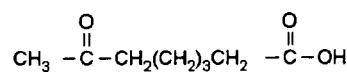
Figure 4F:
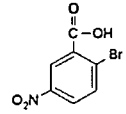
Figure 4F:
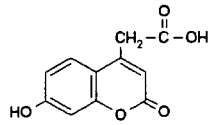
Figure 4F:
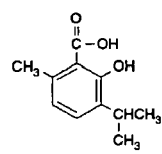
Figure 4F:
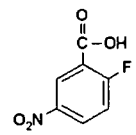
Figure 4F:
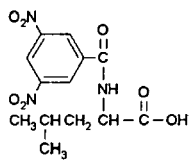
Figure 4F:
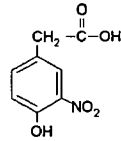
Figure 4F:
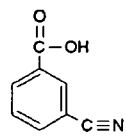
Figure 4F:
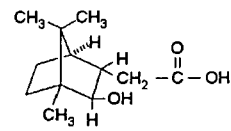
Figure 4F:
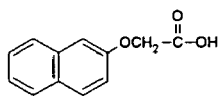
Figure 4F:
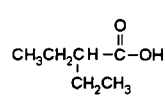
Figure 4F:
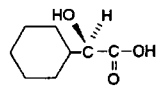
Figure 4F:
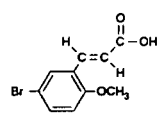
Figure 4F:
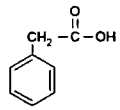
Figure 4F:
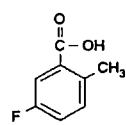
Figure 4F:
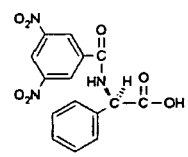
Figure 4G:
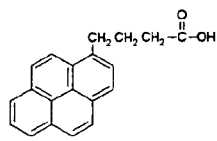
Figure 4G:
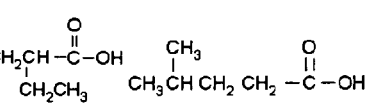
Figure 4G:
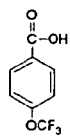
Figure 4G:
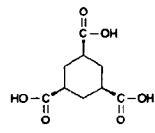
Figure 4G:
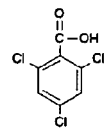
Figure 4G:
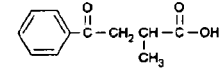
Figure 4G:
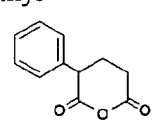
Figure 4G:
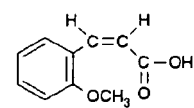
Figure 4G:
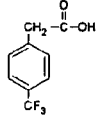
Figure 4G:
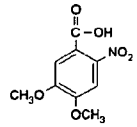
Figure 4G:
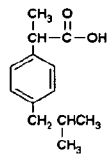
Figure 4G:
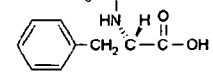
Figure 4G:
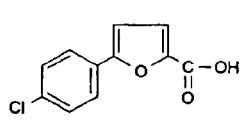
Figure 4G:
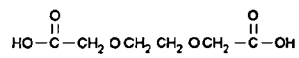
Figure 4G:
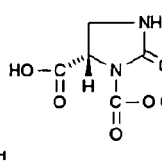
Figure 4G:
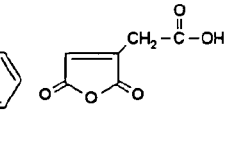
Figure 4I:
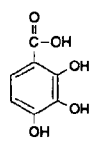
Figure 4I:
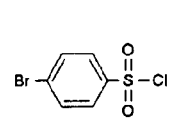
Figure 4I:
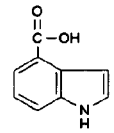
Figure 4I:
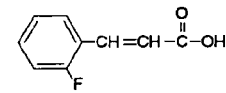
Figure 4I:
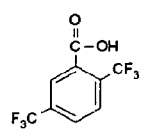
Figure 4I:
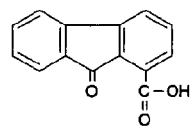
Figure 4I:
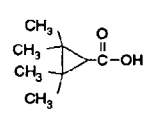
Figure 4I:
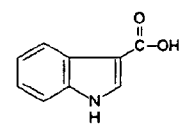
Figure 4I:
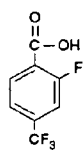
Figure 4I:
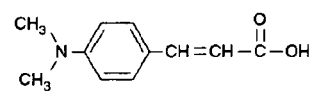
Figure 4I:
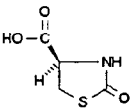
Figure 4I:
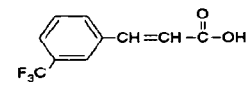
Figure 4I:
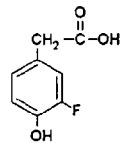
Figure 4I:
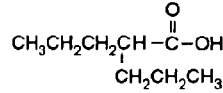
Figure 4I:
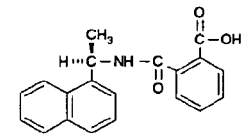
Figure 4I:
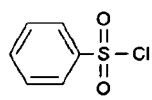
Figure 4I:
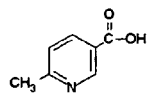
Figure 4I:
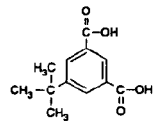
Figure 4I:
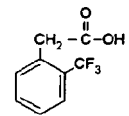
Figure 4K:
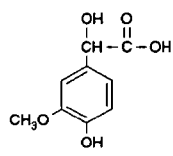
Figure 4K:
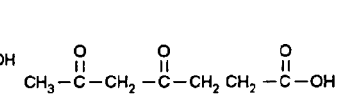
Figure 4K:
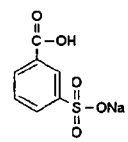
Figure 4K:
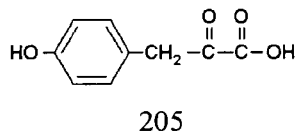
Figure 4K:
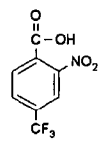
Figure 4K:
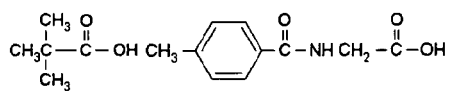
Figure 4K:
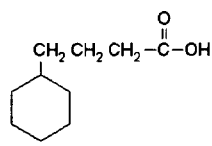
Figure 4K:
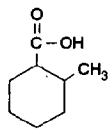
Figure 4K:
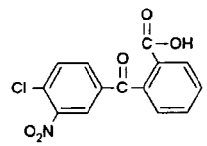
Figure 4K:
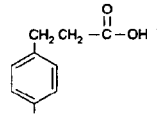
Figure 4K:
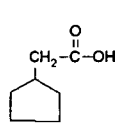
Figure 4K:
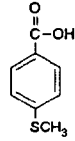
Figure 4K:
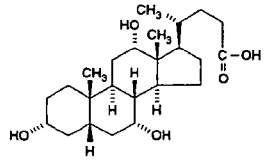
Figure 4K:
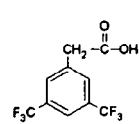
Figure 4K:
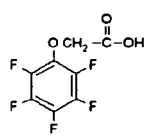
Figure 4K:
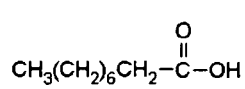
Figure 4K:
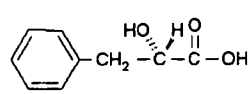
Figure 4K:
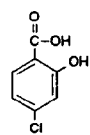
Figure 4L:
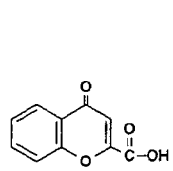
Figure 4L:
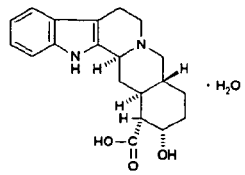
Figure 4L:
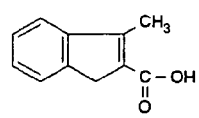
Figure 4L:
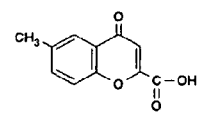
Figure 4L:
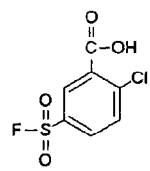
Figure 4L:
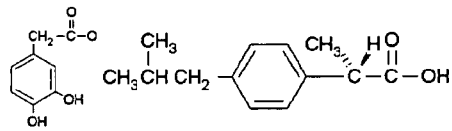
Figure 4L:
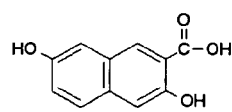
Figure 4L:
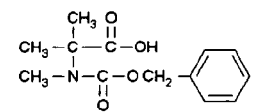
Figure 4L:
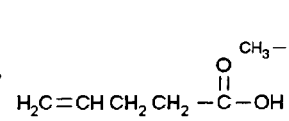
Figure 4L:
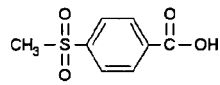
Figure 4L:
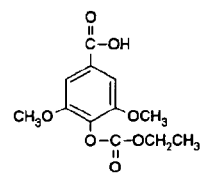
Figure 4L:
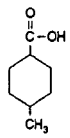
Figure 4L:
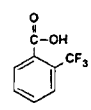
Figure 4L:
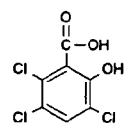
Figure 4L:
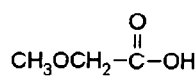
Figure 4L:
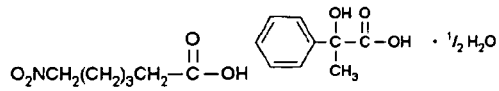
Figure 4M:
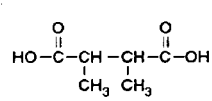
Figure 4M:
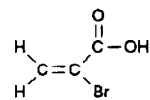
Figure 4M:
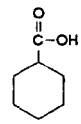
Figure 4M:
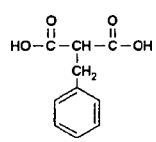
Figure 4M:
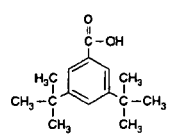
Figure 4M:
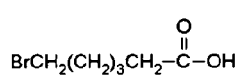
Figure 4M:
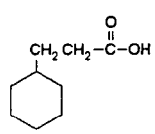
Figure 4M:
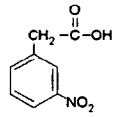
Figure 4M:
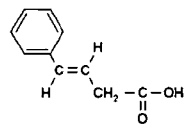
Figure 4M:
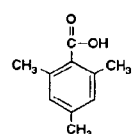
Figure 4M:
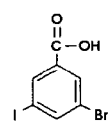
Figure 4M:
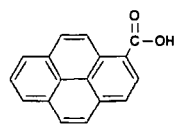
Figure 4M:
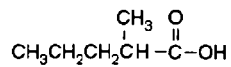
Figure 4M:
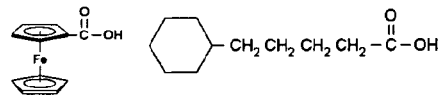
Figure 4M:
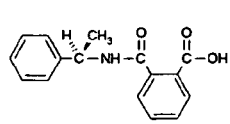
Figure 4M:
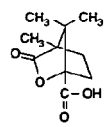
Figure 4M:
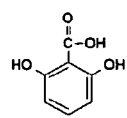
Figure 4M:
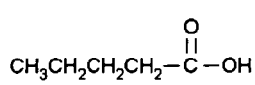
Figure 4O:
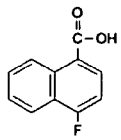
Figure 4O:
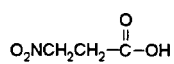
Figure 4O:
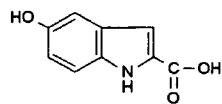
Figure 4O:
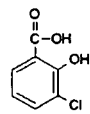
Figure 4O:
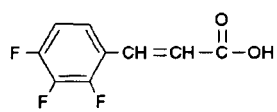
Figure 4O:
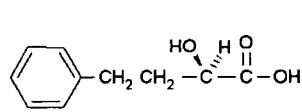
Figure 4O:
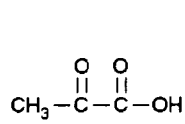
Figure 4O:
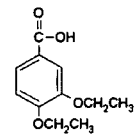
Figure 4O:
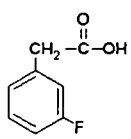
Figure 4O:
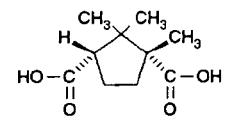
Figure 4O:
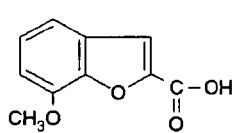
Figure 4O:
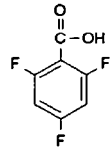
Figure 4O:
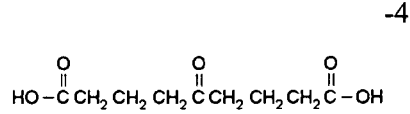
Figure 4O:
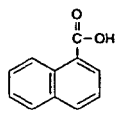
Figure 4O:
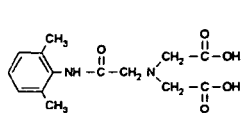
Figure 4O:
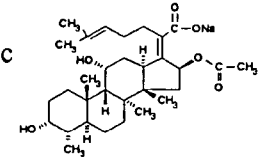
Figure 4Q:
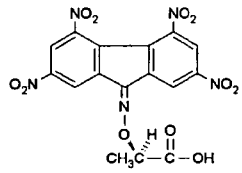
Figure 4Q:
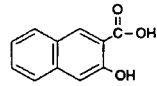
Figure 4Q:
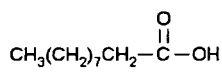
Figure 4Q:
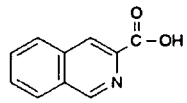
Figure 4Q:
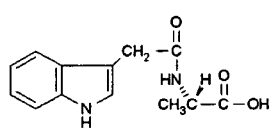
Figure 4Q:
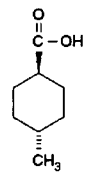
Figure 4Q:
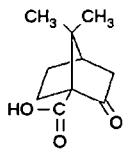
Figure 4Q:
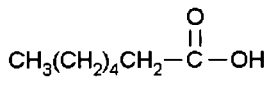
Figure 4Q:
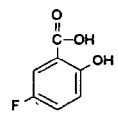
Figure 4Q:
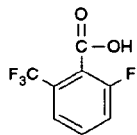
Figure 4Q:
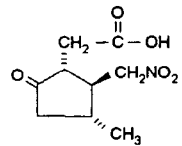
Figure 4Q:
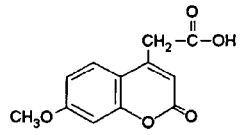
Figure 4Q:
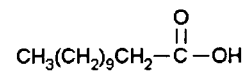
Figure 4Q:
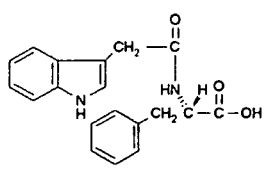
Figure 4Q:
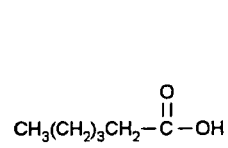
Figure 4Q:
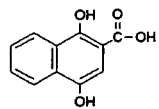
Figure 4R:
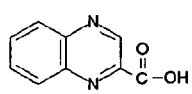
Figure 4R:
Figure 4R:
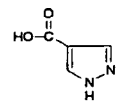
Figure 4R:
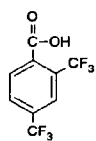
Figure 4R:
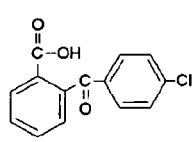
Figure 4R:
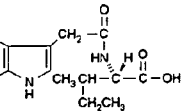
Figure 4R:
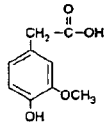
Figure 4R:
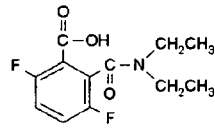
Figure 4R:
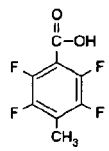
Figure 4R:
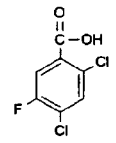
Figure 4R:
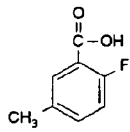
Figure 4R:
Figure 4R:
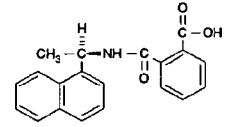
Figure 4R:
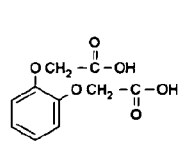
Figure 4R:
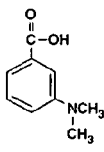
Figure 4R:
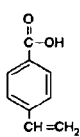
Figure 4R:
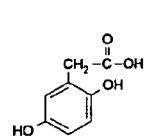
Figure 4S:
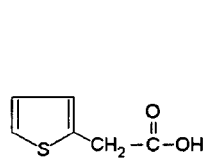
Figure 4S:
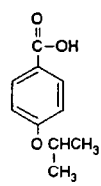
Figure 4S:
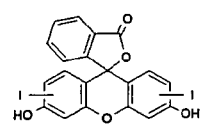
Figure 4S:
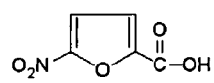
Figure 4S:
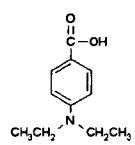
Figure 4S:
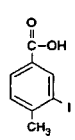
Figure 4S:
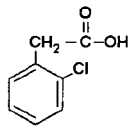
Figure 4S:
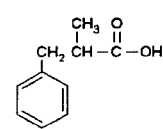
Figure 4S:
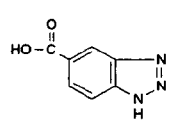
Figure 4S:
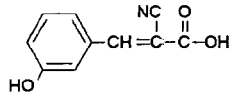
Figure 4S:
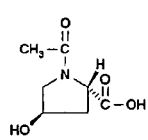
Figure 4S:
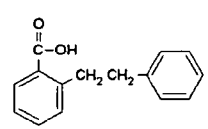
Figure 4S:
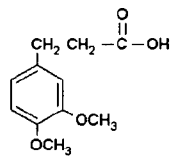
Figure 4S:
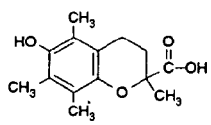
Figure 4S:
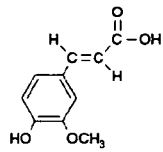
Figure 4S:
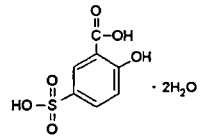
Figure 4S:
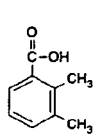
Figure 4S:
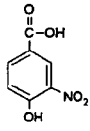
Figure 4S:
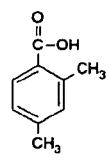
Figure 4U:
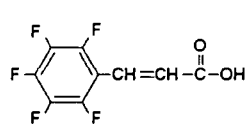
Figure 4U:
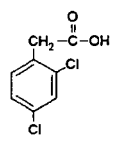
Figure 4U:
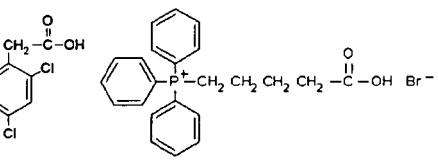
Figure 4U:
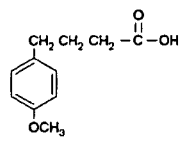
Figure 4U:
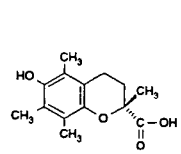
Figure 4U:
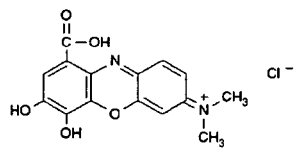
Figure 4U:
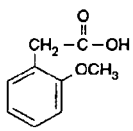
Figure 4U:
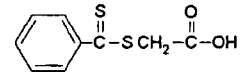
Figure 4U:
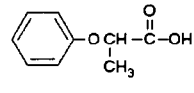
Figure 4U:
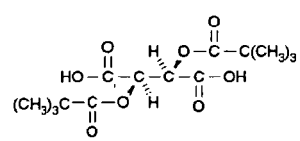
Figure 4U:
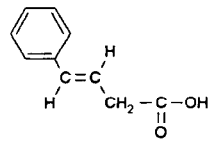
Figure 4U:
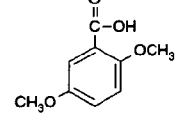
Figure 4U:
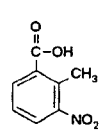
Figure 4U:
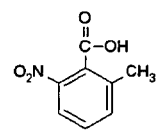
Figure 4U:
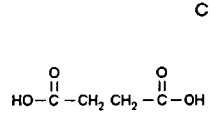
Figure 4U:
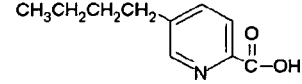
Figure 4U:
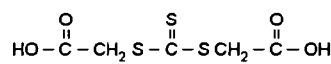
Figure 4U:
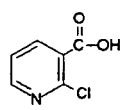
Figure 4U:
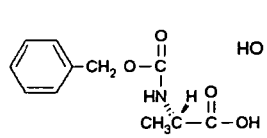
Figure 4U:
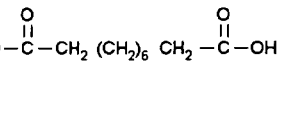
Figure 4V:
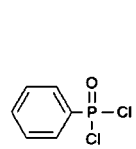
Figure 4V:
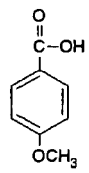
Figure 4V:
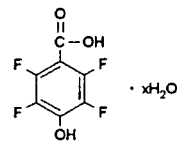
Figure 4V:
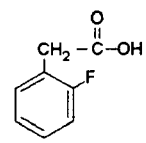
Figure 4V:
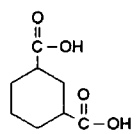
Figure 4V:
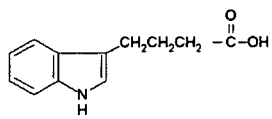
Figure 4V:
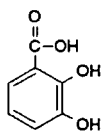
Figure 4V:
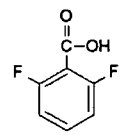
Figure 4V:
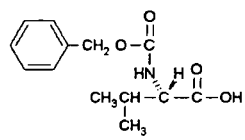
Figure 4V:
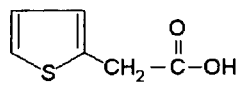
Figure 4V:
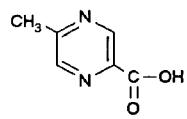
Figure 4V:
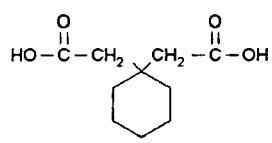
Figure 4V:
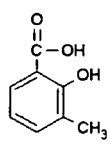
Figure 4V:
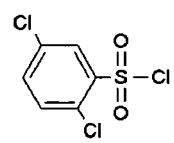
Figure 4V:
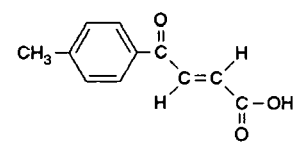
Figure 4V:
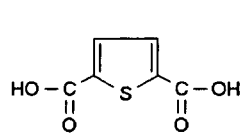
Figure 4V:
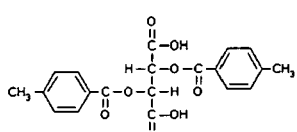
Figure 4V:
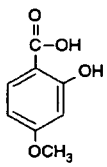
Figure 4V:
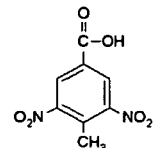
Figure 4W:
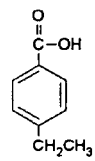
Figure 4W:
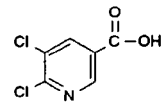
Figure 4W:
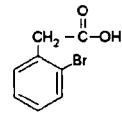
Figure 4W:
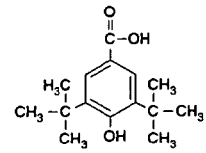
Figure 4W:
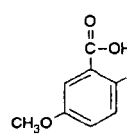
Figure 4W:
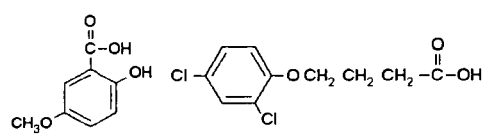
Figure 4W:
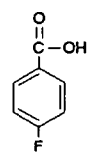
Figure 4W:
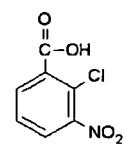
Figure 4W:
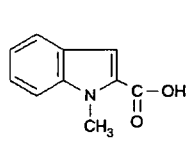
Figure 4W:
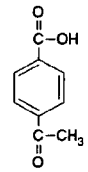
Figure 4W:
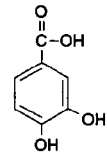
Figure 4W:
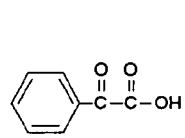
Figure 4W:
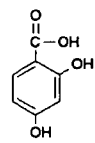
Figure 4W:
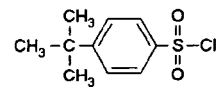
Figure 4W:
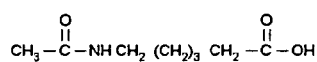
Figure 4W:
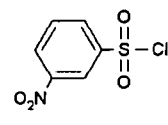
Figure 4W:
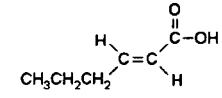
Figure 4X:
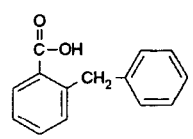
Figure 4X:
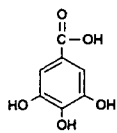
Figure 4X:
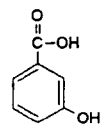
Figure 4X:
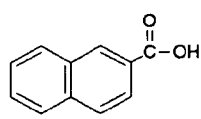
Figure 4X:
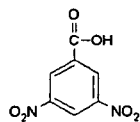
Figure 4X:
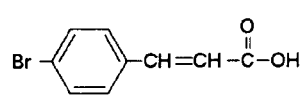
Figure 4X:
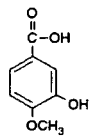
Figure 4X:
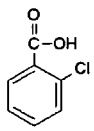
Figure 4X:
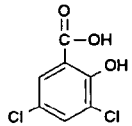
Figure 4X:
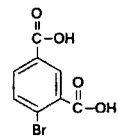
Figure 4X:
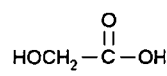
Figure 4X:
Figure 4X:
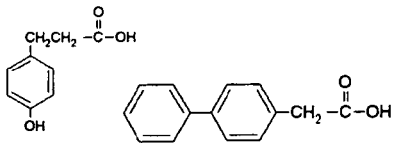
Figure 4X:
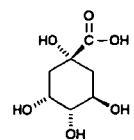
Figure 4X:
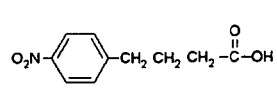
Figure 4X:
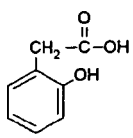
Figure 4Y:
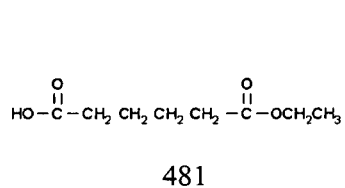
Figure 4Y:
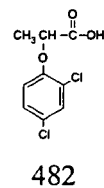
Figure 4Y:
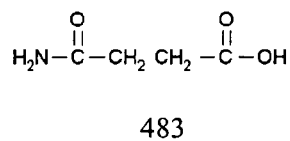
Figure 4Y:
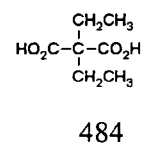
Figure 4Y:
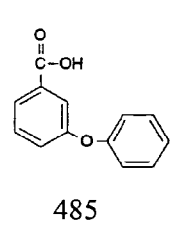
Figure 4Y:
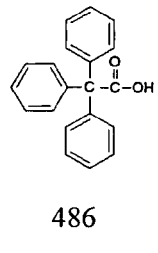
Figure 4Y:
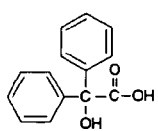
Figure 4Y:
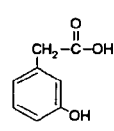
Figure 4Y:
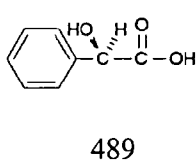
Figure 4Y:
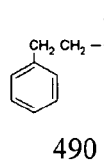
Figure 4Y:
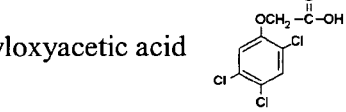
Figure 4Y:
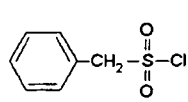
Figure 4Y:
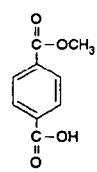
Figure 4Y:
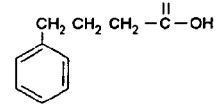
Figure 4Y:
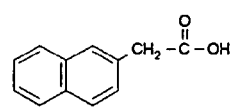
Figure 4Y:
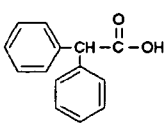
Figure 4Y:
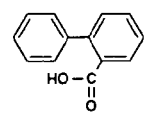
Figure 4Z:
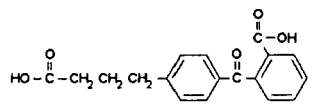
Figure 4Z:
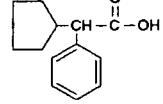
Figure 4Z:
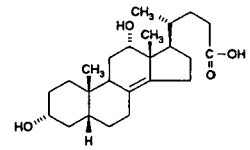
Figure 4Z:
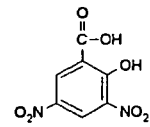
Figure 4Z:
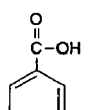
Figure 4Z:
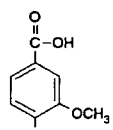
Figure 4Z:
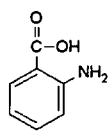
Figure 4Z:
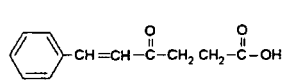
Figure 4Z:
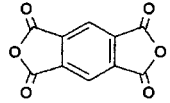
Figure 4Z:
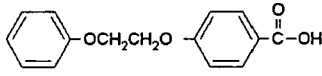
Figure 4Z:
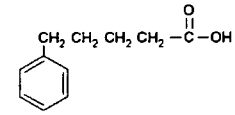
Figure 4Z:
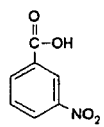
Figure 4Z:
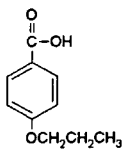
Figure 4Z:
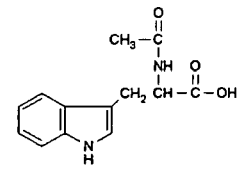
Figure 4Z:
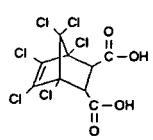
Figure 4Z:
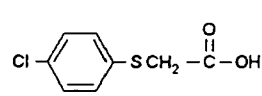
Figure 4Z:
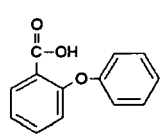
Figure 4Z:
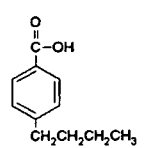
Figure 4A:
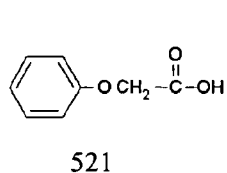
Figure 4A:
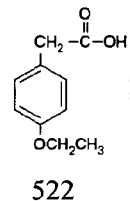
Figure 4A:
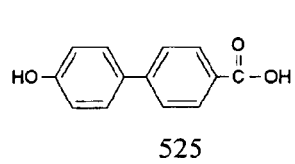
Figure 4A:
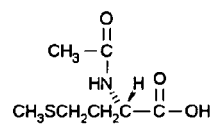
Figure 4A:
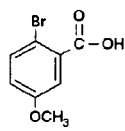
Figure 4A:
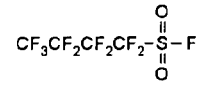
Figure 4A:
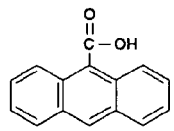
Figure 4A:
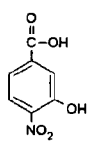
Figure 4A:
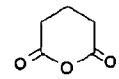
Figure 4A:
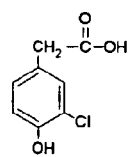
Figure 4A:
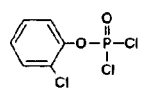
Figure 4A:
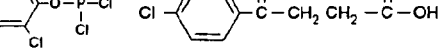
Figure 4A:
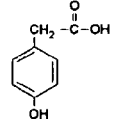
Figure 4A:
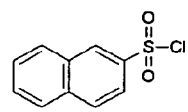
Figure 4A:
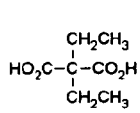
Figure 4A:
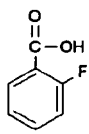
Figure 4A:
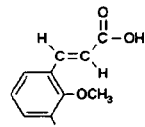
Figure 4B:
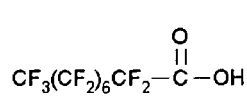
Figure 4B:
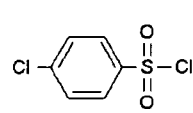
Figure 4B:
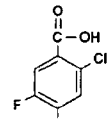
Figure 4B:
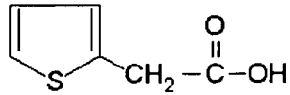
Figure 4B:
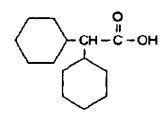
Figure 4B:
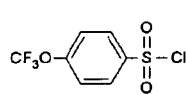
Figure 4B:
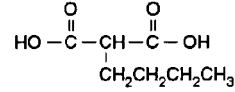
Figure 4B:
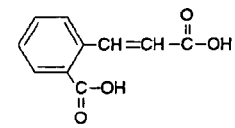
Figure 4B:
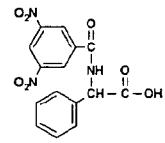
Figure 4B:
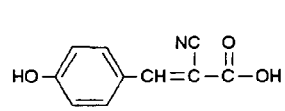
Figure 4B:
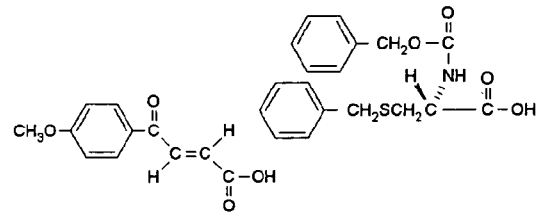
Figure 4B:
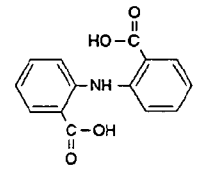
Figure 4B:
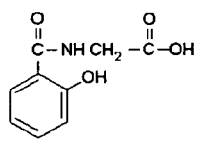
Figure 4B:
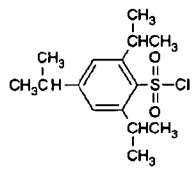
Figure 4B:
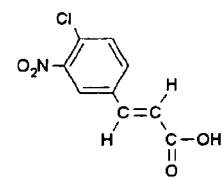
Figure 4B:
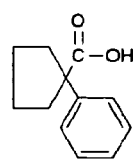
Figure 4B:
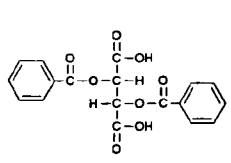
Figure 4B:
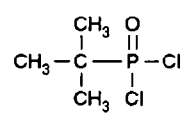
Figure 4C:
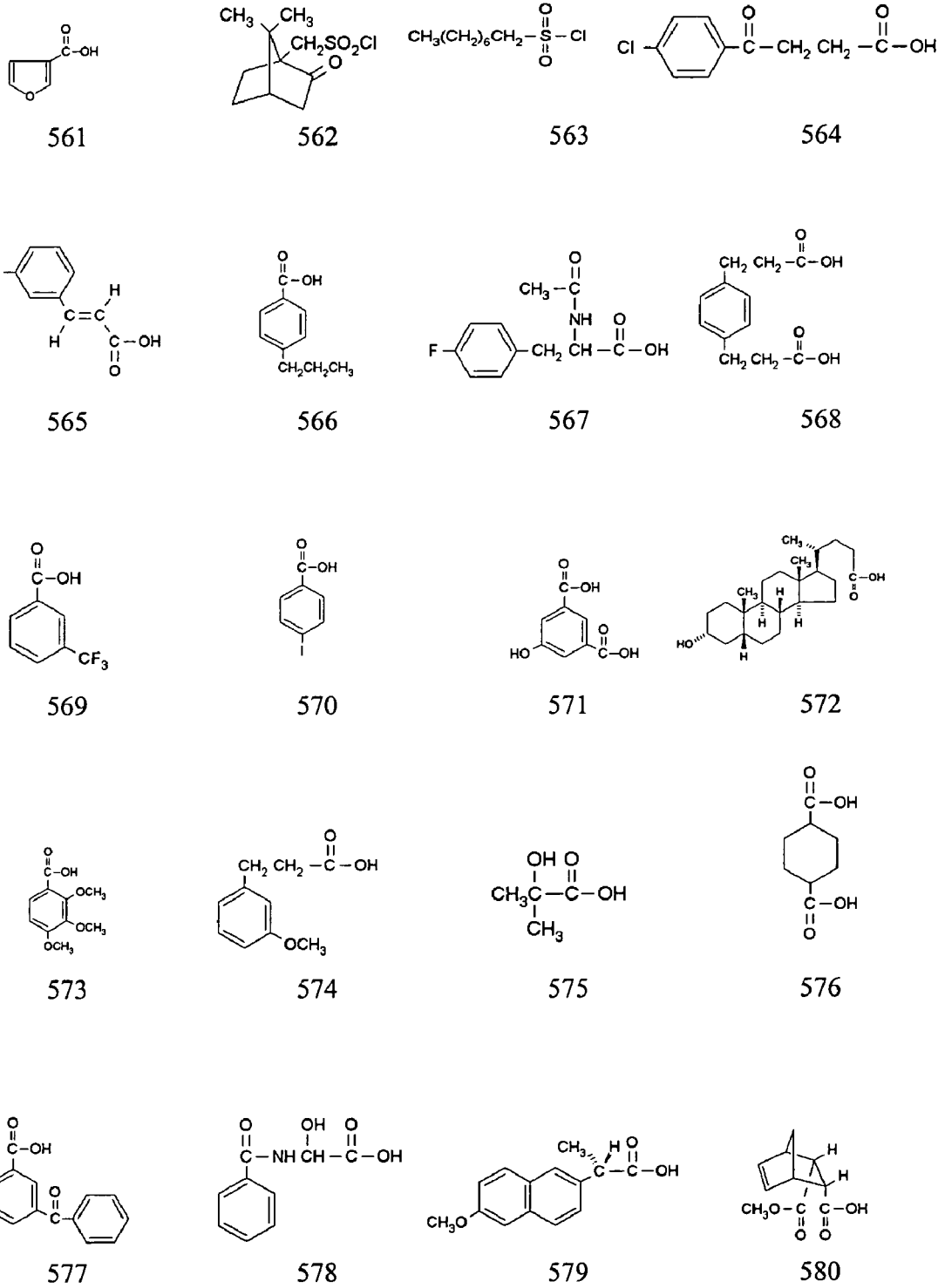
Figure 4D:
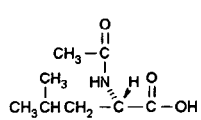
Figure 4D:
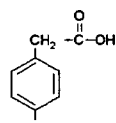
Figure 4D:
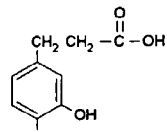
Figure 4D:
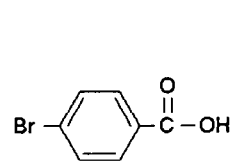
Figure 4D:
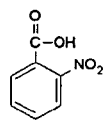
Figure 4D:
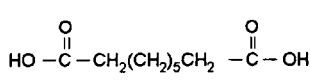
Figure 4D:
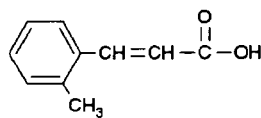
Figure 4D:
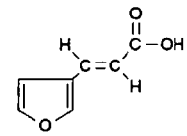
Figure 4D:
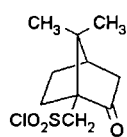
Figure 4D:
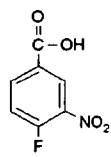
Figure 4D:
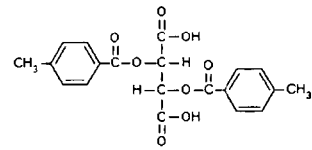
Figure 4D:
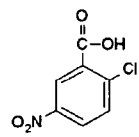
Figure 4D:
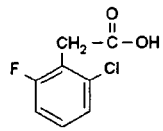
Figure 4D:
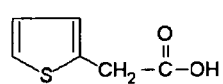
Figure 4D:
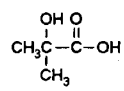
Figure 4D:
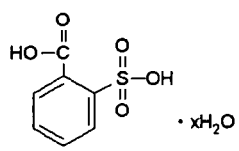
Figure 4D:
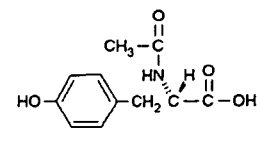
Figure 4D:
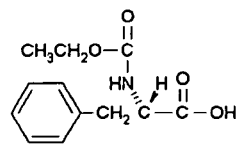
Figure 4F:
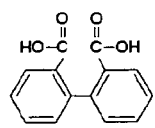
Figure 4F:
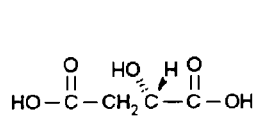
Figure 4F:
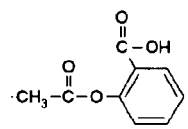
Figure 4F:
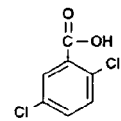
Figure 4F:
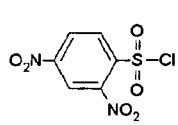
Figure 4F:
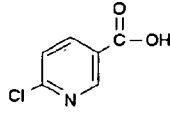
Figure 4F:
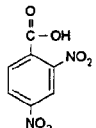
Figure 4F:
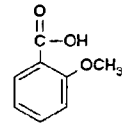
Figure 4F:
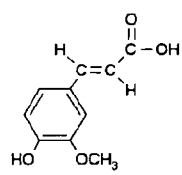
Figure 4F:
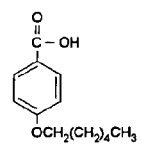
Figure 4F:
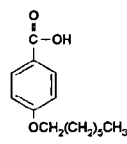
Figure 4F:
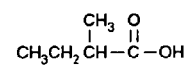
Figure 4F:
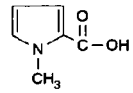
Figure 4F:
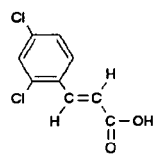
Figure 4F:
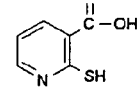
Figure 4F:
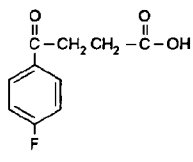
Figure 4F:
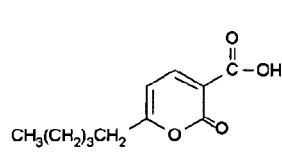
Figure 4F:
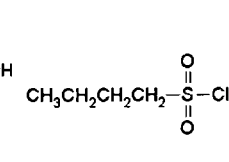
Figure 4F:
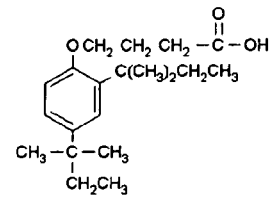
Figure 4G:
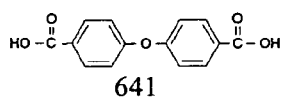
Figure 4G:
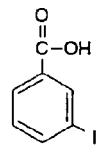
Figure 4G:
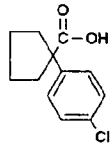
Figure 4G:
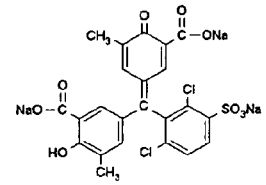
Figure 4G:
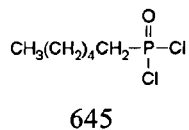
Figure 4G:
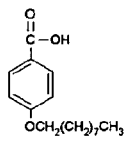
Figure 4G:
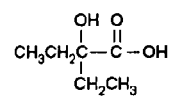
Figure 4G:
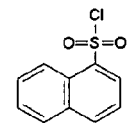
Figure 4G:
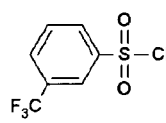
Figure 4G:
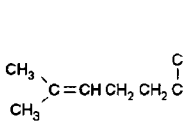
Figure 4G:
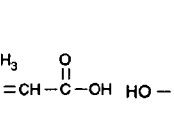
Figure 4G:
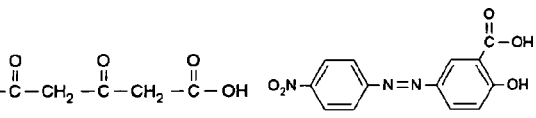
Figure 4G:
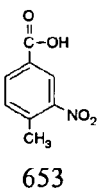
Figure 4G:
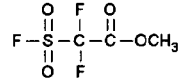
Figure 4G:
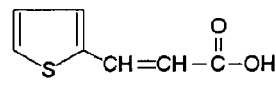
Figure 4G:
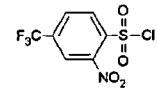
Figure 4G:
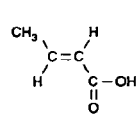
Figure 4G:
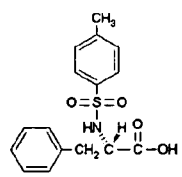
Figure 4G:
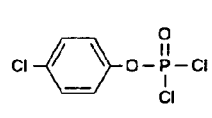
Figure 4G:
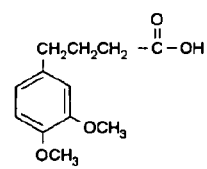
Figure 4H:
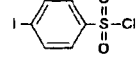
Figure 4H:
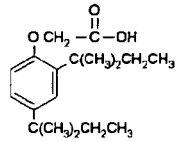
Figure 4H:
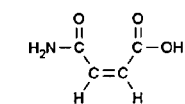
Figure 4H:
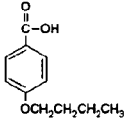
Figure 4H:
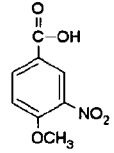
Figure 4H:
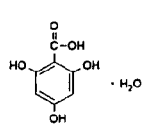
Figure 4H:
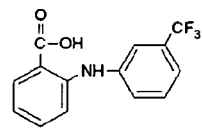
Figure 4H:
Figure 4H:
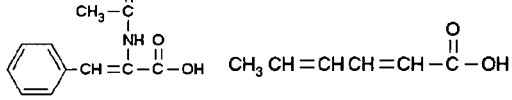
Figure 4H:
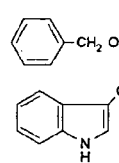
Figure 4H:
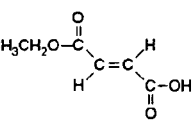
Figure 4H:
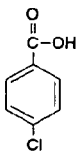
Figure 4H:
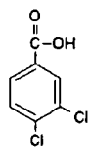
Figure 4H:
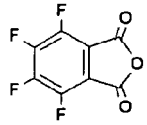
Figure 4H:
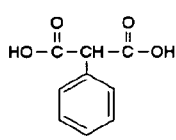
Figure 4H:
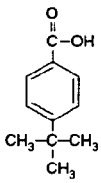
Figure 4H:
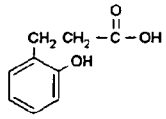
Figure 4H:
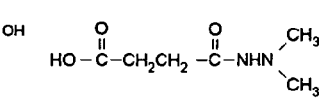
Figure 4H:
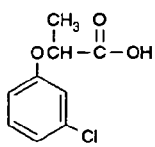
Figure 4I:
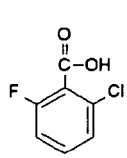
Figure 4I:
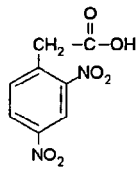
Figure 4I:
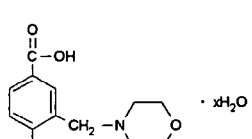
Figure 4I:
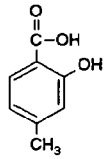
Figure 4I:
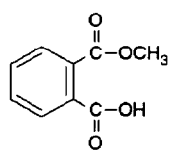
Figure 4I:
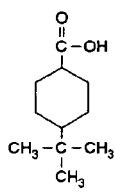
Figure 4I:
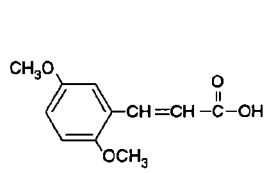
Figure 4I:
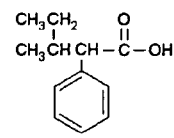
Figure 4I:
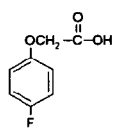
Figure 4I:
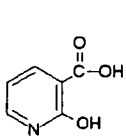
Figure 4I:
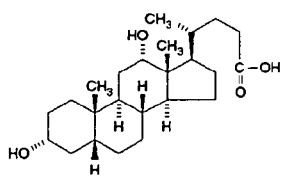
Figure 4I:
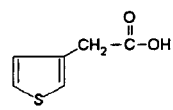
Figure 4I:
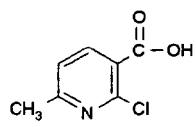
Figure 4I:
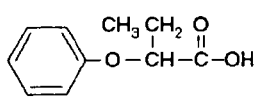
Figure 4I:
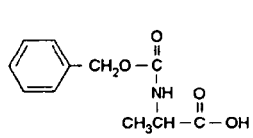
Figure 4I:
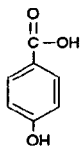
Figure 4I:
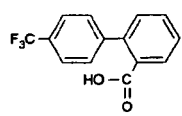
Figure 4J:
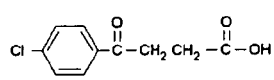
Figure 4J:
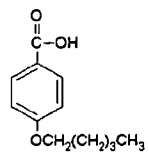
Figure 4J:
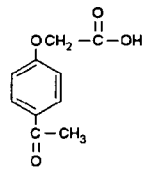
Figure 4J:
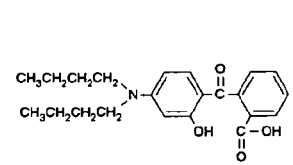
Figure 4J:
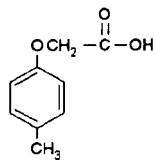
Figure 4J:
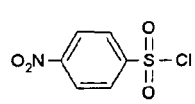
Figure 4J:
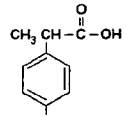
Figure 4J:
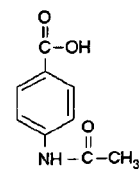
Figure 4J:
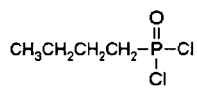
Figure 4J:
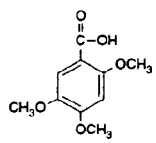
Figure 4J:
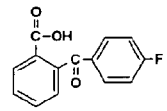
Figure 4J:
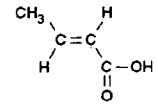
Figure 4J:
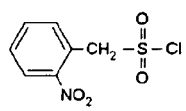
Figure 4J:
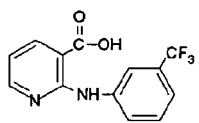
Figure 4J:
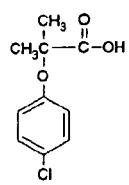
Figure 4J:
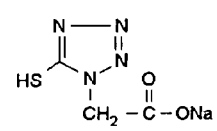
Figure 4J:
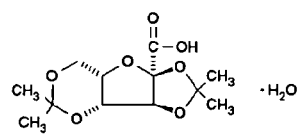
Figure 4J:
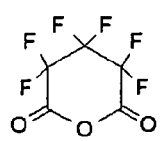
Figure 4J:
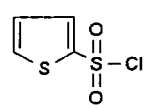
Figure 4J:
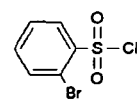
Figure 5C:
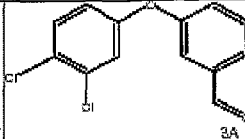
FIG. 5 shows 54 aldehyde moieties used in exemplified invention combinatorial libraries.
Figure 5C:
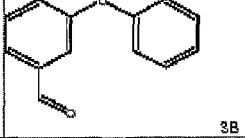
Figure 5C:
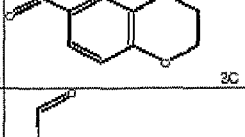
Figure 5C:
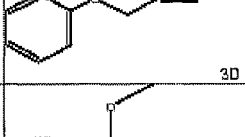
Figure 5C:
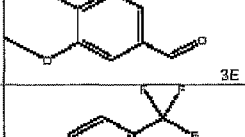
Figure 5C:
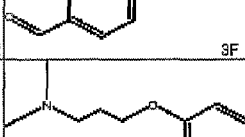
Figure 5C:
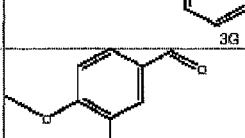
Figure 5C:
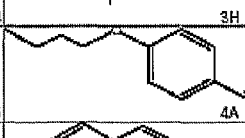
Figure 5C:
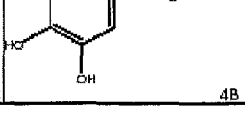
Figure 5C:
Figure 5F:
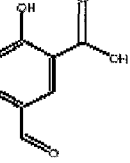
Figure 5F:
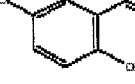
Figure 5F:
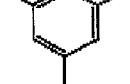
Figure 5F:
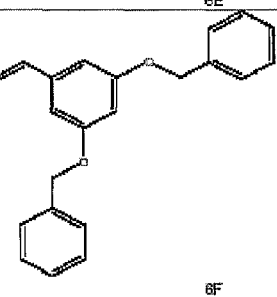
Figure 5F:
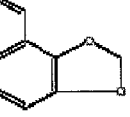
Figure 5F:
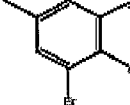
Figure 5F:
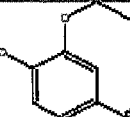
Figure 5F:
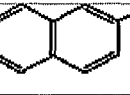
Figure 5F:
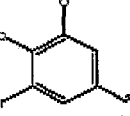
Figure 5G:
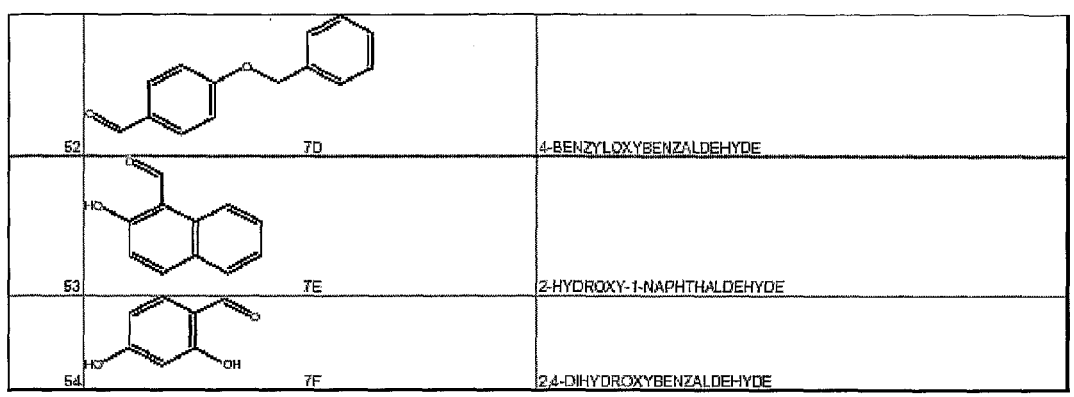

The ATP binding pocket of PKCα is known to accommodate an array of hydrophobic heterocyclic compounds and could very well serve as the binding site for the pyrrole phenylacyl moiety. We examined this possibility by obtaining the inhibition patterns for peptide 3 (and the diacetylated control peptide 4). Compound 3 is a competitive inhibitor versus variable peptide substrate (data not shown), but serves as an uncompetitive inhibitor with respect to ATP (FIG. 3). Since ATP and 3 do not act on PKCα in a mutually exclusive fashion, this suggests that the 4-pyrrole phenylacyl moiety binds to a subsite other than the ATP pocket. The advantage associated with this behavior is that the high intracellular levels of ATP will not curtail the inhibitory potency of 3 (Lawrence and Niu, 1998).

The 4-pyrrole phenylacyl group in 3 enhances inhibitory activity by 3 orders of magnitude relative to 4. Furthermore, peptide 3 surpasses the inhibitory potency displayed by some of the most powerful peptide-based active site-directed inhibitors of PKC, including the 33 amino acid-containing defensins (Charp et al., 1988). Nevertheless, we decided to explore whether an even more potent inhibitor of PKCα could be identified by taking advantage of one of the features inherent within the strategy outlined in FIG. 1. With the acquisition of a lead substituent at one position in the active site-directed inhibitor (e.g. 3), it should be possible to employ this substituent as a biasing element in the search for affinity enhancing moieties at other sites on the peptide chain. We chose the 4-pyrrole phenylacyl moiety from peptide 3 as the biasing substituent and prepared sublibrary IV, which contains diversity elements positioned at the N-terminus. The primary lead 6 was identified from library IV and, as with leads 1-3, resynthesized and enzymologically characterized. Compound 6 displays a $K_i$ of 800 pM, approximately 3 orders of magnitude more potent than compound 3 and 6 orders of magnitude more potent than the starting parent peptide 4. To the best of our knowledge, compound 6 is the most powerful protein binding site-directed inhibitor ever reported for a protein kinase.

PKCα belongs to a family of closely related protein kinases (PKCs) (Way et al., 2000; Hofmann, 1997). The high sequence homology displayed by the PKC family members has rendered acquisition of isoform-selective inhibitory agents exceedingly difficult (Way et al., 2000; Hofmann, 1997). Indeed, as far as we are aware, a potent PKCα-selective inhibitor has not been reported. Although the leads identified in libraries I, II, and III display a less than 3-fold selectivity for PKCα versus other PKC isoforms (data not shown), extraordinary selectivity is observed with the secondary library lead 6. The latter exhibits a profound preference for PKCα versus its closely related conventional PKCβ (385-fold) and PKCγ (580-fold) counterparts. Higher selectivities are observed versus the more distantly related novel (PKCδ: 2730-fold; PKCε: 600-fold; PKCη: 1310-fold; PKCθ: 1210-fold) and atypical (PKCτ: 940-fold; PKCζ: 640-fold) sub-families. These results suggest that the N-terminal substituent in 6 accesses a structurally distinct subsite unique to PKCα.

In summary, we have identified an extraordinarily potent and highly selective PKCα inhibitor via the stepwise combinatorial modification of a consensus sequence scaffold. The inhibitory agent exhibits an uncompetitive inhibition versus ATP, thereby suggesting that the intracellular effectiveness of 3 (or 6) will not be curtailed by the high levels of ATP present in living cells.

Materials and Methods

Materials and Chemicals were obtained from Aldrich, except for piperidine, protected amino acids, 1-hydroxybenzotriazole (HOBt), benzotriazole-1-yloxytris-pyrrolidino-phosphonium hexafluorophosphate (PyBOP), N,N,N',N'-tetramethyl-(succinimido)uranium tetrafluoroborate (TSTU), and TentaGel resin, which were obtained from Advanced Chemtech and Bachem. PKC enzymes were purchased from PanVera. Unifilter plates were obtained from Whatman. Solvent-resistant MULTISCREEN® 96-well filter plates and the MULTISCREEN® 96-well filterplate vacuum manifold were purchased from Millipore Corp.

Peptide Synthesis. All peptides were synthesized on an Advanced Chemtech Model 90 Tabletop Peptide Synthesizer using a standard 9-fluorenylmethoxycarbonyl (Fmoc) solid-phase peptide synthesis protocol. Crude peptides were purified on a preparative HPLC column using three Waters radial compression modules (25×10 cm) connected in series. Purified peptides were further characterized by mass spectrometry.

Synthesis of Peptide Libraries I, II and III. TentaGel S COOH (90 μm, 5 g, 0.2 mmol/g) was added to TSTU (5.0 eq, 0.53 g) in 200 mL of DMF and was shaken I h at ambient temperature. Cystamine dihydrochloride (10 eq, 2.25 g) and N-methylmorpholine (NMM; 20 eq, 2.02 g) in 200 mL of $H_2O$ were added to this solution and subsequently shaken overnight at ambient temperature. The free amine substitution level was determined to be 0.025 mmol/g. This low substitution level is ideal for our purposes since this not only ensures a higher coupling yield but, in addition, larger quantities of resin (with greater weight accuracy) can be subsequently introduced into the 96-well plates. The peptide libraries I, II, and III were synthesized on the cystamine-substituted TentaGel resin using a Fmoc solid-phase peptide synthesis protocol. After deprotection of the amino terminal Fmoc (for library I) or NH-t-butyloxycarbonyl group (tBoc; for libraries II and III), the resin was extensively washed and subsequently dried in vacuo. The peptide-bound resin was distributed in 5-mg quantities into each well of solvent-resistant 96-well filter plates. In addition, each well contained a carboxylic acid-containing compound (400 eq, 20 μmol), PyBOP (200 eq), HOBt (200 eq), and NMM (1,000 eq) in 50 μL of DMF. A total of 720 different carboxylic acids (each dissolved in DMF and added in 100 μL quantities) were employed. The plates were shaken overnight, and then each well subjected to a series of wash steps (3×200 μL of DMF, 3×200 μL of isopropyl alcohol, and 3×200 μL of $CH_2Cl_2$). The NH-4-methoxy-2,3,6-trimethylbenzene-sulfonyl (Mtr) side chain protecting groups were cleaved with trifluoroacetic acid (TFA):thioanisole (95:5) at ambient temperature. The peptide-nonpeptide conjugates were cleaved from the disulfide-containing resin with 10 mM dithiothreitol (DTT) in 50 mM Tris, pH 7.5 (1×200 μl for 1 h and 2×150 μL for 1 h each) and filtered into a receiving set of 96-well plates using the vacuum manifold (final volume of 500 μL). The efficiency of acid coupling, peptide cleavage from the resin with DTT solution, and purity of peptide-nonpeptide conjugates was assessed via the ninhydrin test and HPLC. No free N-terminal peptide was detected, and >90% of total ligand was cleaved from the resin with first the DTT wash step. The final two DTT washings removed the residual resin-bound peptide. Compound purity was >90% as assessed by HPLC, and the HPLC-purified compounds (i.e. removal of Tris buffer and DTT) were characterized by matrix-assisted laser desorption ionization mass spectrometry.

Synthesis of Peptide Library IV. The side chain protected peptide resin Fmoc-Ala-Arg-Arg-Gly-Ala-Leu-Arg-Dap-Ala-NH(CH$_2$)$_2$SS(CH$_2$)$_2$NH-TentaGel was synthesized as described above for libraries I-III. The Boc group on the Dap side chain was removed with TFA:CH$_2$Cl$_2$ 1:1 and subsequently acylated with 4-(1H-pyrol-1-yl)benzoic acid. The N-terminal Fmoc group was removed and the resin-bound peptide distributed in 5 mg quantities into each well of solvent-resistant 96-well filter plates. In addition, each well contained a carboxylic acid-containing compound (400 eq, 20 µmol), PyBOP (200 eq), HOBt (200 eq), and NMM (1,000 eq) in 50 µL of DMF. A total of 720 different carboxylic acids (each dissolved in DMF and added in 100 µL quantities) were employed. The plates were shaken overnight, and then each well subjected to a series of wash steps (3×200 µL of DMF, 3×200 µL of isopropyl alcohol, and 3×200 µL of CH$_2$Cl$_2$). The Mtr side chains were removed and the peptides cleaved from the resin as described in the protocol for the synthesis of libraries I-III.

Peptide 3. The peptide was resynthesized using the protocol described above for library III with the exception that Arg-Pbf (2,2,4,6,7-pentamethyldihydrobenzofuran-5-sulfonyl) was used in place of Arg-Mtr. The Pbf protecting groups were removed via treatment with TFA:triisopropylsilane (TIS):H$_2$O (95:2.5:2.5) for 2-3 hr. The deprotected peptide was subsequently released from the resin using the DTT cocktail described for library III.

$^1$H NMR (D$_2$O): δ7.96-7.99 (d, J=8.71 Hz, 2H), 7.74-7.77 (d, J=8.78 Hz, 2H), 7.48-7.50 (dd, J=2.20, J=2.20 Hz, 2H), 6.55-6.57 (dd, J=2.11 Hz, J=2.11 Hz, 2H), 4.38-4.42 (m, 8H), 4.01 (s, 2H), 3.94-4.02 (m, 2H), 3.82-3.85 (m, 2H), 3.45 (m, 2H), 3.26-3.31 (m, 4H), 3.15-3.18 (m, 2H), 2.71 (m, 2H), 2.12 (s, 3H), 1.87-1.91 (m, 6H), 1.67-1.73 (m, 8H), 1.44-1.52 (m, 8H), 0.94-0.96 (d, J=5.97 Hz, 3H), and 0.89-0.91 (d, J=5.97 Hz, 3H); ESIMS m/z calculated for C$_{53}$H$_{87}$N$_{21}$O$_{11}$S 1226.6, 1227.6, 1228.6 (MH$^+$). Found m/z 1226.6, 1227.5, 1228.4.

Peptide 4. The side chain protected peptide resin Fmoc-Ala-Arg-Arg-Gly-Ala-Leu-Arg-Dap-Ala-NH-Rink resin was synthesized using the protocol described above for library III using Rink SS resin instead of TentaGel S COOH. The deprotected peptide was subsequently released from the resin using a TFA/TMSBr/ethanedithiol/m-cresol/thioanisole cocktail (v/v 70:13:5:1:11) for 15 min under a blanket of N$_2$ at 0° C.

ESIMS m/z calculated for C$_{43}$H$_{79}$N$_{19}$O$_{11}$ 1038.6, 1039.6, 1040.6 (MH$^+$). Found m/z 1038.9, 1039.9, 1040.9.

Peptide 6. The peptide was resynthesized using the protocol described above for library IV with the exception that Arg-Pbf was used in place of Arg-Mtr. The Pbf protecting groups were removed via treatment with TFA:TIS:H$_2$O (95:2.5:2.5) for 2-3 hr. The deprotected peptide was subsequently released from the resin using the DTT cocktail described for library IV.

$^1$H NMR (D$_2$O): δ7.95 (d, J=8.74 Hz, 2H), 7.70-7.78 (m, 3H), 7.53-7.60 (m, 4H), 7.44-7.49 (m, 2H), 6.79 (d, J=8.74 Hz, 1H), 4.38-4.42 (m, 8H), 3.67-3.98 (m, 29H), 3.42-3.49 (m, 3H), 3.09-3.40 (m, 6H), 2.65-2.72 (m, 2H), 1.47-1.91 (m, 24H), 0.89-0.98 (m, 6H); ESIMS calculated for C$_{59}$H$_{89}$N$_{21}$O$_{11}$SCl$_2$ m/z 1370.6, 1371.6, 1372.6, 1373.6, 1374.6, 1375.6, 1376.6 (MH$^+$). Found m/z 1370.8, 1371.8, 1372.8, 1373.7, 1374.8, 1375.9, 1376.7.

Protein Kinase C Assay (general). The peptides Ac-Ser-Phe-Arg-Arg-Arg-NH$_2$ (for PKC α, β and γ) (SEQ ID NO:11) and acetyl-Pro-Arg-Lys-Arg-Glu-Gly-Ser-Val-Arg-Arg-NH$_2$ (for PKC ε and ζ) (SEQ ID NO:12) were used as substrates. The K$_m$ values for these peptides are 15 µM (PKCα) and 5.9 µM (PKCε), respectively, whereas the V$_{max}$ values are 0.526 µmol/min-mg (PKCα) and 1.445 µmol/min-mg (PKCε), respectively.

Protein Kinase Cα Assay (library screening). 20 µL of 37.5 µM peptide inhibitor candidate (from each well of libraries I, II, III, and IV) was added to each well of 96 multiwell assay plates containing 20 µL assay buffer [62.5 mM HEPES (pH 7.5), 50 µM Ac-Ser-Phe-Arg-Arg-Arg-NH$_2$ (SEQ ID NO:11), 2.0 mM CaCl$_2$ 2H$_2$O, 34 mM MgCl$_2$.6H$_2$O, 1.4 mM EGTA.Na, phosphatidylserine (225 µg/mL), diacylglycerol (40 µg/mL) and 313 µM cold ATP supplemented with 70-163 µCi/well [γ$^{-33}$P]ATP for radioactive detection]. 10 µL enzyme diluted buffer containing 20 mM Tris (pH 7.5), PKC (0.5 ng/µL), 1 mM DTT, BSA (730 µg/mL) and 1 mM EDTA.4Na.2H$_2$O were added last to initiate the reaction. Total reaction volume was 50 µL. After a 10-min incubation at 30° C., 100 µL of 6% phosphoric acid was added to each well to stop the reaction (total volume: 150 µL). Following an additional 5 min incubation at ambient temperature, 75 µL from each reaction well was transferred into each well of a Unifilter (P81 cellulose phosphate paper) assay plate and washed four times with 0.1% phosphoric acid in water. Scintillation solution was added to each well and $^{33}$P-incorporation measured by scintillation counting with a MICROBETA® TriLux & MicroBeta JET (Perkin Elmer). IC$_{50}$ values were calculated using GraFit (Erithacus Software Limited) and K$_i$ values were calculated using Enzyme Kinetics, SigmaPlot (SPSS Inc.)

PKCε and ζ Assay (IC$_{50}$ determinations). 20 µL of 37.5 µM peptide library was added in 20 µL assay buffer containing 62.5 mM HEPES (pH 7.5), 1 M MgCl$_2$.6H$_2$O, 40 mM EGTA.Na, PS (10 mg/mL) and 295 µM cold ATP supplemented with 70-163 µCi/well [γ$^{-33}$P]ATP for radioactive detection. 10 µL enzyme diluted buffer containing 10 mM HEPES (pH 7.5), 10 mM DTT, BSA (3.8 mg/mL), 10 mM EDTA.4Na.2H$_2$O and PKC (20 ng/µL) were added last to this buffer. Reactions were carried out as described above for the Protein Kinase Cα assay.

Protein Kinase Cα Assay (K$_i$ determination for peptides 3 and 4 versus variable Ac-Ser-Phe-Arg-Arg-Arg-NH$_2$ substrate). 20 µL of peptide 3 (concentrations=0, 1.25, 2.5, 5 and 10 µM) was added to a 20 µL assay buffer containing 62.5 mM HEPES (pH 7.5), peptide substrate (concentrations=10, 20, 40 and 80 µM), 2.0 mM CaCl$_2$.2H$_2$O, 34 mM MgCl$_2$.6H$_2$O, 1.4 mM EGTA.Na, phosphatidylserine (225 µg/mL), diacylglycerol (40 µg/mL), and 313 µM cold ATP supplemented with 70-163 µCi/well [γ$^{-33}$P]ATP for radioactive detection. 10 µL enzyme diluted buffer containing 20 mM Tris (pH 7.5), PKC (0.5 ng/µL), 1 mM DTT, BSA (730 µg/mL) and 1 mM EDTA.4Na.2H$_2$O were added to initiate the reaction. Subsequent assay workup and scintillation counting were performed as described under "Protein Kinase C α, β and γ Assay (library screening)". An analogous protocol was employed for peptide 4 versus variable [Ac-Ser-Phe-Arg-Arg-Arg-NH$_2$].

Protein Kinase Cα Assay (K$_i$ determination for peptides 3 and 4 versus variable ATP).

20 µL of peptide 3 (concentrations=0, 1.25, 2.5, 5 and 10 µM) was added to a 20 µL assay buffer containing 62.5 mM HEPES (pH 7.5), 50 µM peptide substrate, 2.0 mM CaCl$_2$.2H$_2$O, 34 mM MgCl$_2$.6H$_2$O, 1.4 mM EGTA.Na, phosphatidylserine (225 µg/mL), diacylglycerol (40 µg/mL), and cold ATP (concentrations=10, 12.5, 16.5, 25 and 50 µM each) supplemented with 7-16 µCi/well [γ$^{-33}$P]ATP for radioactive detection. 10 µL enzyme diluted buffer containing 20 mM Tris (pH 7.5), PKC (0.5 ng/µL), 1 mM DTT, BSA (730 µg/mL) and 1 mM EDTA.4Na.2H$_2$O were added to initiate the reaction. Subsequent assay workup and scintillation counting were performed as described under "Protein Kinase C α, β and γ Assay (library screening)". An analogous protocol was employed for peptide 4 versus variable [ATP].

Protein Kinase Cα Assay (K$_i$ determination for peptide 6 versus variable Ac-Ser-Phe-Arg-Arg-Arg-NH$_2$ substrate) (SEQ ID NO:11). The assay was conducted as described above for peptide 3 versus variable peptide substrate with the exception that the enzyme solution contained a ten-fold lower concentration of PKCα (0.05 ng/µL). The reaction was initiated as described above. After an 18-min incubation at 30° C., 100 µL of 6% phosphoric acid was added to each well to stop the reaction (total volume: 150 µL). Following an additional 5 min incubation at ambient temperature, 75 µL from each reaction well was transferred into each well of a Unifilter (P81 cellulose phosphate paper) assay plate and washed four times with 0.1% phosphoric acid in water. Scintillation solution was added to each well and $^{33}$P-incorporation measured by scintillation counting with a MICROBETA® TriLux & MicroBeta JET (Perkin Elmer). IC$_{50}$ values were calculated using GraFit (Erithacus Software Limited) and K$_i$ values were calculated using Enzyme Kinetics, SigmaPlot (SPSS Inc.)

Protein Kinase Cα Assay (IC$_{50}$ determination for peptide 6 versus histone III-S substrate). 20 µL assay buffer solution containing 62.5 mM Hepes (pH 7.5), CaCl$_2$.2H$_2$O (1.88 mM), MgCl$_2$.6H$_2$O (31.3 mM), EGTA.Na (1.3 mM), PS (450 µg/mL), DAG 40 µg/mL, cold ATP (313 µM), supplemented with 70-163 µCi/well [$^{33}$P]ATP for radioactive detection with 625 nM histone III-S as substrate were added to 20 µL of a solution containing peptide 6 at various concentrations (4, 8, 16, 32, 64, 128, 256, 512 nM). 10 µL enzyme buffer solution containing 20 mM Tris (pH 7.5), PKCα (0.05 ng/µL), 1 mM DTT, BSA (730 µg/mL), and EDTA.4Na.2H$_2$O (1 mM) were added to start the reaction. After an 18 min incubation at 30° C., 100 µL of 6% phosphoric acid was added to quench the reaction at room temperature. The resulting volume in each individual well is 150 µL. Following an additional 5 min incubation, 75 µL from each well was transferred to Unifilter P81 cellulose phosphate paper and washed with 0.1% phosphoric acid (3×200 µL) and water (200 µL). Scintillation solution was added to each well and $^{33}$P incorporation measured by scintillation counting with MICROBETA® TriLux & MicroBeta JET (Perkin Elmer). The IC$_{50}$ value for compound 6 as an inhibitor of histone III-S phosphorylation was found to be 31.7±0.8 nM as calculated using GraFit (Erithacus Software Limited).

Fluorescein-labeled Peptide 7. Peptide 3 (3.67 mg, 3.0 mmol) and 5-iodoacetamidofluorescein (3.09 mg, 6.0 mmol) were added to 2 mL of Tris buffer (100 mM, pH 7.5) and subsequently shaken overnight at ambient temperature in the dark.

$^1$H NMR (D$_2$O): δ7.96 (s, 1H), 7.61-7.52 (m, 3H), 7.18-7.16 (m, 2H), 7.00 (s, 1.5H), 6.75-6.54 (m, 8H), 6.20 (s, 1.5H), 4.23-4.11 (m, 6H), 3.80 (m, 2H), 3.65 (s, 2H), 3.54-3.51 (m, 4H), 3.50-3.41 (m, 4H), 3.04-2.93 (m, 6H), 2.76-2.72 (m, 2H), 1.92 (s, 3H), 1.69-1.65 (m, 5H), 1.47-1.43 (m, 8H), 1.26-1.09 (m, 9H), and 0.62-0.65 (m, 6H); ESIMS m/z calculated for C$_{75}$H$_{100}$N$_{22}$O$_{17}$S 1612.7, 1613.7, 1614.7 (MH$^+$). Found m/z 1612.5, 1613.5, 1614.5

Determination of K$_D$ Values. The K$_D$ value for the fluorescein-labeled peptide 7/PKCα complex was determined via equilibrium dialysis (note: peptide 7 does not exhibit any significant change in fluorescence upon binding to PKCα). All samples were prepared in a buffer containing 50 mM HEPES (pH 7.5), 0.8 mM CaCl$_2$.2H$_2$O, 13.6 mM MgCl$_2$.6H$_2$O, 0.56 mM EGTA.Na, phosphatidylserine (90 µg/mL), diacylglycerol (16 µg/mL), 4 mM Tris (pH 7.5), 0.2 mM DTT, BSA (146 µg/mL), 0.2 mM EDTA.4Na.2H$_2$O and AMP-PNP (a nonhydrolyzable ATP analogue) or without AMP-PNP at pH 7.5. Slide-A-Lyzer dialysis slide cassettes (Pierce, 10K MWCO, 0.1-0.5 mL capacity) were employed and contained 250 nM PKCα and 500 nM fluorescein-labeled peptide 7. The slide cassettes contained a final volume of 180 µL. The cassettes were placed in beaker containing a volume of buffer solution that was at least 500-fold greater than that of the sample volume in the dialysis slide cassette. Equilibrium dialysis experiments were performed over a period of 16 hr and maintained at 4° C. The fluorescence intensity of the solutions in the slide cassette (F$_i$) and in the beaker (F$_o$) was measured. The excitation wavelength for the fluorescein-labeled peptide 7 was 499 nm and the emission monitored at 519 nm. The K$_D$ values were calculated from Equation 1. K$_D$=203 nM (with AMP-PNP) and 1.8 µM (without AMP-PNP).

$$E_D = \frac{\{[E]_T - [E \cdot P]\}[P]}{[E \cdot P]}$$

where [E]$_T$=total enzyme concentration; [E•P]=enzyme-peptide complex; [P]=free peptide concentration.

Example 2

Peptide Mosaics: A Combinatorial Strategy for the Acquisition of Highly Selective PKC Inhibitors For Novel And Atpical Isoforms Example Summary Members of the PKC family of enzymes have been implicated as participants in a wide variety of cellular phenomena. For example, the α, β, and ζ isoforms are thought to serve as key players in motility. We have prepared potent, yet exquisitely selective, active site-directed inhibitors for these PKC isoforms in order to explore their role in the signaling pathways that contribute to cofilin phosphorylation. The inhibitors were derived from a starting consensus sequence peptide (RRQGAFMYF) (SEQ ID NO:13), which displays modest affinity and little selectivity for the individual PKC isoforms. An automated parallel synthesis protocol was applied to the consensus sequence, in which specific sites on the peptide scaffold were modified with unnatural substituents to create libraries of 720 analogues. The libraries were screened for inhibitory activity and subsequently modified at a second site to ultimately create inhibitors with the desired properties. The lead PKC δ inhibitor exhibits a K$_i$ of 8±1 nM and a selectivity that ranges from 25-fold versus PKC τ to greater than 200-fold versus the other PKC isoforms. In an analogous vein, the PKC ζ inhibitor displays a K$_i$ of 3.9±0.2 nM and a selectivity of between 400 to nearly 3.000-fold versus other members of the PKC family. To the best of our knowledge, these compounds are the most PKC isoform-selective inhibitors described to date and represent the first examples of selective inhibitors that target specific members of the atypical and novel classes of PKC.

The abbreviations used in this Example are: ADF, actin depolymerizing factor; Adpoc, 1-(1'-Adamantyl)-1-methyl-ethoxycarbonyl; BSA bovine serum albumin; consensus peptide-1, Fmoc-Arg(Pbf)-Arg(Pbf)-Gln(Trt)-Gly-Dap(Adpoc)-Phe-Met-Tyr(t-butyl)-Phe-S-S-Tentagel-Resin; consensus peptide-2, $H_2N$-Arg(Pbf)-Arg(Pbf)-Gln(Trt)-Gly-Dap[3-NH-(4-nitrohippuryl)]-Phe-Met-Tyr(t-butyl)-Phe-S-S-Tentagel-Resin; DAG, diacylglycerol; Dap, 2,3-diaminopropionic acid; DIPEA, diisopropylethylamine; DMF, dimethyformamide; DMSO, dimethyl sulfoxide; DTT, dithithreitol; EDTA, ethylenediaminetetraacetic acid; EGF, epidermal growth factor; ESI, electrospray ionization; FITC, fluorescein isothiocyanate; Fmoc, 9-fluorenylmethoxycarbonyl; HOBt, 1-hydroxybenzo-triazole; HPLC, high performance liquid chromatography; MALDI, matrix assisted laser desorption/ionization; MS, mass spectroscopy; MTT, 4-methyltrityl; NMM, N-methylmorpholine; NMR, nuclear magnetic resonance; Pbf, 2,2,4,6,7-pentamethyl-dihydrobenzofuran-5-sulfonyl; PBS, phosphate buffered saline; PKC, protein kinase C; PMA, phorbol myristic acid; PS, L-α-phosphatidyl-L-serine; PyBOP, benzotriazole-1-yloxytris-pyrrolidinophosphonium hexafluorophosphate; RACK, receptor for activated C kinase; RP-HPLC, reverse phase high performance liquid chromatograph; SPPS, solid phase peptide synthesis; TBS, Tris buffered saline; TFA, trifluoroacetic acid; TIS, triisopropylsilane; TMOF, trimethyl orthoformate; Trt, trityl; TSTU, N,N,N',N'-tetramethyl-(succinimido)uranium tetrafluoroborate.

Introduction

Highly selective reagents that inhibit or suppress the expression of specific protein targets serve as extraordinarily powerful tools for correlating biochemical activity with cellular behavior. Although genetic strategies, such as antisense and more recently siRNA, are exquisitely selective, their mechanism of action precludes the rapid disruption of target protein activity. Consequently, these technologies are difficult to apply with high temporal precision to proteins that participate in comparatively rapid cell-based phenomena, such as mitosis or motility. By contrast, reagents that act at the protein level, such as inhibitors, activators, or ligands, are fast acting but typically display poor selectivity. For example, the acquisition of selective inhibitory agents for individual members of the highly conserved protein kinase family remains a difficult challenge. Given the large number of protein kinases encoded by the human genome, an ideal strategy would not only address the twin issues of potency and selectivity, but would do so in a predictable fashion that could be automated. We report herein the acquisition of highly selective inhibitors for two members of the protein kinase C (PKC) subfamily of protein kinases via the application of a recently described consensus sequence-derived library-based strategy (Lee et al., 2004).

In conjunction with our interest in the role of PKC in cofilin-mediated cell motility (Ghosh et al., 2004; Zebda et al., 2000; Ghosh et al., 2002), we required access to selective inhibitors for the novel PKC isoform δ and its atypical counterpart ζ. The PKC family is comprised of at least 10 different isoforms that are divided into three separate groups based upon their ability to respond to specific stimuli (Liu and Heckman, 1998; Toker, 1998). The conventional PKCs include the α, β (I and II), and γ isoforms, all of which are $Ca^{2+}$-dependent and are activated by phosphatidylserine (PS) and diacylglycerol (DAG). PKC δ, ε, η, and θ comprise the novel subcategory and, although regulated by PS and DAG, are $Ca^{2+}$-independent. The atypical PKCs, namely τ and ζ, require PS but otherwise function independently of $Ca^{2+}$ and DAG. Members of the PKC family exhibit a significant degree of structural homology, particularly within individual subgroups. For example, there is an approximately 50% active site sequence identity between PKC τ and its counterparts in the conventional and novel groups (Selbie et al., 1993). However, sequence identity increases to 85% when a comparison is made between τ and its atypical counterpart ζ.

A large number of active site-directed PKC inhibitors have been described. However, given the high sequence homology that characterizes PKC family members, it is not surprising that these inhibitory agents generally display modest to little or no selectivity for specific PKC isoforms (Way et al., 2000; Mackay and Twelves, 2003). Nevertheless, there are two notable exceptions to the weak isoform selectivity exhibited by active site-targeted agents. An Eli Lilly group has reported extensive studies on the development of a selective PKC β inhibitor that interacts with the ATP binding site (Jirousek et al., 1996). The latter is currently in clinical trials for the treatment of complications associated with diabetes (Ishii et al., 1996; Tuttle and Anderson, 2003). In addition, we have recently described a strategy that furnished a highly selective PKC α inhibitor that associates with the protein substrate-binding site (Lee et al., 2004). We report herein a modification of the latter strategy that has furnished highly selective inhibitors for PKC δ and ζ. To the best of our knowledge, these inhibitors are the first examples of active site-directed agents that display a pronounced preference for specific members of the novel and atypical groups of the PKC family.

Materials And Methods

General procedures. The resins and reagents used for solid phase peptide synthesis, including Tentagel resin, Rink resin, N-9-fluorenylmethyloxycarbonyl (Fmoc)-L-amino acids, N,N,N',N'-tetramethyl-(succinimido)uranium tetrafluoroborate (TSTU), benzotriazole-1-yloxytris-pyrrolidinophosphonium hexafluorophosphate (PyBOP), 1-hydroxybenzotriazole (HOBt), were purchased from Advanced ChemTech. Peptide synthesis grade dichloromethane, N,N-diisopropylethylamine (DIPEA), dimethylformamide (DMF) and trifluoroacetic acid (TFA) were purchased from Fisher and piperidine was obtained from Lancaster. 2-Fmoc-3-[1-(1'-Adamantyl)-1-methyl-ethoxycarbonyl]-diaminopropionic acid (Fmoc-Dap(Adpoc)-OH) was obtained from Bachem. Triisopropylsilane (TIS) was purchased from Acros. The 720 carboxylic acids and the 54 aromatic aldehydes used for the preparation of the peptide libraries were purchased from Aldrich. The reagents for the PKC assay were purchased from Sigma: EDTA (ethylenediaminetetraacetic acid, disodium salt,), BSA (bovine serum albumin), PS (L-α-phosphatidyl-L-serine from bovine brain), and DAG (diacylglycerol).

The PKC isoforms employed in this study were purchased from Panvera. Radioactive γ-$P^{33}$-ATP was obtained from AmerSham Biosciences. 96-well (2 mL/well) Uniplates and P81 Cellulose Phosphate Paper Unifilter Plates were obtained from Whatman Inc. Solvent-resistant MULTISCREEN® 96-well (300 μL/well) filter plates, the MULTISCREEN® Resist Vacuum Manifold, and Tape Multiscreen Harvester CL Plates were purchased from Millipore Corporation. Radioactive intensity of the library assays and $IC_{50}$ determinations was detected by 1450 Microbeta liquid scintillation counter. GraFit Version 5 was used to determine the $IC_{50}$ values.

1D, 2D-$^1$H and $^{13}$C NMR spectra of the peptide inhibitors were recorded on a DR×300 MHz Spectrometer in $H_2O$ and DMSO, and chemical shifts are reported in parts per million (ppm) downfield from $(CH_3)_4Si$. The molecular weights of the peptides were analyzed with MALDI (Matrix Assisted Laser Desorption/Ionization) mass spectrometry on the Applied Biosystems Voyager DE STR and ESI-MS (Electrospray Ionization Mass Spectrometry) on the Applied Biosystems MDS SCIEX API Qstar Pulsar I. Reverse phase high performance liquid chromatograph (RP-HPLC) was performed on a Waters SD-200 solvent delivery system equipped with a 500 UV/Vis-absorbance detector and recorded on an Apple Macintosh computer using model 600 software (Applied Biosystems Inc.). Chromatographic separations were achieved using linear gradients of buffer B in A (A=0.1% aqueous TFA; B=0.1% TFA in $CH_3CN$) over 50 min at a flow rate of 12 mL/min using a detection wavelength of 218 nm on Delta-Pak $C_{18}$ (300 Å, 15 µm, 3×15 cm) column.

Peptide Synthesis. Peptides were synthesized using a standard Fmoc solid phase peptide synthesis (SPPS) protocol on an Innova 2000 platform shaker or on an Advanced Chemtech Model 90 Tabletop Peptide Synthesizer.

Synthesis of Fmoc-Arg(Pbf)-Arg(Pbf)-Gln(Trt)-Gly-Dap(Adpoc)-Phe-Met-Tyr(t-butyl)-Phe-S-S-Tentagel-Resin ("consensus peptide-1"): 5 g of Tentagel S COOH (90 µm, 0.2 mmol/g) and 1.94 g (15 mmol) of DIPEA were successively added to a solution of 1.5 g (5 mmol) of TSTU in 20 mL of DMF. The mixture was shaken for 2 h at ambient temperature. Subsequently, a mixture of 2.25 g (10 mmol) of cystamine dihydrochloride and 2.02 g (20 mmol) of N-methylmorpholine (NMM) in 20 mL of water was slowly added to the Tentagel reaction mixture. Heat was evolved upon addition. Upon cooling to room temperature, the reaction vessel was sealed and shaken overnight. The resin was then drained and washed successively with $H_2O$ (3×20 mL), DMF (3×20 mL), and $CH_2Cl_2$ (3×20 mL). The free amine substitution level on linker-coupled resin was found to be 0.05 mmol/g. The linker-coupled resin (5 g) was successively submitted to coupling reactions with the required amino acids followed by removal of the Fmoc protecting group via standard conditions (vide infra). The following amino acids were used for the synthesis of the lead sequence: Fmoc-Phe-OH, Fmoc-Tyr(t-butyl)-OH, Fmoc-Met-OH, Fmoc-Dap(Adpoc)-OH, Fmoc-Gly-OH, Fmoc-Gln(Trt)-OH, Fmoc-Arg(Pbf)-OH. Each residue was coupled for 3 h, and coupling efficiencies were determined by quantitative ninhydrin reaction (Sarin et al., 1981). The standard coupling conditions employed 5 eq. of Fmoc-amino acid, 5 eq. of HOBt, 5 eq. of PyBOP, and 10 eq. of NMM in 50 mL DMF with shaking for 3 h. After each coupling step, the resin was successively washed with DMF (3×20 mL), isopropyl alcohol (3×20 mL), and $CH_2Cl_2$ (3×20 mL). The Fmoc protecting group was removed with 20% piperidine in DMF (shaking for 20 min).

Library I. The Fmoc group in consensus peptide-1 was removed with 20% piperidine in DMF and the resin was subsequently mixed with a solution of $Ac_2O$ (0.51 g, 5 mmol) in DMF (40 mL). Then 1 g (10 mmol) of NMM was added and the mixture was shaken for 1 h. The resin was washed with DMF (3×20 mL), isopropyl alcohol (3×20 mL), and $CH_2Cl_2$ (3×20 mL) and subsequently dried in vacuo. The Adpoc group was selectively removed by adding the resin to a 40 mL solution of 3% TFA in $CH_2Cl_2$. The mixture was shaken for 5 min, the TFA solution drained, and the resin washed with DMF (3×20 mL). Exposure to TFA followed by washing with DMF was repeated two additional times. The resin was subsequently dried in vacuo. The peptide-bound resin was distributed in 5 mg quantities into individual wells of solvent-resistant MULTISCREEN® 96-well filter plates (8 plates total). To each well was added a solution of a carboxylic acid (200 eq.) in 100 µL DMF and a second solution containing PyBOP (200 eq.), HOBt (200 eq.), and NMM (400 eq.) in 100 µL of DMF. A total of 720 different carboxylic acids were employed. The plates were gently shaken overnight, and then each well subjected to a series of washing steps (3×200 µL of DMF, 3×200 µL of isopropyl alcohol, and 3×200 µL of $CH_2Cl_2$). All the side chain protecting groups, Boc, Trt, and Pbf, were removed via treatment with TFA:$H_2O$:TIS (95:2.5:2.5) for 2 h at ambient temperature. The resin was washed with DMF (3×20 mL), isopropyl alcohol (3×20 mL), and $CH_2Cl_2$ (3×20 mL) and the peptide-nonpeptide conjugates subsequently cleaved from the disulfide-containing resin with 10 mM dithiothreitol (DTT) in 50 mM Tris, pH 7.5 (1×200 µL for 3 h and 2×150 µL for 3 h each) and filtered into a receiving set of 96-well plates using a vacuum manifold (final volume of 500 µL). The coupling efficiency of the acylation reaction and the purity of peptide-nonpeptide conjugates were assessed via the ninhydrin test and RP-HPLC, respectively. No free N-terminal peptide was detected, and >90% of total ligand was cleaved from the resin with the first DTT cleaving step. The final two DTT washings removed the residual resin-bound peptide. Compound purity was >90% as assessed by HPLC, and the HPLC-purified compounds (i.e. removal of Tris buffer and DTT) were characterized by MALDI-MS. These peptides, containing 720 different groups at the Dap ⊖-amino position in 8 plates, comprise Library I.

Library II. The Adpoc group in consensus peptide-1 (5 g resin) was selectively removed with 40 mL of 3% TFA in $CH_2Cl_2$ (3×5 min) and the resulting free amine on the side chain of the Dap residue was coupled with 0.95 g (5 mmol) of 10-hydroxydecanoic acid in the presence of 3.25 g (5 mmol) of PyBop, 0.77 g (5 mmol) of HOBt, and 1.01 g (10 mmol) of NMM in 40 mL of DMF. The reaction mixture was shaken overnight. The solvent was removed from the resin and the resin subsequently washed with DMF (3×20 mL), isopropyl alcohol (3×20 mL), and $CH_2Cl_2$ (3×20 mL). The resin was exposed to 40 mL of 20% piperidine solution in DMF (2×20 min). The Fmoc group at the N-terminus was removed, the resin washed, dried, and then added in 5 mg quantities to the individual wells of 8 solvent-resistant MULTISCREEN® 96-well filter plates. The following procedures, as described for Library I, were employed: the resin in each well was coupled with one of 720 different carboxylic acids, the side chain protecting groups were removed, and the peptides were cleaved from the resin to furnish Library II.

Library III. The Adpoc group in consensus peptide-1 (5 g resin) was selectively removed with 40 mL of 3% TFA in $CH_2Cl_2$ (3×5 min) and the resulting free amine on the side chain of the Dap residue was coupled with 1.12 g (5 mmol) of 4-nitrohippuric acid in the presence of 3.25 g (5 mmol) of PyBop, 0.77 g (5 mmol) of HOBt, and 1.01 g (10 mmol) of NMM in 40 mL of DMF. The reaction mixture was shaken overnight. The solvent was removed from the resin and the resin subsequently washed with DMF (3×20 mL), isopropyl alcohol (3×20 mL), and $CH_2Cl_2$ (3×20 mL). The resin was exposed to 40 mL of 20% piperidine solution in DMF (2×20 min). The Fmoc group at the N-terminus was removed, the resin washed and dried. The peptide-resin at this stage is $H_2N$-Arg(Pbf)-Arg(Pbf)-Gln(Trt)-Dap[3-NH-(4-nitrohippuric-yl)]-Phe-Met-Tyr(t-butyl)-Phe-S-S-Tentagel-Resin ("consensus peptide-2"). The peptide-resin was added in 5 mg quantities to the individual wells of 8 solvent-resistant MULTISCREEN® 96-well filter plates. The following procedures, as described for Library I, were employed: the resin in each well was coupled with one of 720 different carboxylic acids, the side chain protecting groups were removed, and the peptides were cleaved from the resin to furnish Library III.

Library IV. 1.1 g of resin consensus peptide-2 was distributed in 10 mg quantities into 54 wells of a solvent-resistant MULTISCREEN® 96-well filter plate. 100 µL of a solution of an aromatic aldehyde in DMSO (0.5 M, 0.05 mmol, 50 eq.) was added to each well. 180 mg (3 mmol) NaCNBH$_3$ was dissolved in 6 mL of trimethyl orthoformate (TMOF) with shaking for 5 min, and the resultant solution was added in 100 µL portions to each well. The plate was sealed and shaken for 6 h. The solvent was then drained and the resin washed successively with DMF (3×100 µL), DMF/H$_2$O (1/1, 3×100 µL), H$_2$O (3×100 µL), MeOH/CH$_2$Cl$_2$ (1/1, 3×100 µL), and CH$_2$Cl$_2$ (3×100 µL). The resin was then exposed to a second round of reductive alkylation and washing steps. All the side chain protecting groups, Boc, Trt and Pbf, were removed with TFA:H$_2$O:TIS (95:2.5:2.5) in 2 h at ambient temperature. The peptide-nonpeptide conjugates were cleaved from the disulfide-containing resin with 10 mM DTT in 50mM Tris, pH 7.5 (1×200 µL for 3 h; and 2×150 µL for 3 h each) and filtered into a receiving set of 96-well plate using the vacuum manifold (final volume of 500 µL). These peptides in 54 wells comprise Library IV.

Synthesis of Ac-Pro-Arg-Lys-Arg-Gln-Gly-Ser-Val-Arg-Arg-Arg-Val(CONH$_2$) (SEQ ID NO:14). Fmoc-Val-OH, Fmoc-Arg(Pbf)-OH, Fmoc-Ser(t-butyl)-OH, Fmoc-Gly-OH, Fmoc-Gln(Trt)-OH, and Fmoc-Lys(Mtt)-OH were used for the synthesis of the peptide substrate for the novel and atypical PKC isoforms. 0.93 g of substrate was obtained from 2 g of Rink resin (0.6 mmol/g) using a standard solid phase peptide synthesis Fmoc protocol in a total yield of 43%. ESI-MS (m/z) calculated for C$_{63}$H$_{119}$N$_{30}$O$_{15}$ (MH$^+$) 1536.81. Found 1537.15.

Synthesis of compounds A-C. Compounds A, B, and C were synthesized using the Tentagel resin via the protocol described above for Libraries 1, 2, and 3. Their masses were obtained via mass spectrometry. Compound A: ESI-MS (m/z) calculated for C$_{60}$H$_{88}$N$_{18}$O$_{13}$S$_2$ (M$^+$) 1333.59. found 1333.67. Compound B: ESI-MS (m/z) calculated for C$_{68}$H$_{104}$N$_{18}$O$_{14}$S$_2$ (M$^+$) 1460.74. found 1461.00; Compound C: ESI-MS (m/z) calculated for C$_{72}$H$_{94}$FN$_{20}$O$_{17}$S$_2$ (MH$^+$) 1594.77. found 1594.62.

Synthesis of compound D. Compound D was prepared by adding a solution of 0.39 g (2.5 mmol) of 5-fluorosalicylic acid, 1.63 g (2.5 mmol) of PyBop, 0.40 g (2.5 mmol) of HOBt, and 0.50 g (5 mmol) of NMM in 25 mL of DMF to 2.5 g of consensus peptide-2. The reaction mixture was shaken overnight. The solvent was removed from the resin and the resin subsequently washed with DMF (3×20 mL), isopropyl alcohol (3×20 mL), and CH$_2$Cl$_2$ (3×20 mL). All the side chain protecting groups were removed by treatment with TFA:H$_2$O:TIS (95:2.5:2.5) for 2 h at ambient temperature. The peptide-nonpeptide conjugates were cleaved from the disulfide-containing resin with 10 mM DTT in 50 mM Tris, pH 7.5 (3×10 mL for 3 h each), and the resultant crude solution was purified by RP-HPLC. ESI-MS (m/z) calculated for C$_{67}$H$_{92}$N$_{20}$O$_{16}$S$_2$ (M$^+$) 1497.70. found 1498.17.

Synthesis of compound E. 2.5 g of Tentagel resin consensus peptide-2 was mixed with 30 mL of TFA:H$_2$O:TIS (95:2.5:2.5) and subsequently shaken for 2 h at room temperature. The solvent was removed, the resin washed with CH$_2$Cl$_2$ (3×30 mL), and dried in vacuo. The peptide was cleaved from the resin via treatment with 10 mM DTT buffer solution in 50 mM Tris (pH 7.5, 10 mL) for 3 hr. The solution was collected in a receiving plate and the resin was subsequently exposed to the DTT solution two additional times. The crude material was purified by RP-HPLC to furnish 42 mg of Compound E as a white solid. $^1$H NMR (300 MHz, DMSO, ppm) 8.15 (1H, s, CONH), 3.80 (1H, C$_\alpha$H), 1.68 (2H, C$_\beta$H$_2$), 1.51 (2H, C$_\gamma$H$_2$), 3.11 (2H, C$_\delta$H$_2$), 7.52 (N$^\epsilon$H) for Arg-1 from N-terminus; 8.58 (1H, s, CONH), 4.35 (1H, C$_\alpha$H), 1.72 (1H, C$_\beta$H$_1$), 1.54 (1H, C$_\beta$H$_1$), 1.51 (2H, C$_\gamma$H$_2$), 3.10 (2H, C$_\delta$H$_2$), 7.52 (N$^\epsilon$H) for Arg-2; 8.22 (1H, s, CONH), 4.27 (1H, C$_\alpha$H), 1.87 (1H, C$_\beta$H$_1$), 1.78 (1H, C$_\beta$H$_1$), 2.13 (2H, C$_\gamma$H$_2$) for Gln-3; 8.15 (1H, s, CONH), 3.81 (1H, C$_\alpha$H), 3.67 (1H, C$_\alpha$H) for Gly-4; 8.00 (1H, s, CONH), 4.37 (1H, C$_\alpha$H), 3.32 (1H, C$_\beta$H), 3.20 (1H, C$_\beta$H) for Dap-5; 8.00 (1H, CONH of Dap-4-nitro-hippuryl); 3.92 (2H, CH$_2$), 9.05 (1H, s, CONH), 8.08 (2H, 2×Ar—H at ortho position to CONH), 8.31 (2H, 2×Ar—H at meta position to CONH) for 4-nitro-hippuryl group; 8.16 (1H, s, CONH), 4.53 (1H, C$_\alpha$H), 2.95 (1H, C$_\beta$H$_1$), 2.75 (1H, C$_\beta$H$_1$), 7.18-7.23 (5H, m, 5×Ar—H) for Phe-6; 8.29 (1H, s, CONH), 4.35 (1H, C$_\alpha$H), 1.85 (1H, C$_\beta$H$_1$), 1.73 (1H, C$_\beta$H$_1$), 2.37 (2H, C$_\gamma$H$_2$), 2.00 (3H, SCH$_3$) for Met-7; 7.95 (1H, s, CONH), 4.46 (1H, C$_\alpha$H), 2.85 (1H, C$_\beta$H$_1$), 2.65 (1H, C$_\beta$H$_1$), 6.60 (2H, 2×Ar—H, meta to OH), 6.97 (2H, 2×Ar—H, ortho to OH) for Tyr-8; 8.17 (1H, s, CONH), 4.44 (1H, C$_\alpha$H), 2.95 (1H, C$_\beta$H$_1$), 2.80 (1H, C$_\beta$H$_1$), 7.18-7.23 (5H, m, 5×Ar—H) for Phe-9 (C-terminus); 8.04 (1H, s, CONHCH$_2$, 3.32 (1H, C$_\alpha$H, alpha from NH), 3.23 (1H, C$_\alpha$H), 2.63 (2H, C$_\beta$H$_2$). $^{13}$C NMR (300 MHz, DMSO, ppm) 54.90 (C$_\alpha$), 31.80 (C$_\beta$), 27-28 (C$_\gamma$), 43.60 (C$_\delta$) for Arg-1 from N-terminus; 55.30 (C$_\alpha$), 32.10 (C$_\beta$), 27-28 (C$_\gamma$), 43.60 (C$_\delta$) for Arg-2; 55.30 (C$_\alpha$), 31.30 (C$_\beta$), 34.30 (C$_\gamma$) for Gln-3; 45.10 (C$_\alpha$) for Gly-4; 55.30 (C$_\alpha$), 43.60 (C$_\beta$) for Dap-5; 46.30 (C(H$_2$)), 132.00 (2×C in aromatic ring at ortho position to CONH), 126.70 (2×C in aromatic ring at meta position to CONH) for 4-nitro-hippuryl group; 57.40 (C$_\alpha$), 40.20 (C$_\beta$), 132.3 (2C in aromatic ring), 131.3 (2C in aromatic ring), 129.3 (1C in aromatic ring) for Phe-6; 55.30 (C$_\alpha$), 35.40 (C$_\beta$), 32.50 (C$_\gamma$), 17.70 (C$_\delta$) for Met-7; 57.20 (C$_\alpha$), 39.80 (C$_\beta$), 117.90 (C, meta to OH), 133.20 (C, ortho to OH) for Tyr-8; 57.00 (C$_\alpha$), 41.10 (C$_\beta$), 132.3, 131.3, 129.3 (benzene ring) for Phe-6; (C-terminus); 41.20 (C$_\alpha$, alpha from NH), 39.80 (C$_\beta$). MALDI-MS (m/z) calculated for C$_{65}$H$_{90}$N$_{20}$O$_{15}$S$_2$ (M$^+$) 1455.67. found 1455.84. ESI-MS (m/z) calculated for C$_{65}$H$_{90}$N$_{20}$O$_{15}$S$_2$ (MH$^+$) 1456.68. found 1456.44.

Synthesis of compound F. 2.5 g of consensus peptide-2 was washed with 20 mL of DMF/MeOH/AcOH (9:9:2), the solvent was drained, and residual peptide-resin mixed with 52 mL of DMF/TMOF/MeOH/AcOH (25:25:1:1) containing 0.21 g (1.5 mmol) of 2,3-dihydroxybenzaldehyde. The reaction mixture was shaken for 30 min, the solvent removed, and exposure of the peptide-resin to the aldehyde repeated. The solvent was removed, the resin was washed briefly with DMF, and then 100 mg (1.5 mmol) of sodium cyanoborohydride in 52 mL of DMF/TMOF/MeOH/AcOH (25:25:1:1) was added. The reaction mixture was shaken for 30 min at room temperature. After removal of the solvent the resin was successively washed with DMF (3×20 mL), DMF/H$_2$O (1/1, 3×20 mL), H$_2$O (3×20 mL), MeOH/CH$_2$Cl$_2$ (1/1, 3×20 mL), CH$_2$Cl$_2$ (3×20 mL), and DMF (3×20 mL). The resin was subsequently exposed to a second cycle of the above protocol. All the side chain protecting groups were removed by exposing the resin to 25 mL of TFA:H$_2$O:TIS (95:2.5:2.5) for 2 h at ambient temperature. The peptide-nonpeptide conjugates were cleaved from the Tentagel resin with 10 mM DTT in 50 mM Tris, pH 7.5 (3×15 mL for 3 h each), and the filtered crude solution was purified with RP-HPLC. The eluent (peptide-containing 0.1% TFA solution in H$_2$O—CH$_3$CN) was lyophilized to give 16 mg of Compound F (white solid). $^1$H NMR (300 MHz, DMSO, ppm) 6.85 (1H, Ar—H, ortho to OH), 6.67 (1H, Ar—H), 6.74 (1H, Ar—H, ortho to CH$_2$), 3.99 (1H, 0.5×CH$_2$), 3.93 (1H, 0.5×CH$_2$) for 2,3-dihydroxybenzyl group on N$^\alpha$ atom of Arg-1 (N-terminus); 3.81 (1H, C$_\alpha$H), 1.71 (2H, C$_\beta$H$_1$), 1.50 (2H, C$_\gamma$H$_2$), 3.10 (2H, C$_\delta$H$_2$), 7.52 (N$^\epsilon$H) for Arg-1; 8.74 (1H, s, CONH), 4.40 (1H, C$_\alpha$H), 1.70 (1H, C$_\beta$H$_1$), 1.56 (1H, C$_\beta$H$_1$), 1.55 (2H, C$_\gamma$H$_2$), 3.10 (2H, $C_\delta H_2$), 7.52 (N$^\epsilon$H) for Arg-2; 8.26 (1H, s, CONH), 4.28 (1H, C$_\alpha$H), 1.89 (1H, C$_{\beta H_1}$), 1.78 (1H, C$_{\beta H_1}$), 2.14 (2H, C$_\gamma$H$_2$) for Gln-3; 8.15 (1H, s, CONH), 3.81 (1H, C$_\alpha$H), 3.67 (1H, C$_\alpha$H) for Gly-4; 8.00 (1H, s, CONH), 4.37 (1H, C$_\alpha$H), 3.34 (1H, C$_\beta$H), 3.20 (1H, C$_\beta$H) for Dap-5; 8.00 (1H, CONH of Dap-4-nitro-hippuryl); 3.92 (2H, CH$_2$), 9.05 (1H, s, CONH), 8.08 (2H, 2×Ar—H at ortho position to CONH), 8.31 (2H, 2×Ar—H at meta position to CONH) for 4-nitro-hippuryl group; 8.16 (1H, s, CONH), 4.53 (1H, C$_\alpha$H), 2.95 (1H, C$_{\beta H_1}$), 2.75 (1H, C$_{\beta H_1}$), 7.18-7.23 (5H, m, 5×Ar—H) for Phe-6; 8.29 (1H, s, CONH), 4.35 (1H, C$_\alpha$H), 1.85 (1H, C$_{\beta H_1}$), 1.73 (1H, C$_{\beta H_1}$), 2.37 (2H, C$_\gamma$H$_2$), 2.00 (3H, SCH3) for Met-7; 7.95 (1H, s, CONH), 4.46 (1H, C$_\alpha$H), 2.85 (1H, C$_{\beta H_1}$), 2.66 (1H, C$_{\beta H_1}$), 6.60 (2H, 2×Ar—H, meta to OH), 6.97 (2H, 2×Ar—H, ortho to OH) for Tyr-8; 8.17 (1H, s, CONH), 4.44 (1H, C$_\alpha$H), 2.95 (1H, C$_{\beta H_1}$), 2.80 (1H, C$_{\beta H_1}$), 7.18-7.23 (5H, m, 5×Ar—H) for Phe-9 (C-terminus); 8.04 (1H, s, CONHCH$_2$, 3.32 (1H, C$_\alpha$H, alpha from NH), 3.23 (1H, C$_\alpha$H), 2.63 (2H, C$_\beta$H$_2$). $^{13}$C NMR (300 MHz, DMSO, ppm) 119.40 (C, ortho to OH), 122.20 (C), 124.60 (1C, ortho to CH$_2$), 47.20 (C(H$_2$)) for 2,3-dihydroxybenzyl group on N$^\alpha$ of Arg-1 (N-terminus); 61.80 (C$_\alpha$), 32.10 (C$_\beta$), 27-28 (C$_\gamma$), 43.60 (C$_\delta$) for Arg-1; 55.80 (C$_\alpha$), 32.10 (C$_\beta$), 27-28 (C$_\gamma$), 43.60 (C$_\delta$) for Arg-2 55.30 (C$_\alpha$), 31.30 (C$_\beta$), 34.30 (C$_\gamma$) for Gln-3; 45.10 (C$_\alpha$) for Gly-4; 55.30 (C$_\alpha$), 43.60 (C$_\beta$) for Dap-5; 46.30 (C(H$_2$)), 132.00 (2×C in aromatic ring at ortho position to CONH), 126.70 (2×C in aromatic ring at meta position to CONH) for 4-nitro-hippuryl group; 57.40 (C$_\alpha$), 40.20 (C$_\beta$), 132.3 (2C in aromatic ring), 131.3 (2C in aromatic ring), 129.3 (1C in aromatic ring) for Phe-6; 55.30 (C$_\alpha$), 35.40 (C$_\beta$), 32.50 (C$_\gamma$), 17.70 (C$_\delta$) for Met-7; 57.20 (C$_\alpha$), 39.80 (C$_\beta$), 117.90 (C, meta to OH), 133.20 (C, ortho to OH) for Tyr-8; 57.00 (C$_\alpha$), 41.10 (C$_\beta$), 132.3, 131.3, 129.3 (benzene ring) for Phe-6; (C-terminus); 41.20 (C$_\alpha$, alpha from NH), 39.80 (C$_\beta$). ESI-MS (m/z) calculated for $C_{72}H_{96}N_{20}O_{17}S_2$ (M$^+$) 1577.79. found 1577.70.

Synthesis of compound G. 2.5 g of Tentagel resin consensus peptide-2 was mixed with 0.84 g (6 mmol) of 2,3-dihydroxybenzaldehyde in 22 mL of DMF/TMOF/MeOH/AcOH (10:10:1:1). NaCNBH$_3$ (0.32 g, 6 mmol) was added in one portion to the above mixture. The sealed tube was shaken for 4 h at room temperature, and the solution was then drained from the reaction vessel. The resin was washed successively with DMF (3×20 mL), DMF/H$_2$O (1/1, 3×20 mL), H$_2$O (3×20 mL), MeOH/CH$_2$Cl$_2$ (1/1, 3×20 mL), CH$_2$Cl$_2$ (3×20 mL), and DMF (3×20 mL). The resin was subsequently exposed to a second cycle of the above protocol. All the side chain protecting groups were removed by exposing the resin to 25 mL of TFA:H$_2$O:TIS (95:2.5:2.5) for 2 h at ambient temperature. The peptide-nonpeptide conjugates were cleaved from the Tentagel resin with 10 mM DTT in 50 mM Tris, pH 7.5 (3•×15 mL for 3 h each), and the filtered crude solution was purified by RP-HPLC. The eluent (peptide-containing 0.1% TFA solution in H$_2$O—CH$_3$CN) was lyophilized to give 26 mg of Compound G (white solid). $^1$H NMR (300 MHz, DMSO, ppm) 6.68 (2×1H, Ar—H, ortho to OH), 6.59 (2×1H, Ar—H), 6.62 (2×1H, Ar—H, ortho to CH$_2$), 3.99 (2H, 2×(0.5×CH$_2$)), 3.93 (2H, 2×(0.5×CH$_2$)) for two 2,3-dihydroxybenzyl groups on N$^\alpha$ atom of Arg-1 (N-terminus); 3.81 (1H, C$_\alpha$H), 1.71 (2H, C$_\beta$H$_2$), 1.55 (2H, C$_\gamma$H$_2$), 3.12 (2H, C$_\delta$H$_2$), 7.45 (N$^\epsilon$H) for Arg-1; 7.95 (1H, s, CONH), 4.35 (1H, C$_\alpha$H), 1.73 (2H, C$_\beta$H$_2$), 1.48 (2H, C$_\gamma$H$_2$), 3.05 (2H, C$_\delta$H$_2$), 7.36 (N$^\epsilon$H) for Arg-2; 8.05 (1H, s, CONH), 4.27 (1H, C$_\alpha$H), 1.88 (1H, C$_{\beta H_1}$), 1.76 (1H, C$_{\beta H_1}$), 2.13 (2H, C$_\gamma$H$_2$) for Gln-3; 8.15 (1H, s, CONH), 3.81 (1H, C$_\alpha$H), 3.67 (1H, C$_\alpha$H) for Gly-4; 8.00 (1H, s, CONH), 4.37 (1H, C$_\alpha$H), 3.34 (1H, C$_\beta$H), 3.20 (1H, C$_\beta$H) for Dap-5; 8.00 (1H, CONH of Dap-4-nitro-hippuryl); 3.92 (2H, CH$_2$), 9.05 (1H, s, CONH), 8.08 (2H, 2×Ar—H at ortho position to CONH), 8.31 (2H, 2×Ar—H at meta position to CONH) for 4-nitro-hippuryl group; 8.16 (1H, s, CONH), 4.53 (1H, C$_\alpha$H), 2.95 (1H, C$_{\beta H_1}$), 2.75 (1H, C$_{\beta H_1}$), 7.18-7.23 (5H, m, 5×Ar—H) for Phe-6; 8.29 (1H, s, CONH), 4.35 (1H, C$_\alpha$H), 1.85 (1H, C$_{\beta H_1}$), 1.73 (1H, C$_{\beta H_1}$), 2.37 (2H, C$_\gamma$H$_2$), 2.00 (3H, SCH$_3$) for Met-7; 7.95 (1H, s, CONH), 4.46 (1H, C$_\alpha$H), 2.85 (1H, C$_{\beta H_1}$), 2.66 (1H, C$_{\beta H_1}$), 6.60 (2H, 2×Ar—H, meta to OH), 6.97 (2H, 2×Ar—H, ortho to OH) for Tyr-8; 8.17 (1H, s, CONH), 4.44 (1H, C$_\alpha$H), 2.95 (1H, C$_{\beta H_1}$), 2.80 (1H, C$_{\beta H_1}$), 7.18-7.23 (5H, m, 5×Ar—H) for Phe-9 (C-terminus); 8.04 (1H, s, CONHCH$_2$, 3.32 (1H, C$_\alpha$H, alpha from NH), 3.23 (1H, C$_\alpha$H), 2.63 (2H, C$_\beta$H$_2$). $^{13}$C NMR (300 MHz, DMSO, ppm) 117.60 (C, ortho to OH), 122.10 (C), 123.50 (1C, ortho to CH$_2$), 47.20 (C(H$_2$)) for 2,3-dihydroxybenzyl group on N$^\alpha$ atom of Arg-1 (N-terminus); 61.80 (C$_\alpha$), 32.10 (C$_\beta$), 27-28 (C$_\gamma$), 43.60 (C$_\delta$) for Arg-1; 55.20 (C$_\alpha$), 32.10 (C$_\beta$), 27-28 (C$_\gamma$), 43.60 (C$_\delta$) for Arg-2 55.30 (C$_\alpha$), 31.30 (C$_\beta$), 34.30 (C$_\gamma$) for Gln-3; 45.10 (C$_\alpha$) for Gly-4; 55.30 (C$_\alpha$), 43.60 (C$_\beta$) for Dap-5; 46.30 (C(H$_2$)), 132.00 (2×C in aromatic ring at ortho position to CONH), 126.70 (2×C in aromatic ring at meta position to CONH) for 4-nitro-hippuryl group; 57.40 (C$_\alpha$), 40.20 (C$_\beta$), 132.3 (2C in aromatic ring), 131.3 (2C in aromatic ring), 129.3 (1C in aromatic ring) for Phe-6; 55.30 (C$_\alpha$), 35.40 (C$_\beta$), 32.50 (C$_\gamma$), 17.70 (C$_\delta$) for Met-7; 57.20 (C$_\alpha$), 39.80 (C$_\beta$), 117.90 (C, meta to OH), 133.20 (C, ortho to OH) for Tyr-8; 57.00 (C$_\alpha$), 41.10 (C$_\beta$), 132.3, 131.3, 129.3 (benzene ring) for Phe-6; (C-terminus); 41.20 (C$_\alpha$, alpha from NH), 39.80 (C$_\beta$). ESI-MS (m/z) calculated $C_{79}H_{102}N_{20}O_{19}S_2$ (M$^+$) 1699.91. found 1699.40.

Protein Kinase C Assays. The peptides Ac-Ser-Phe-Arg-Arg-Arg-Arg-NH$_2$ (for PKC α, β and γ) and Ac-Pro-Arg-Lys-Arg-Glu-Gly-Ser-Val-Arg-Arg-Arg-Val-NH$_2$ (for PKC δ, ε, θ, η, τ, and ζ) were used as substrates.

Protein Kinase C Assays. The peptides Ac-Ser-Phe-Arg-Arg-Arg-Arg-NH$_2$ (for PKC α, β and γ) (SEQ ID NO:15) and Ac-Pro-Arg-Lys-Arg-Glu-Gly-Ser-Val-Arg-Arg-Arg-Val-NH$_2$ (for PKC δ, ε, θ, η, τ and ζ) (SEQ ID NO:16) were used as substrates.

Protein kinase C δ screen. 20 µL of 12.5 µM peptide inhibitor candidate (from each well of libraries I, II, and III) was added to individual wells of 96 multiwell assay plates containing 20 µL assay buffer [62.5 mM HEPES (pH 7.5), 50 µM substrate, 30 mM MgCl$_2$.6H$_2$O, 1.0 mM EGTA.Na, PS (50 µg/mL), DAG (10 µg/mL) and 300 µM cold ATP supplemented with 55 µCi/96-well plate (0.5 µCi/well) [γ$^{-33}$ P] ATP for radioactive detection. 10 µL of an enzyme buffer solution, containing 20 mM Tris (pH 7.5), PKCδ (10 ng/well), 0.5 mM DTT, 0.375 mg/mL BSA, and 0.5 mM EDTA 4Na.2H$_2$O, was added to initiate the reaction. Total reaction volume in each well was 50 µL. After a 10-min incubation at 30° C., 100 µL of 6% phosphoric acid was added to each well to stop the reaction (total volume: 150 µL). Following an additional 5 min incubation at ambient temperature, 75 µL from each reaction well was transferred into each well of a Unifilter (P81 cellulose phosphate paper) assay plate and washed four times with 0.1% phosphoric acid in water. ScintiSafe 30% solution was added to each well and $^{33}$P-incorporation measured by scintillation counting with a 1420 MICROBETA® TriLux & MicroBeta JET (Perkin Elmer). Lead compounds from the library were combined into a single 96 well plate and re-assayed as described above in order to identify the best inhibitor.

Protein Kinase C screen. 20 µL of 12.5 µM peptide inhibitor candidate (from each well of libraries I, II, and III) was added to individual wells of 96 multiwell assay plates containing 20 µL assay buffer [62.5 mM HEPES (pH 7.5), 50 µM substrate, 30 mM MgCl$_2$.6H$_2$O, 1.0 mM EGTA.Na, PS (50 µg/mL), and 300 µM cold ATP supplemented with 75 µCi/96-well plate (0.75 µCi/well) [γ-$^{33}$P] ATP for radioactive detection. 10 µL of an enzyme buffer solution, containing 20 mM Tris (pH 7.5), PKC (10 ng/well), 0.5 mM DTT, 0.375 mg/mL BSA, and 0.5 mM EDTA 4Na 2H$_2$O, was added at last to initiate the reaction. Total reaction volume in each well was 50 µL. After a 10-min incubation at 30° C., 100 µL of 6% phosphoric acid was added to each well to quench the reaction (total volume: 150 µL). Following an additional 5 min incubation at ambient temperature, 75 µL from each reaction well was transferred into each well of a Unifilter (P81 cellulose phosphate paper) assay plate and washed four times with 0.1% phosphoric acid in water. ScintiSafe 30% solution was added to each well and $^{33}$P-incorporation measured by scintillation counting with a 1420 MICROBETA® TriLux & MicroBeta JET (Perkin Elmer). Lead compounds from the library were combined into a single 96 well plate and re-assayed as described above in order to identify the best inhibitor.

IC$_{50}$ determinations of resynthesized inhibitor leads for individual PKC isoforms. Assays were performed in triplicate at pH 7.5 and thermostatically maintained at 30° C. using a Boekel constant temperature device. Protein kinase C α, β-I and γ: 20 µL assay buffer solution, containing 62.5 mM Hepes (pH 7.5), 50 µM Ac-Ser-Phe-Arg-Arg-Arg-Arg-NH$_2$, CaCl$_2$.2H$_2$O (2.0 mM) (SEQ ID NO:15), MgCl$_2$.6H$_2$O (30.0 mM), EGTA.Na (1.0 mM), PS (50.0 µg/mL), DAG 10 µg/mL, cold ATP (300 µM), supplemented with 55 µCi/plate [γ-$^{33}$P] ATP for radioactive detection, were added to 20 µL of a solution containing inhibitor lead at various concentrations (2, 4, 8, 16, 32, 64, 128, 256, 512 nM). 10 µL enzyme buffer solution containing 20 mM Tris (pH 7.5), PKC isoform (~10 ng/well), 0.5 mM DTT, BSA (375 µg/mL), and EDTA.4Na.2H$_2$O (0.5 mM) was added to initiate the reaction. Reactions and their work-up were carried out as described above. The IC$_{50}$ values for pure compounds as inhibitors were calculated based on the experimental data using GraFit (Erithacus Software Limited). Protein kinase C, δ, ε, θ, and η: As described for PKC α, β, and γ except that the assay was performed in the absence of CaCl$_2$. Protein kinase C τ and ζ: As described for PKC α, β, and γ except that the assay was performed in the absence of CaCl$_2$ and DAG.

K$_i$ determinations. 20 µL of inhibitor ([F]=0, 9, 18, 36 and 54 nM) was added to a 20 µL assay buffer containing 62.5 mM HEPES (pH 7.5), peptide substrate (concentrations=5, 10, and 20 µM), 30 mM MgCl$_2$.6H$_2$O, 1.0 mM EGTA.Na, PS (50 µg/mL), DAG (10 µg/mL; note: DAG was not added for the PKC ζ assay), and 300 µM cold ATP supplemented with 1.0 µCi/well [γ-$^{33}$P] ATP for radioactive detection. 10 µL enzyme diluted buffer containing 20 mM Tris (pH 7.5), PKC (10 ng/well), 0.5 mM DTT, BSA (375 µg/mL) and 0.5 mM EDTA.4Na.2H$_2$O was added to initiate the reaction. Total reaction volume in each well was 50 µL. All the wells were tested in the same plate and each concentration was tested in triplicate. Subsequent assay workup and scintillation counting were performed as described above. Double reciprocal plots were obtained at different concentrations of substrates. K$_i$ values were calculated using Enzyme Kinetics, SigmaPlot (SPSS Inc.).

Results And Discussion

At least two members of the PKC family of protein kinases have been implicated as enzymes that indirectly regulate cofilin phosphorylation status, which in turn controls the level of actin polymerization at the leading edge of actively motile cells. Studies with phorbol myristic acid (PMA)-exposed neutrophils suggest that PKC δ may be involved in a pathway that mediates the dephosphorylation of cofilin (Zhan et al., 2003; Djafarzadeh and Niggli, 1997). However, this conclusion was reached using an array of PKC inhibitors that display overlapping selectivities for the individual PKC isoforms. PKC ζ has also been implicated as a potential regulatory element of cofilin phosphorylation status since this isoform binds tightly to the LIM domain of the LIM-kinase (Kuroda et al., 1996). Although it is unknown whether PKC ζ actively phosphorylates the LIM-kinase, several studies have implicated the ζ isoform in the pathways that drive motility in neutrophils and adenocarcinoma cells (Laudanna et al., 1998; 2003). As part of our interest in defining the pathways that control the earliest events in cell motility, we required access to potent, yet highly selective, inhibitors for PKC δ and ζ.

We have developed a synthesis protocol that converts consensus sequence peptides into high affinity ligands that block protein-protein interactions. This strategy has furnished ligands for the SH2 domain from Lck (Yeh et al., 2001; Lee and Lawrence, 1999; 2000), the protein phosphatase PTP1B (Xie et al., 2003; Shen et al., 2001; Sun et al., 2003), and most recently PKC α (Lee et al., 2004). The ligand for the latter serves as a potent and highly selective inhibitor of PKC α-catalyzed phosphorylation of substrates. However, to the best of our knowledge, active site-directed inhibitors that display a special affinity for specific members of the atypical or novel PKC subfamilies have not been described. We report herein the acquisition of high affinity inhibitors with remarkable selectivity for the δ and ζ isoforms of PKC.

Figure 6:
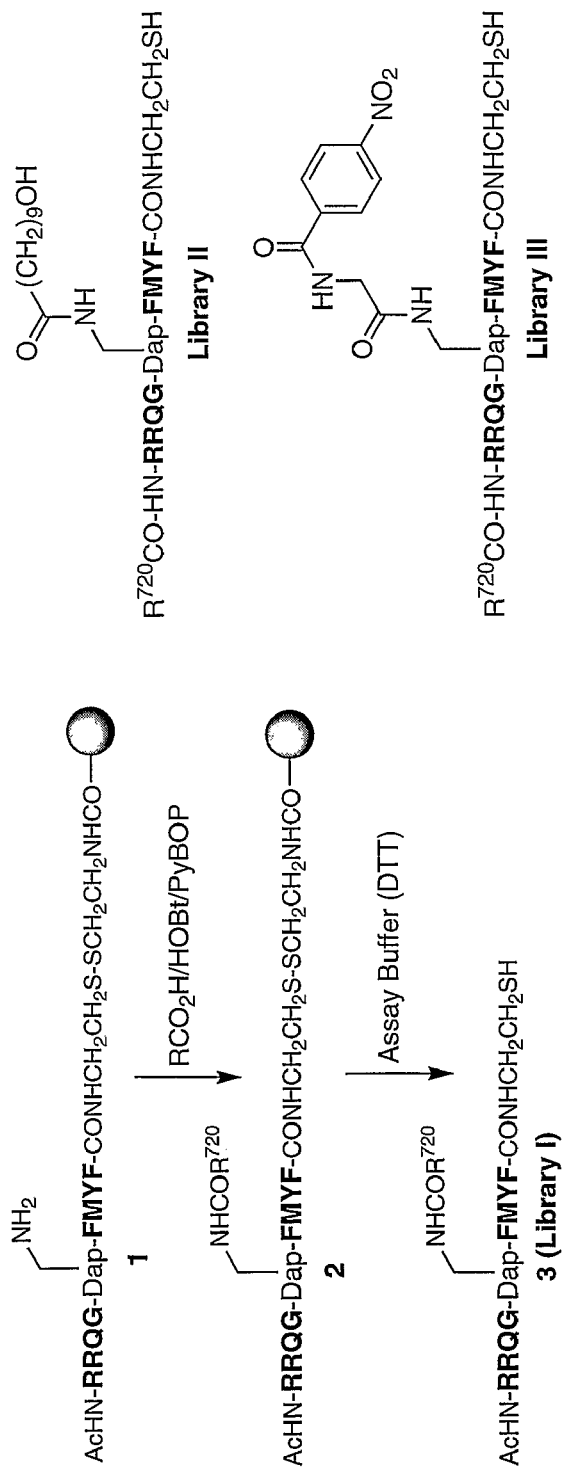
FIG. 6 shows a general scheme for the introduction of molecular diversity at specific amino acid residues on the consensus sequence. The Dap residue [(L)-2,3-diaminopropionic acid] side chain serves as a handle for the assembly of molecular diversity.

As a starting point, we employed a slightly modified and amalgamated version of the previously described consensus active site recognition sequences (Nishikawa et al., 1997) of PKC δ and ζ: Arg-Arg-Gln-Gly-Dap-Phe-Met-Tyr-Phe [where Dap=(L)-2,3-diaminopropionic acid] (SEQ ID NO:17). In general, peptides containing consensus sequences bind modestly, at best, to their intended protein targets. Indeed, the simple diacetylated consensus derivative A exhibits an IC$_{50}$ of 50 µM for PKC δ and 80 µM for PKC ζ. We reasoned that there is a good likelihood that unnatural substituents, positioned off the consensus sequence scaffold, might engage in high affinity interactions with subsites that lie adjacent to the active site region. In order to explore this notion, the consensus peptide 1 on the disulfide-linked Tenta-gel resin was prepared as shown in FIG. 6. Following solid phase peptide synthesis, the amine side chain of the Dap residue was deprotected and the peptide-S-S-resin subsequently added to individual wells of solvent-resistant MUL-TISCREEN® 96-well filter plates. Each well contained 1 of 720 different, structurally diverse (hydrophobic, hydrophilic, cyclic, acyclic, charged, uncharged, etc), commercially available carboxylic acids. Condensation of the Dap amine side chain with the various acids furnished the amides 2 (FIG. 7). In addition, the corresponding free amine (non-acylated) derivative 1 was included in the peptide library. The entire synthetic strategy is easily automated using a liquid handling robot. The peptides were side chain-deprotected, released from the resin with assay buffer (which contains DTT), and collected in an assay-ready form for subsequent screening [compounds 3 ("Library I")]. The latter was performed in a 96 well plate format versus PKC ζ. Two lead inhibitors were identified, designated as compounds B (IC$_{50}$=0.85±0.2 µM) and C (IC$_{50}$=6.4±0.3 µM) (FIG. 7). The IC$_{50}$ value of the former is approximately 100-fold better than that of the diacetylated parent peptide A. However, neither B nor C displays significant (<10-fold) selectivity for PKC ζ versus a subset of other PKCs (data not shown).

Figure 8:
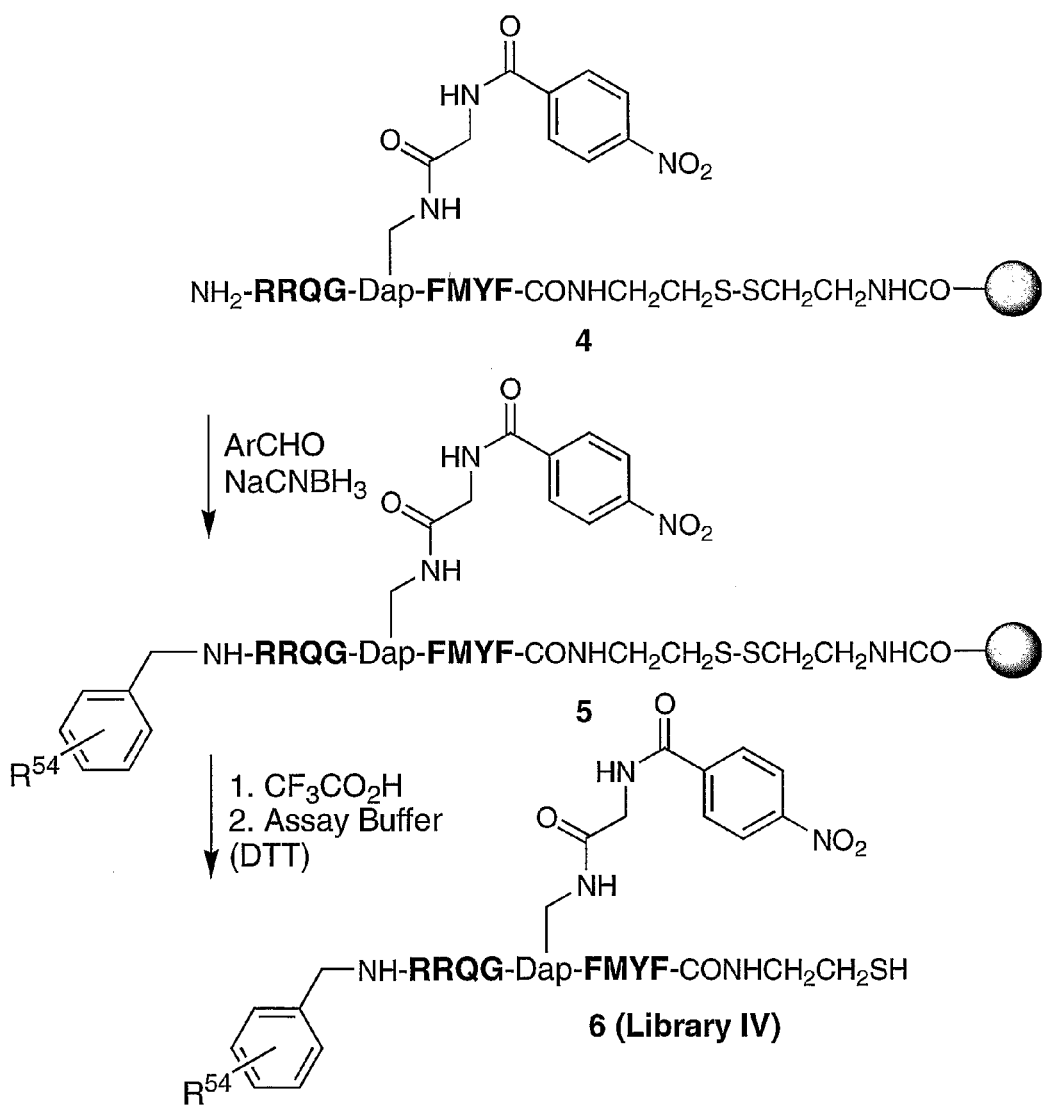
FIG. 8 shows a reductive alkylation protocol that furnishes molecular diversity at the N-terminus of peptide 6 while retaining a net positive charge at physiological pH. The latter is an important recognition for the β, δ, and ζ isoforms of PKC within the context of the p-nitrobenzoyl-substituted peptide. The molecules illustrated in FIG. 8 comprise the amino acid sequence set forth in SEQ ID NO:17.

In order to further augment potency and potentially enhance selectivity, we subsequently applied the synthetic protocol outlined above to a second site on the peptide framework, namely the N-terminus of compounds B and C, by replacing the acetyl moiety with 720 distinct acyl groups (Libraries II and III, respectively). The sublibrary from B produced leads that display only minor improvements relative to the parent compound B for both PKC δ and ζ. By contrast, leads derived from compound C (e.g. compound D) exhibit an enhanced affinity for δ and ζ relative to the other PKC isoforms. Unexpectedly, of all of these leads, the most potent inhibitor for both PKC δ and ζ proved to be the nonacylated free amine E (FIG. 7). This compound displays an $IC_{50}$ of 22±3 nM for PKC ζ, 25±2 nM for PKC δ, and 8.0±0.5 nM for PKC β (Table 2). In addition, compound E is an exceedingly ineffective inhibitor for all the other PKC family members. Since the free N-terminus is undoubtedly charged under physiological conditions, these results imply that β, δ, and ζ enjoy a special affinity for the ammonium ion at this position on the p-nitrobenzoyl-substituted peptide. The emergence of the 100-fold selectivity for β, δ, and ζ versus the other PKC isoforms suggests that compound E has access to an active site region that is not structurally conserved throughout the PKC family. Consequently, the introduction of additional structural elements at this position could further enhance inhibitory potency and selectivity for the target PKC δ and ζ isoforms. We chose a reductive alkylation protocol as a means to promulgate diversity while retaining the positively charged nature of the ammonium ion (FIG. 8).

TABLE 2

$IC_{50}$ values (μM) of compounds E, F, and G for the conventional, novel, and atypical PKC isoforms.

| PKC Isoforms | Inhibitor $IC_{50}$ (μM) | | | |
|---|---|---|---|---|
| | Compound E | Selectivity | Compound F | Compound G |
| α | 3.1 ± 0.2 | 387 | 17.0 ± 0.4 | 47.5 ± 1.5 |
| βI | 0.0080 ± 0.0005 | 1 | 3.1 ± 0.2 | 5.5 ± 0.1 |
| γ | 4.4 ± 0.3 | 550 | 9.0 ± 0.3 | 38.2 ± 1.2 |
| δ | 0.025 ± 0.002 | 3.1 | 0.018 ± 0.002 | 5.2 ± 0.1 |
| ε | 2.3 ± 0.1 | 287 | 8.8 ± 0.6 | 34.5 ± 0.9 |
| θ | 14.2 ± 0.6 | 1775 | 13.7 ± 0.6 | 16.7 ± 0.4 |
| η | 13.2 ± 0.8 | 1650 | 12.3 ± 0.6 | 15.3 ± 0.6 |
| ι | 0.75 ± 0.11 | 94 | 0.46 ± 0.03 | 11.2 ± 0.4 |
| ζ | 0.022 ± 0.003 | 2.8 | 3.6 ± 0.2 | 0.00075 ± 0.0003 |

The peptide-resin 4 was dispensed into 54 wells, where each well contained $NaCNBH_3$ and one of 54 different aromatic aldehydes. Reductive alkylation furnished the library of monoalkylated compounds 5. The latter was then sequentially exposed to TFA to remove the side chain protecting groups and assay buffer to effect cleavage of the modified peptides from the resin (6, "Library IV"). The initial screen was performed against PKC δ, which furnished compound F as the lead (FIG. 7). The 2,3-dihydroxy substitution pattern appears to be critical since other substitution patterns contained in the library (2,5-dihydroxy and 2,4-dihydroxy) do not display any inhibitory activity in the initial screen (at a crude concentration of 200 nM). Compound F exhibits an $IC_{50}$ of 18±2 nM and a $K_i$ of 8±1 nM with a competitive inhibition pattern versus peptide substrate in the PKC δ-catalyzed reaction. Furthermore, this inhibitor displays remarkable selectivity versus other members of the PKC family, including the conventional (α, 944-fold; β-I, 172-fold; γ, 500-fold), atypical (ζ, 200-fold), and novel (ε, 489-fold; η, 683-fold; θ, 761-fold) isoforms. Curiously, selectivity is less substantial (26-fold) against the atypical τ isoform. We also prepared compound G, the doubly alkylated analogue of F (FIG. 7). Much to our surprise, we found that the addition of a second aryl group on the N-terminus dramatically inverted selectivity, producing a highly selective inhibitor for PKC ζ (Table 2). Compound G is a competitive inhibitor versus peptide substrate ($K_i$=3.9±0.2 nM) with a selectivity against the other PKC isoforms that ranges from 700-fold to greater than 6,000-fold. To the best of our knowledge, F and G are the first examples of highly selective inhibitors for non-conventional PKCs.

A wide variety of PKC inhibitors have been described during the last two decades. Given the high active site sequence homology among the various PKC isoforms, it is not surprising that the overwhelming majority of these inhibitors display little selectivity for the individual PKC isoforms. However, a few isoform-selective inhibitors have been identified. For example, the natural product rottlerin exhibits a 10-fold preference for PKC δ versus the α and β isoforms and a somewhat higher selectivity versus the other PKC family members (Table 3)(Gschwendt et al., 1994). The bisindolyl-maleimide Gö6850, and structurally related analogues, appear to display a modest preference for the conventional isoforms, although a complete analysis with all the available PKC isoforms has not been reported (Martiny-Baron et al., 1993). A series of inhibitors from Roche (e.g. Ro320432) exhibit a slight selectivity for PKC α (Wilkinson et al., 1993). By contrast, investigators from Lilly described the first example of a PKC inhibitor that shows a special affinity for a single isoform (PKC β) versus the other PKC family members (Jirousek et al., 1996). Although LY333531 does not distinguish between the two PKC β slice variants (I and II), this inhibitor does exhibit a clear preference for β that ranges from 10-fold versus η to more than $10^5$-fold versus ζ. All of the inhibitors described in Table 3, with the exception of compounds F, G, and H, are directed to the ATP binding site. Although the $IC_{50}$ values for the ATP analogues are in the low nM range, the actual inhibitory efficacy of these compounds is diminished by the fact that they must compete with the high intracellular concentration (>1 mM) of ATP (Lawrence and Niu, 1998).

TABLE 3

Selectivity of active site-directed PKC inhibitors. The fold-selectivity of the most potently inhibited isoform by a given inhibitor is assigned an arbitrary value of 1 (the IC50 or Ki is provided in bold face in parentheses).

| PKC Isoforms | Fold selectivity ($IC_{50}$) | | | | | | |
|---|---|---|---|---|---|---|---|
| | Rottlerin[a] | Gö6850[b] | Ro320432[c] | LY333531[d] | Compound F | Compound G | Compound H[e] |
| α | 10 | 1 (8.4 nM) | 1 (9 nM) | 77 | 944 | 6333 | 1 (0.8 nM) |
| β1 | 14 | 2 | 3 | 1 (4.7 nM) | 172 | 730 | 385 |
| γ | 13 | NR | 4 | 85 | 500 | 5093 | 580 |
| δ | 1 (3 μM) | 25 | NR | 53 | 1 (18 nM) | 693 | 2730 |

TABLE 3-continued

Selectivity of active site-directed PKC inhibitors. The fold-selectivity of the most potently inhibited isoform by a given inhibitor is assigned an arbitrary value of 1 (the IC50 or Ki is provided in bold face in parentheses).

| PKC Isoforms | Fold selectivity (IC$_{50}$) | | | | | | |
|---|---|---|---|---|---|---|---|
| | Rottlerin[a] | Gö6850[b] | Ro320432[c] | LY333531[d] | Compound F | Compound G | Compound H[e] |
| ε | 33 | 16 | 12 | 128 | 489 | 4600 | 600 |
| θ | Not Reported (NR) | NR | NR | NR | 761 | 2227 | 1210 |
| η | 27 | NR | NR | 11 | 683 | 2040 | 1310 |
| ι | NR | NR | NR | NR | 26 | 1493 | 940 |
| ζ | 33 | 690 | NR | >10$^5$ | 200 | 1 (7.5 nM) | 640 |

[a]Values taken from Gschwendt et al., 1994.
[b]Values taken from Martiny-Baron et al., 1993.
[c]Values taken from Wilkinson et al, 1993.
[d]Values taken from Jirousek et al., 1996.
[e]Values taken from Lee et al., 2004.

A few alternative approaches, which do not target the ATP binding site, have been described for the PKC enzyme family. Mochley-Rosen and her colleagues reported the use of peptides that block the translocation of specific PKC isoforms to their designated intracellular sites (Mochly-Rosen and Kauvar, 2000). For example, a C2 region peptide fragment of PKC β compromises the ability of this specific isoform to bind to its receptor for activated C kinase (RACK) and thereby precludes its translocation by phorbol ester (Ron et al., 1995). These investigators have described several other isoform-selective translocation inhibitors as well (Mochly-Rosen and Kauvar, 2000). Although the response of cells to these translocation inhibitors is impressive, the in vitro binding affinities and isoform selectivities of these peptides have not been reported. Consequently, it is not possible to compare the relative efficacy of these derivatives with those listed in Table 3.

Genetic approaches, such as antisense or siRNA, can be exquisitely selective with respect to the down-regulation of specific protein targets. Indeed, aprinocarsen, a 19-mer phosphorothioate oligodeoxynucleotide, inhibits the expression of the PKC α isoform and is currently undergoing clinical trials (Lahn et al., 2004a; 2004b; Lahn and Sundell, 2004). Strategies that target the message of specific proteins have the potential to be enormously beneficial in a therapeutic setting. However, as reagents, antisense or siRNA are unable to address issues related to protein activity and cellular response with a high level of temporal precision. By contrast, reagents that operate at the protein level can rapidly inhibit enzymatic activity in the context of a given cellular behavior (e.g. motility, division, etc.).

Active site-directed PKC inhibitors that are competitive with protein substrate have also been reported. However, these reagents, which are typically peptides, are nonselective with respect to individual isoforms (Borowski et al., 2000; Ward et al., 1995; Eichholtz et al., 1993; Ricouart et al., 1989; Charp et al., 1988; House and Kemp, 1987; 1990; Kemp et al., 1991. By contrast, the peptide analogues derived from the library strategy described herein display an isoform selectivity dramatically better than any active site-targeted inhibitors reported to date. With these inhibitory agents in hand, studies are now in progress to determine which specific PKC inhibitors influence the signaling pathways that control cellular motility.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An inhibitor of a protein kinase Cα (PKCα), the inhibitor comprising

A-Ala-Arg-Arg-X-B-Hyd-C-D- (SEQ ID NO:1), where A=AcHN—,

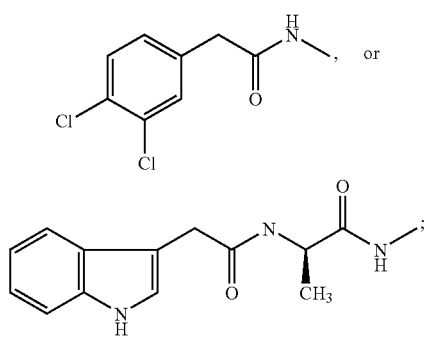

X=any amino acid; B=Ala or a diaminopropionic acid (Dap) derivative having the formula

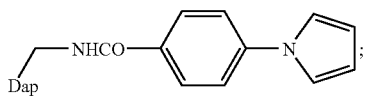

Hyd=Phe, Leu or Ile; C=Ara or Lys: and D=Ala or a Dap derivative having the formula

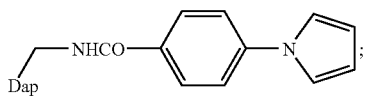

2. The inhibitor of claim 1, wherein the PKCα is a human PKCα.

3. An inhibitor of a protein kinase Cα (PKCα), the inhibitor comprising

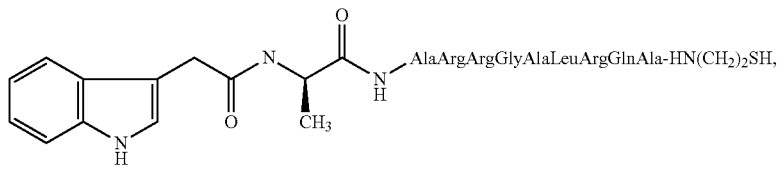
(SEQ ID NO: 2)

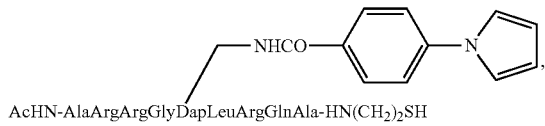
(SEQ ID NO: 2)

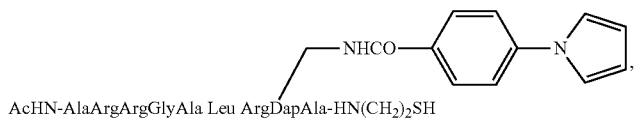
(SEQ ID NO: 2)

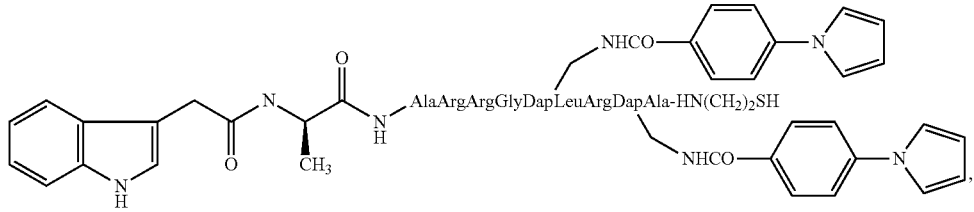
(SEQ ID NO: 2)

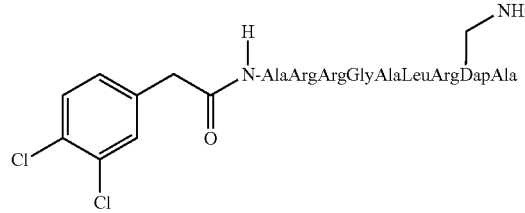
(SEQ ID NO: 2), or

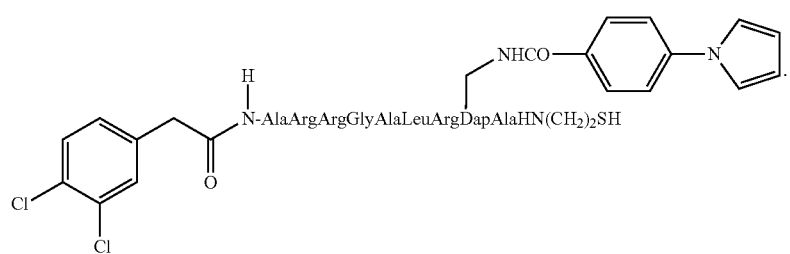
(SEQ ID NO: 2).

4. The inhibitor of claim 1, having an $IC_{50} < 50$ μM for the PKCα.
5. The inhibitor of claim 1, having an $IC_{50} < 10$ μM for the PKCα.
6. The inhibitor of claim 1, having an $IC_{50} < 1$ μM for the PKCα.
7. The inhibitor of claim 1, wherein the inhibitor has an $IC_{50}$ for the PKCα<0.1 that of any other PKC isoform.
8. The inhibitor of claim 1, wherein the inhibitor has an $IC_{50}$ for the PKCα<0.01 that of any other PKC isoform.
9. The inhibitor of claim 3, comprising

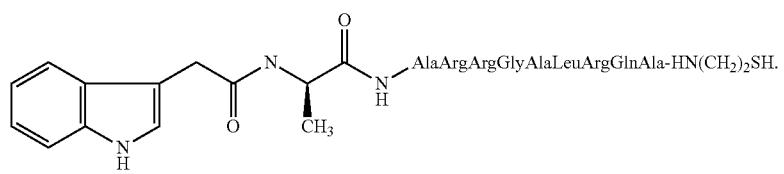

10. The inhibitor of claim 3, consisting of

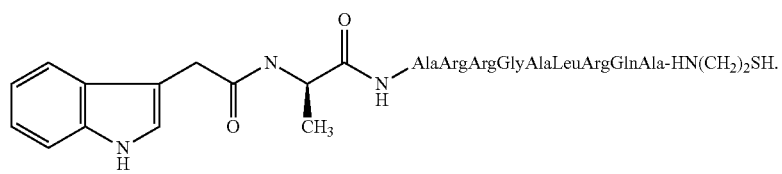

11. The inhibitor of claim 3, comprising

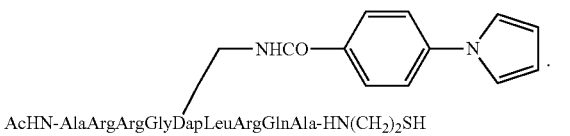
(SEQ IS NO: 2)

12. The inhibitor of claim 3, consisting of

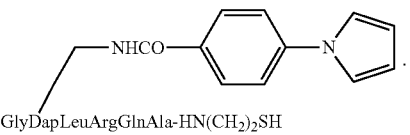
(SEQ IS NO: 2)

13. The inhibitor of claim 1, comprising
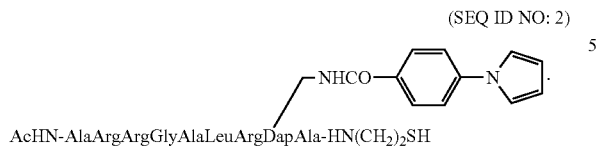
(SEQ ID NO: 2)
14. The inhibitor of claim 1, consisting of
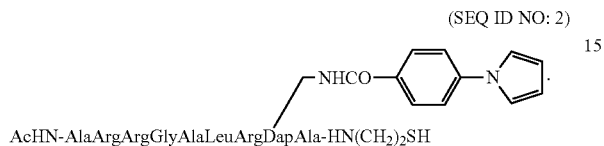
(SEQ ID NO: 2)
15. The inhibitor of claim 1, comprising
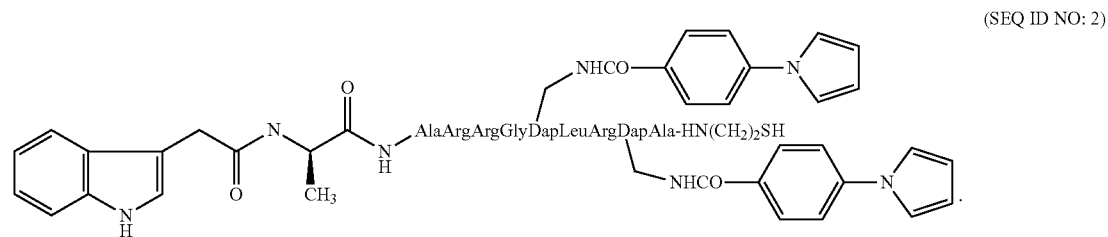
(SEQ ID NO: 2)
16. The inhibitor of claim 1, consisting of
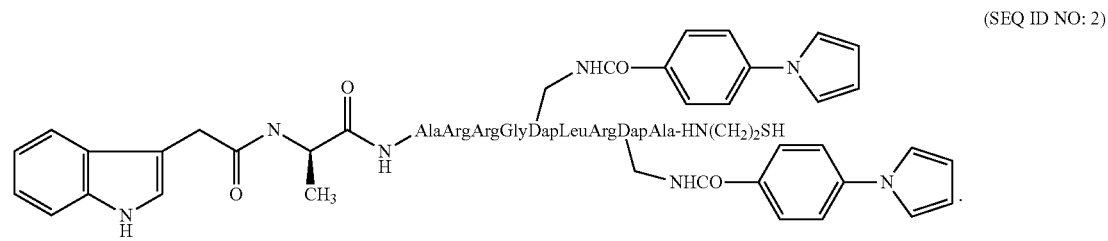
(SEQ ID NO: 2)
17. The inhibitor of claim 1, comprising
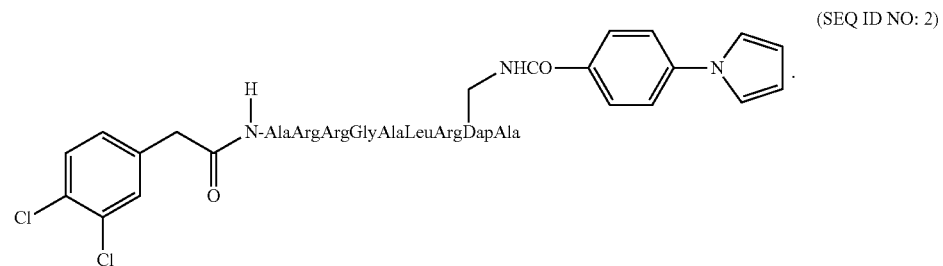
(SEQ ID NO: 2)
18. The inhibitor of claim 1, consisting of

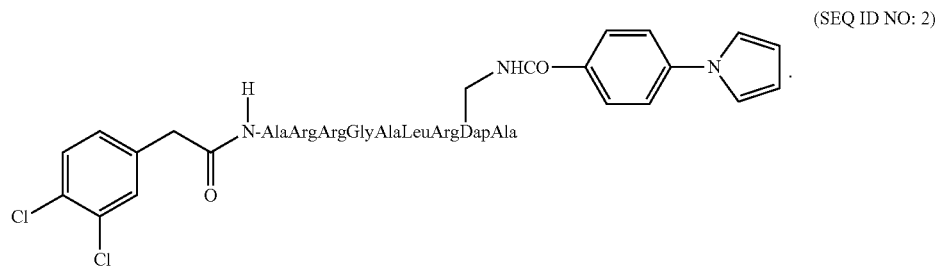
(SEQ ID NO: 2)
19. The inhibitor of claim 1, comprising
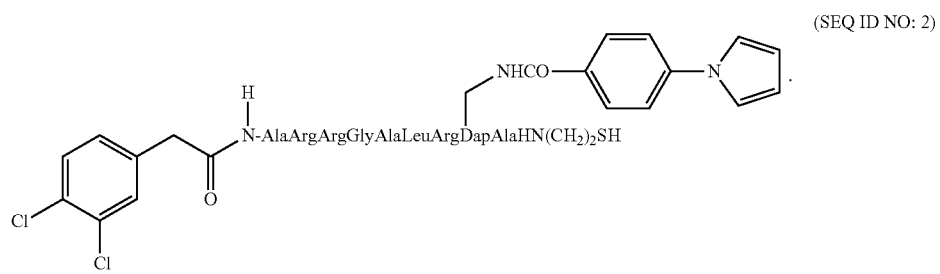
(SEQ ID NO: 2)
20. The inhibitor of claim 1, consisting of
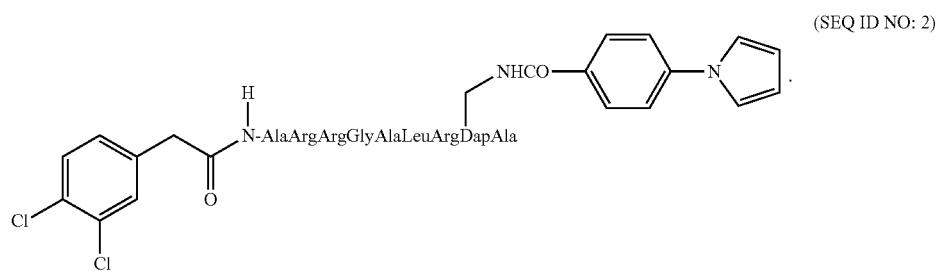
(SEQ ID NO: 2)
* * * * *

SEQUENCE LISTING

<160> NUMBER OF SEQ ID NOS: 17

<210> SEQ ID NO 1
<211> LENGTH: 8
<212> TYPE: PRT
<213> ORGANISM: unknown
<220> FEATURE:
<223> OTHER INFORMATION: sequence in protein kinase C-alpha inhibitor
<220> FEATURE:
<221> NAME/KEY: misc_feature
<222> LOCATION: (4)..(4)
<223> OTHER INFORMATION: X= any amino acid or amino acid mimetic
<220> FEATURE:
<221> NAME/KEY: misc_feature
<222> LOCATION: (5)..(5)
<223> OTHER INFORMATION: X= A or a Dap derivative
<220> FEATURE:
<221> NAME/KEY: misc_feature
<222> LOCATION: (6)..(6)
<223> OTHER INFORMATION: X= F, L or I
<220> FEATURE:
<221> NAME/KEY: misc_feature
<222> LOCATION: (7)..(7)
<223> OTHER INFORMATION: X= R or K
<220> FEATURE:
<221> NAME/KEY: misc_feature
<222> LOCATION: (8)..(8)
<223> OTHER INFORMATION: X= A or a Dap derivative

<400> SEQUENCE: 1

Ala Arg Arg Xaa Xaa Xaa Xaa Xaa
1               5

<210> SEQ ID NO 2
<211> LENGTH: 9
<212> TYPE: PRT
<213> ORGANISM: unknown
<220> FEATURE:
<223> OTHER INFORMATION: sequence in protein kinase C-alpha inhibitor
<220> FEATURE:
<221> NAME/KEY: misc_feature
<222> LOCATION: (5)..(5)
<223> OTHER INFORMATION: X = A or Dap
<220> FEATURE:
<221> NAME/KEY: misc_feature
<222> LOCATION: (8)..(8)
<223> OTHER INFORMATION: X = Q or Dap

<400> SEQUENCE: 2

Ala Arg Arg Gly Xaa Leu Arg Xaa Ala
1               5

<210> SEQ ID NO 3
<211> LENGTH: 5
<212> TYPE: PRT
<213> ORGANISM: unknown
<220> FEATURE:
<223> OTHER INFORMATION: preferred consensus sequence for protein
      kinase C-alpha
<220> FEATURE:
<221> NAME/KEY: misc_feature
<222> LOCATION: (4)..(4)
<223> OTHER INFORMATION: X= F, L or I
<220> FEATURE:
<221> NAME/KEY: misc_feature
<222> LOCATION: (5)..(5)
<223> OTHER INFORMATION: X= R or K

<400> SEQUENCE: 3

Lys Gly Ser Xaa Xaa
1               5

```
<210> SEQ ID NO 4
<211> LENGTH: 6
<212> TYPE: PRT
<213> ORGANISM: unknown
<220> FEATURE:
<223> OTHER INFORMATION: consensus sequence for protein kinase C-beta
      I, protein kinase C-beta II and protein kinase C-gamma.

<400> SEQUENCE: 4

Arg Lys Gly Ser Phe Lys
1               5

<210> SEQ ID NO 5
<211> LENGTH: 5
<212> TYPE: PRT
<213> ORGANISM: unknown
<220> FEATURE:
<223> OTHER INFORMATION: consensus sequence for protein kinase C-delta
<220> FEATURE:
<221> NAME/KEY: misc_feature
<222> LOCATION: (1)..(1)
<223> OTHER INFORMATION: X= K or Q
<220> FEATURE:
<221> NAME/KEY: misc_feature
<222> LOCATION: (5)..(5)
<223> OTHER INFORMATION: X= F or M

<400> SEQUENCE: 5

Xaa Gly Ser Phe Xaa
1               5

<210> SEQ ID NO 6
<211> LENGTH: 5
<212> TYPE: PRT
<213> ORGANISM: unknown
<220> FEATURE:
<223> OTHER INFORMATION: consensus sequence for protein kinase C-epsilon
<220> FEATURE:
<221> NAME/KEY: misc_feature
<222> LOCATION: (2)..(2)
<223> OTHER INFORMATION: X= M or K
<220> FEATURE:
<221> NAME/KEY: misc_feature
<222> LOCATION: (4)..(4)
<223> OTHER INFORMATION: X= F or A
<220> FEATURE:
<221> NAME/KEY: misc_feature
<222> LOCATION: (5)..(5)
<223> OTHER INFORMATION: X= G, Y, D or F

<400> SEQUENCE: 6

Lys Xaa Ser Xaa Xaa
1               5

<210> SEQ ID NO 7
<211> LENGTH: 6
<212> TYPE: PRT
<213> ORGANISM: unknown
<220> FEATURE:
<223> OTHER INFORMATION: consensus sequence for protein kinase C-eta

<400> SEQUENCE: 7

Arg Arg Ser Phe Arg Arg
1               5

<210> SEQ ID NO 8
<211> LENGTH: 5
<212> TYPE: PRT
<213> ORGANISM: unknown
<220> FEATURE:
<223> OTHER INFORMATION: consensus sequence for protein kinase C-zeta
```

```
<220> FEATURE:
<221> NAME/KEY: misc_feature
<222> LOCATION: (1)..(1)
<223> OTHER INFORMATION: X = R, Q, K or E
<220> FEATURE:
<221> NAME/KEY: misc_feature
<222> LOCATION: (2)..(2)
<223> OTHER INFORMATION: X = M or G
<220> FEATURE:
<221> NAME/KEY: misc_feature
<222> LOCATION: (4)..(5)
<223> OTHER INFORMATION: X = F or M

<400> SEQUENCE: 8

Xaa Xaa Ser Xaa Xaa
1               5

<210> SEQ ID NO 9
<211> LENGTH: 5
<212> TYPE: PRT
<213> ORGANISM: unknown
<220> FEATURE:
<223> OTHER INFORMATION: consensus sequence for protein kinase C-mu
<220> FEATURE:
<221> NAME/KEY: misc_feature
<222> LOCATION: (1)..(1)
<223> OTHER INFORMATION: X= Q, K, E or M
<220> FEATURE:
<221> NAME/KEY: misc_feature
<222> LOCATION: (4)..(4)
<223> OTHER INFORMATION: X= V, M or L
<220> FEATURE:
<221> NAME/KEY: misc_feature
<222> LOCATION: (5)..(5)
<223> OTHER INFORMATION: X= A, M or V

<400> SEQUENCE: 9

Xaa Met Ser Xaa Xaa
1               5

<210> SEQ ID NO 10
<211> LENGTH: 7
<212> TYPE: PRT
<213> ORGANISM: unknown
<220> FEATURE:
<223> OTHER INFORMATION: consensus substrate sequence for protein
      kinase C-alpha
<220> FEATURE:
<221> NAME/KEY: misc_feature
<222> LOCATION: (6)..(6)
<223> OTHER INFORMATION: X= F, L or I

<400> SEQUENCE: 10

Arg Arg Lys Gly Ser Xaa Arg
1               5

<210> SEQ ID NO 11
<211> LENGTH: 5
<212> TYPE: PRT
<213> ORGANISM: unknown
<220> FEATURE:
<223> OTHER INFORMATION: sequence of peptide substrate used for PKC
      alpha, beta and gamma assays

<400> SEQUENCE: 11

Ser Phe Arg Arg Arg
1               5

<210> SEQ ID NO 12
<211> LENGTH: 11
<212> TYPE: PRT
<213> ORGANISM: unknown
```

```
<220> FEATURE:
<223> OTHER INFORMATION: sequence of peptide substrate for PKC epsilon
      and zeta assays

<400> SEQUENCE: 12

Pro Arg Lys Arg Glu Gly Ser Val Arg Arg Arg
1               5                   10

<210> SEQ ID NO 13
<211> LENGTH: 9
<212> TYPE: PRT
<213> ORGANISM: unknown
<220> FEATURE:
<223> OTHER INFORMATION: starting consensus sequence peptide for
      derivation of PKC inhibitors

<400> SEQUENCE: 13

Arg Arg Gln Gly Ala Phe Met Tyr Phe
1               5

<210> SEQ ID NO 14
<211> LENGTH: 12
<212> TYPE: PRT
<213> ORGANISM: unknown
<220> FEATURE:
<223> OTHER INFORMATION: sequence of peptide substrate for synthesis
      of PKC isoforms

<400> SEQUENCE: 14

Pro Arg Lys Arg Gln Gly Ser Val Arg Arg Arg Val
1               5                   10

<210> SEQ ID NO 15
<211> LENGTH: 6
<212> TYPE: PRT
<213> ORGANISM: unknown
<220> FEATURE:
<223> OTHER INFORMATION: sequence for peptide substrate for PKC alpha,
      beta and gamma assays

<400> SEQUENCE: 15

Ser Phe Arg Arg Arg Arg
1               5

<210> SEQ ID NO 16
<211> LENGTH: 12
<212> TYPE: PRT
<213> ORGANISM: unknown
<220> FEATURE:
<223> OTHER INFORMATION: sequence for peptide substrate for PKC delta,
      epsilon, theta, eta, iota and zeta assays

<400> SEQUENCE: 16

Pro Arg Lys Arg Glu Gly Ser Val Arg Arg Arg Val
1               5                   10

<210> SEQ ID NO 17
<211> LENGTH: 9
<212> TYPE: PRT
<213> ORGANISM: unknown
<220> FEATURE:
<223> OTHER INFORMATION: protein sequence in inhibitor of PKC
<220> FEATURE:
<221> NAME/KEY: misc_feature
<222> LOCATION: (5)..(5)
<223> OTHER INFORMATION: X = a Dap derivative

<400> SEQUENCE: 17

Arg Arg Gln Gly Xaa Phe Met Tyr Phe
```